(12) United States Patent
Schneider et al.

(10) Patent No.: US 10,501,539 B2
(45) Date of Patent: Dec. 10, 2019

(54) COMPOSITIONS AND METHODS FOR TREATING CANCER WITH ANTI-CD19 IMMUNOTHERAPY

(71) Applicants: LENTIGEN TECHNOLOGY, INC., Gaithersburg, MD (US); The U.S.A., as represented by the Secretary, Department of Health and Human Services, Bethesda, MD (US)

(72) Inventors: Dina Schneider, Potomac, MD (US); Rimas J. Orentas, Seattle, WA (US); Boro Dropulic, Ellicott City, MD (US); Dimiter S. Dimitrov, Frederick, MD (US); Zhongyu Zhu, Frederick, MD (US)

(73) Assignees: Lentigen Technology Inc., Gaithersburg, MD (US); The U.S.A., as Represented By The Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/132,064

(22) Filed: Sep. 14, 2018

(65) Prior Publication Data
US 2019/0106492 A1   Apr. 11, 2019

Related U.S. Application Data

(60) Provisional application No. 62/559,297, filed on Sep. 15, 2017.

(51) Int. Cl.
| | | |
|---|---|---|
| *C07K 16/28* | (2006.01) | |
| *A61P 35/00* | (2006.01) | |
| *C07K 14/705* | (2006.01) | |
| *C07K 14/725* | (2006.01) | |
| *A61K 35/17* | (2015.01) | |
| *C12N 5/0783* | (2010.01) | |
| *A61K 39/00* | (2006.01) | |
| *A61K 35/12* | (2015.01) | |

(52) U.S. Cl.
CPC .......... *C07K 16/2803* (2013.01); *A61K 35/17* (2013.01); *A61K 39/0011* (2013.01); *A61P 35/00* (2018.01); *C07K 14/7051* (2013.01); *C07K 14/70517* (2013.01); *C07K 14/70521* (2013.01); *C07K 14/70596* (2013.01); *C12N 5/0636* (2013.01); *A61K 2035/124* (2013.01); *A61K 2039/5156* (2013.01); *C07K 2317/21* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/035* (2013.01); *C07K 2319/30* (2013.01); *C07K 2319/33* (2013.01); *C12N 2501/599* (2013.01); *C12N 2510/00* (2013.01)

(58) Field of Classification Search
CPC ............ C07K 14/7051; C07K 16/2803; C07K 2317/622; C07K 2319/02; C07K 2319/03; C07K 14/70578; C07K 2317/56; C07K 14/705; C07K 14/70517; C07K 14/70521; C07K 2317/31; C07K 2317/73; C07K 16/2887; C07K 19/00; C07K 2317/53; C07K 2317/54; C07K 2317/55; C07K 2317/565; C07K 2317/92; C07K 2319/00; C07K 2319/30; C07K 2319/33; C07K 2319/70; C07K 2319/74; A61K 35/17; A61K 2039/505; A61P 35/00; A61P 35/02; C12N 15/87; G01N 33/57492
USPC ............ 424/93.2, 93.21, 93.7, 136.1, 173.1, 424/174.1, 184.1; 435/320.1, 325, 328, 435/254.11, 372.3
See application file for complete search history.

(56) References Cited

U.S. PATENT DOCUMENTS

2014/0378664 A1   12/2014   Suh et al.

FOREIGN PATENT DOCUMENTS

| | | |
|---|---|---|
| WO | 2003/085093 | 10/2003 |
| WO | 2004/003144 | 1/2004 |
| WO | 2008/028946 | 3/2008 |
| WO | 2008/150485 | 12/2008 |
| WO | 2009/055054 | 4/2009 |
| WO | 2013/070565 | 5/2013 |

OTHER PUBLICATIONS

Kean et al., Defining success with cellular therapeutics: the current landscape for clinical end point and toxicity analysis 2018, Bloo pp. 2630-2639 (Year: 2018).*
Wang et al Treatment of CD33-directed Chimeric Antigen Receptor-modified T Cells in One Patient With Relapsed and Refractory Acute Myeloid Leukemia, 2015, Molecular Therapy vol. 23 No. 1, 184-191 (Year: 2015).*
Voskoglou-Nomikos et al., Clinical Predictive Value of the in Vitro Cell Line, Human Xenograft, and Mouse Allograft Preclinical Cancer Models1(Clinical Cancer Research, 2003, 9, 4227-4239) (Year: 2003).*
International Search Report and Written Opinion issued in PCT/US18/51167, dated Jan. 3, 2019.

* cited by examiner

*Primary Examiner* — Janet L Epps-Smith
(74) *Attorney, Agent, or Firm* — Serg Sira, Esq.; Fish & Richardson P.C.

(57) ABSTRACT

Chimeric antigen receptors containing human CD19 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

6 Claims, 14 Drawing Sheets

Specification includes a Sequence Listing.

LTG2050: LP-M19217-CD8 TM-41BB-CD3 zeta nucleic acid sequence (SEQ ID NO: 19)

ATGCTTCTCCTGGTCACCTCCCTGCTCCTCTGCGAACTGCCTCACCCTGCCTTCCTTC
TGATTCCTGAGGTCCAGCTGGTACAGTCTGGAGCTGAGGTGAAGAAGCCTGGGGCCT
CAGTGAAGGTCTCCTGCAAGGCTTCTGGATACACCTTCACCAGCTACTATATGCACTG
GGTGCGACAGGCCCCTGGACAAGGGCTTGAGTGGATGGGAATAATCAACCCTAGTG
GTGGTAGCACAAGCTACGCACAGAAGTTCCAGGGCAGAGTCACCATGACCAGGGACA
CGTCCACGAGCACAGTCTACATGGAGCTGAGCAGCCTGAGATCTGAGGACACGGCC
GTGTATTACTGTGCGAGATCGGATCGGGGAATTACCGCCACGGACGCTTTTGATATCT
GGGGCCAAGGGACAATGGTCACCGTCTCTTCAGGAGGTGGCGGGTCTGGTGGAGGC
GGTAGCGGTGGTGGCGGATCCCAGTCTGTGCTGACTCAGCCACCCTCGGTGTCAGT
GGCCCCAGGGCAGACGGCCAAGATTACCTGTGGGGGAAGTGACATTGGAAATAAAAA
TGTCCACTGGTACCAGCAGAAGCCAGGCCAGGCCCCTGTCCTGGTCGTCTATGATGA
TTACGACCGGCCCTCAGGGATCCCTGAGCGATTCTCTGGCTCCAACTCTGGGGACGC
GGCCACCCTGACGATCAGCACGGTCGAAGTCGGGGATGAGGCCGACTATTTCTGTCA
GGTGTGGGACAGTAGTGGTGATCCTTATTGGGTGTTCGGCGGAGGGACCCAGCTCAC
CGTTTTAGGTGCGGCCGCAACTACCACCCCTGCCCCTCGGCCGCCGACTCCGGCCC
CAACCATCGCAAGCCAACCCCTCTCCTTGCGCCCCGAAGCTTGCCGCCCGGCCGCG
GGTGGAGCCGTGCATACCCGGGGGCTGGACTTTGCCTGCGATATCTACATTTGGGCC
CCGCTGGCCGGCACTTGCGGCGTGCTCCTGCTGTCGCTGGTCATCACCCTTTACTGC
AAGAGGGGCCGGAAGAAGCTGCTTTACATCTTCAAGCAGCCGTTCATGCGGCCCGTG
CAGACGACTCAGGAAGAGGACGGATGCTCGTGCAGATTCCCTGAGGAGGAAGAGGG
GGGATGCGAACTGCGCGTCAAGTTCTCACGGTCCGCCGACGCCCCCGCATATCAACA
GGGCCAGAATCAGCTCTACAACGAGCTGAACCTGGGAAGGAGAGAGGAGTACGACG
TGCTGGACAAGCGACGCGGACGCGACCCGGAGATGGGGGGGAAACCACGGCGGAA
AAACCCTCAGGAAGGACTGTACAACGAACTCCAGAAAGACAAGATGGCGGAAGCCTA
CTCAGAAATCGGGATGAAGGGAGAGCGGAGGAGGGGAAAGGGTCACGACGGGCTGT
ACCAGGGACTGAGCACCGCCACTAAGGATACCTACGATGCCTTGCATATGCAAGCAC
TCCCACCCCGG

LTG2050: LP-M19217-CD8 TM-41BB-CD3zeta amino acid sequence (SEQ ID NO: 20)

MLLLVTSLLLCELPHPAFLLIPEVQLVQSGAEVKKPGASVKVSCKASGYTFTSYYMHWVRQ
APGQGLEWMGIINPSGGSTSYAQKFQGRVTMTRDTSTSTVYMELSSLRSEDTAVYYCARS
DRGITATDAFDIWGQGTMVTVSSGGGGSGGGGSGGGGSQSVLTQPPSVSVAPGQTAKIT
CGGSDIGNKNVHWYQQKPGQAPVLVVYDDYDRPSGIPERFSGSNSGDAATLTISTVEVGD
EADYFCQVWDSSGDPYWVFGGGTQLTVLGAAATTTPAPRPPTPAPTIASQPLSLRPEACR
PAAGGAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDKR
RGRDPEMGGKPRRKNPQEGLYNELQKDMAEAYSEIGMKGERRRGKGHDGLYQGLSTA
TKDTYDALHMQALPPR

FIGURE 2A

LTG2065: LP-M19217-1-CD8 TM-41BB-CD3 zeta nucleic acid sequence (SEQ ID NO: 21)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAAGAAGCCTGGGGC
CTCAGTGAAGGTCTCCTGCAAGGCTTCTGGATACACCTTCACCAGCTACTATATGCAC
TGGGTGCGACAGGCCCCTGGACAAGGGCTTGAGTGGATGGGATTAATCAACCCTAGT
GGTGGTAGCACAAGCTACGCACAGAAGTTCCAGGGCAGAGTCACCATGACCAGGGA
CACGTCCACGAGCACAGTCTACATGGAGCTGAGCAGCCTGAGATCTGAGGACACGGC
CGTGTATTACTGTGCGAGATCGGATCGGGGAATTACCGCCACGGACGCTTTTGATATC
TGGGGCCAAGGGACAATGGTCACCGTCTCTTCAGGCGGAGGAGGCTCCGGGGGAGG
AGGTTCCGGGGGCGGGGGTTCCCAGTCTGTGCTGACTCAGCCACCCTCGGTGTCAG
TGGCCCCAGGGCGGATGGCCAAGATTACCTGTGGGGGAAGTGACATTGGAAATAAAA
ATGTCCACTGGTATCAGCAGAAGCCAGGCCAGGCCCCTGTCCTGGTTGTCTATGATG
ATTACGACCGGCCCTCAGGGATCCCTGAGCGATTCTCTGGCTCCAACTCTGGGGACG
CGGCCACCCTGACGATCAGCACGGTCGAAGTCGGGGATGAGGCCGACTATTTCTGTC
AGGTGTGGGACGGTAGTGGTGATCCTTATTGGATGTTCGGCGGAGGGACCCAGCTCA
CCGTTTTAGGTGCGGCCGCAACTACCACCCCTGCCCCTCGGCCGCCGACTCCGGCC
CCAACCATCGCAAGCCAACCCCTCTCCTTGCGCCCCGAAGCTTGCCGCCCGGCCGC
GGGTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTACTG
CAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACGA
CGTGCTGGACAAGCGACGCGGACGCGACCCGGAGATGGGGGGGAAACCACGGCGG
AAAAACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGGGCT
GTACCAGGGACTGAGCACCGCCACTAAGGATACCTACGATGCCTTGCATATGCAAGC
ACTCCCACCCCGG

LTG2065: LP-M19217-1-CD8 TM-41BB-CD3 zeta amino acid sequence (SEQ ID NO: 22)

MLLLVTSLLLCELPHPAFLLIPEVQLVQSGAEVKKPGASVKVSCKASGYTFTSYYMHWVR
QAPGQGLEWMGLINPSGGSTSYAQKFQGRVTMTRDTSTSTVYMELSSLRSEDTAVYYCA
RSDRGITATDAFDIWGQGTMVTVSSGGGGSGGGGSGGGGSQSVLTQPPSVSVAPGRM
AKITCGGSDIGNKNVHWYQQKPGQAPVLVVYDDYDRPSGIPERFSGSNSGDAATLTISTV
EVGDEADYFCQVWDGSGDPYWMFGGGTQLTVLGAAATTTPAPRPPTPAPTIASQPLSLR
PEACRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGL
YQGLSTATKDTYDALHMQALPPR

FIGURE 2B

LTG2066: LP-M19217-2-CD8 TM-41BB-CD3 zeta nucleic acid sequence (SEQ ID NO: 23)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAAGAAGCCTGGGGCC
TCAGTGAAGGTCTCCTGCAAGGCTTCCGGATACACCTTCACCAGCTACTACATGCACT
GGGTGCGACAGGCCCCTGGACAAGGGTTTGAGTGGATGGGATTAATCAACCCTAGTG
GTAGTAGCACAAGCTACGCACAGAAGTTCCAGGGCAGAGTCACCATGACCAGGGACA
CGTCCACGAGCACAGTCTACATGGAGCTGAGCAACCTGAGATCTGAGGACACGGCCG
TGTATTACTGTGCGAGATCGGATCGGGGAATTACCGCCACGGACGCTTTTGATATCTG
GGGCCAAGGGACAATGGTCACCGTCTCTTCAGGCGGAGGAGGCTCCGGGGGAGGAG
GTTCCGGGGGCGGGGGTTCCCAGTCTGTGCTGACTCAGCCACCCTCGGTGCCAGTG
GCCCCAGGGCAGACGGCCAAGATTATCTGTGGGGGAAGTGACATTGGAAATAAAAAT
GTCCACTGGTACCAGCAGAAGCCAGGCCAGGCCCCTGTCCTGGTCGTCTATGATGAC
TACGACCGGCCCTCAGGGATCCCTGAGCGATTCTCTGGCTCCAACTCTGGGGACGCG
GCCACCCTGACGATCAGCACGGTTGAAGTCGGGGATGAGGCCGACTATTTCTGTCAG
GTGTGGGACGGTAGTGGTGATCCTTATTGGGTGTTCGGCGGAGGGACCCAGCTCACC
GTCTTAGGTGCGGCCGCAACTACCACCCCTGCCCCTCGGCCGCCGACTCCGGCCCCA
ACCATCGCAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTGGGCCCCG
CTGGCCGGCACTTGCGGCGTGCTCCTGCTGTCGCTGGTCATCACCCTTTACTGCAAGA
GGGGCCGGAAGAAGCTGCTTTACATCTTCAAGCAGCCGTTCATGCGGCCCGTGCAGA
CGACTCAGGAAGAGGACGGATGCTCGTGCAGATTCCCTGAGGAGGAAGAGGGGGGA
TGCGAACTGCGCGTCAAGTTCTCACGGTCCGCCGACGCCCCGCATATCAACAGGGC
CAGAATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAACCC
TCAGGAAGGACTGTACAACGAACTCCAGAAAGACAAGATGGCGGAAGCCTACTCAGAA
ATCGGGATGAAGGGAGAGCGGAGGAGGGGAAAGGGTCACGACGGGCTGTACCAGGG
ACTGAGCACCGCCACTAAGGATACCTACGATGCCTTGCATATGCAAGCACTCCCACCC
CGG

LTG2066: LP-M19217-2-CD8 TM-41BB-CD3 zeta amino acid sequence (SEQ ID NO: 24)

MLLLVTSLLLCELPHPAFLLIPEVQLVQSGAEVKKPGASVKVSCKASGYTFTSYYMHWVR
QAPGQGFEWMGLINPSGSSTSYAQKFQGRVTMTRDTSTSTVYMELSNLRSEDTAVYYCA
RSDRGITATDAFDIWGQGTMVTVSSGGGGSGGGGSGGGGSQSVLTQPPSVPVAPGQTA
KIICGGSDIGNKNVHWYQQKPGQAPVLVVYDDYDRPSGIPERFSGSNSGDAATLTISTVEV
GDEADYFCQVWDGSGDPYWVFGGGTQLTVLGAAATTTPAPRPPTPAPTIASQPLSLRPE
ACRPAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLYQ
GLSTATKDTYDALHMQALPPR

FIGURE 2C

LTG2067: LP-M19217-7-CD8 TM-41BB-CD3 zeta nucleic acid sequence (SEQ ID NO: 25)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAACAAGCCTGGTGCC
TCAGTGAAGGTCTCCTGCAAGGCTTCTGGATACACCTTCACCAGCTACTATATGCACT
GGGTGCGACAGGCCCCTGGACAAGGGCTTGAGTGGATGGGAATGATCAACCCTAGT
GGTGGTAGCACAAGCTACGCACAGAAGTTCCAGGGCAGAGTCACCATGACCAGGGA
CACGTCCACGAGCACAGTCTACATGGAGCTGAGCAGCCTGAGATCTGAGGACACGGC
CGTGTATTACTGTGCGAGATCGGATCGGGGAATTACCTCCACGGACGCTTTTGATATC
TGGGGCCAAGGGACAATGGTCACCGTCTCTTCAGGCGGAGGAGGCTCCGGGGGAGG
AGGTTCCGGGGGCGGGGGTTCCCAGTCTGTGCTGACTCAGCCACCCTCGGTGTCATT
GGCCCCAGGGCAGACGGCCAAGATTACCTGTGGGGGAAGTGACATTGGAAATAAAAA
TGTCCACTGGTACCAGCAGAAGCCAGGCCAGGCCCTGTCCTAGTCGTCTATGATGA
TTACAACCGGCCCTCAGGGATCCCTGAGCGATTCTCTGGCTCCAACTCTGGGGACTC
AGCCACCCTGACGATCAGCACGGTCGAAGTCGGGGATGAGGCCGACTATTTCTGTCA
GGTGTGGGACGGTAGTGGTGATCCTTATTGGGTGTTCGGCGGAGGGACCCAGCTCA
CCGTTTTAGGTGCGGCCGCAACTACCACCCCTGCCCCTCGGCCGCCGACTCCGGCC
CCAACCATCGCAAGCCAACCCCTCTCCTTGCGCCCCGAAGCTTGCCGCCCGGCCGC
GGGTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTACTG
CAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACGA
CGTGCTGGACAAGCGACGCGGACGCGACCCGGAGATGGGGGGGAAACCACGGCGG
AAAAACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGGGCT
GTACCAGGGACTGAGCACCGCCACTAAGGATACCTACGATGCCTTGCATATGCAAGC
ACTCCCACCCCGG

LTG2067: LP-M19217-7-CD8 TM-41BB-CD3 zeta amino acid sequence (SEQ ID NO: 26)

MLLLVTSLLLCELPHPAFLLIPEVQLVQSGAEVNKPGASVKVSCKASGYTFTSYYMHWVR
QAPGQGLEWMGMINPSGGSTSYAQKFQGRVTMTRDTSTSTVYMELSSLRSEDTAVYYC
ARSDRGITSTDAFDIWGQGTMVTVSSGGGGSGGGGSGGGGSQSVLTQPPSVSLAPGQT
AKITCGGSDIGNKNVHWYQQKPGQAPVLVVYDDYNRPSGIPERFSGSNSGDSATLTISTV
EVGDEADYFCQVWDGSGDPYWVFGGGTQLTVLGAAATTTPAPRPPTPAPTIASQPLSLR
PEACRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGL
YQGLSTATKDTYDALHMQALPPR

FIGURE 2D

LTG2068: LP-M19217-23-CD8 TM-41BB-CD3 zeta nucleic acid sequence (SEQ ID NO: 27)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAAGAAGCCTGGGGC
CTCAGTGAAGGTCTCCTGCAAGGCATCTGGATACACCTTCACCGGCTACTATATGCAC
TGGGTGCGGCAGGCCCCTGGACAAGGGCTTGAGTGGATAGGATTAATCAACCCTAGT
GGTGGTAGCACAAGCTACGAACAGAAGTTCCAGGGCAGAGTCGCCATGACCAGGGA
CACGTCAACGAGCACAGTCTACATGGAGCTGAGCAGCCTGAGATCTGAGGACACGGC
CGTGTATTACTGTGCGAGATCGGATCGGGGAATTACCGCCACGGACGCTTTTGATATC
TGGGGCCAAGGGACAATGGTCACCGTCTCTTCAGGCGGAGGAGGCTCCGGGGGAGG
AGGTTCCGGGGGCGGGGGTTCCCAGTCTGTGCTGACTCAGCCACCCTCGGTGTCAG
TGGCCCCAGGGCAGACGGCCAAGATTACCTGTGGGGAAGTGACATTGGAGATAAAA
ATGTCCACTGGTACCAGCAGAAGCCAGGCCAGGCCCCTGTCCTGGTCGTCTATGATG
ATTACGACCGGCCCTCAGGGATCCCTGAGCGATTCTCTGGCTCCAACTCTGGGGACG
CGGCCACCCTGACGATCAGCACGGTCGAAGTCGGGGATGAGGCCGACTATTTCTGTC
AGGTGTGGGACGGTATTGGTGATCCCTATTGGGTGTTCGGCGGAGGGACCCAGCTCA
CCGTTTTAGGTGCGGCCGCAACTACCACCCCTGCCCCTCGGCCGCCGACTCCGGCC
CCAACCATCGCAAGCCAACCCCTCTCCTTGCGCCCCGAAGCTTGCCGCCCGGCCGC
GGGTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTACTG
CAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACGA
CGTGCTGGACAAGCGACGCGGACGCGACCCGGAGATGGGGGGGAAACCACGGCGG
AAAAACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGGGCT
GTACCAGGGACTGAGCACCGCCACTAAGGATACCTACGATGCCTTGCATATGCAAGC
ACTCCCACCCCGG

LTG2068: LP-M19217-23-CD8 TM-41BB-CD3 zeta amino acid sequence (SEQ ID NO: 28)

MLLLVTSLLLCELPHPAFLLIPEVQLVQSGAEVKKPGASVKVSCKASGYTFTGYYMHWVR
QAPGQGLEWIGLINPSGGSTSYEQKFQGRVAMTRDTSTSTVYMELSSLRSEDTAVYYCA
RSDRGITATDAFDIWGQGTMVTVSSGGGGSGGGGSGGGGSQSVLTQPPSVSVAPGQTA
KITCGGSDIGDKNVHWYQQKPGQAPVLVVYDDYDRPSGIPERFSGSNSGDAATLTISTVE
VGDEADYFCQVWDGIGDPYWVFGGGTQLTVLGAAATTTPAPRPPTPAPTIASQPLSLRPE
ACRPAAGGAVHTRGLDFACDIYIWAPLAGTCGVLLLSLVITLYCKRGRKKLLYIFKQPFMRP
VQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLYQ
GLSTATKDTYDALHMQALPPR

FIGURE 2E

LTG2069: LP-M19217-29-CD8 TM-41BB-CD3 zeta nucleic acid sequence (SEQ ID NO: 29)

ATGCTGCTGCTGGTGACCAGCCTGCTGCTGTGCGAACTGCCGCATCCGGCGTTTCTG
CTGATTCCGGAGGTCCAGCTAGTACAGTCTGGAGCTGAGGTGAAGAAGCCTGGGGC
CTCAGTGAAGGTCTCCTGCAAGGCTTCTGGATACACCTTCACCAGCTACTATATGCAC
TGGGTGCGACAGGCCCCTGGACAAGGGCTTGAGTGGATGGGAATGATCAACCCTAGT
GGTGGTAGCACAAGCTACGCACAGAAGTTCCAGGGCAGAGTCACCATGACCAGGGA
CACGTCCACGAGCACAGTCTACATGGAGCTGAGCAGCCTGAGATCTGAGGACACGGC
CGTGTATTACTGTGCGAGATCGGATCGGGGAATTACCGCCACGGACGCTTTTGATATC
TGGGGCCAAGGGACAATGGTCACCGTCTCTTCAGGCGGAGGAGGCTCCGGGGGAGG
AGGTTCCGGGGGCGGGGGTTCCCAGTCTGTGCTGACTCAGCCACCCTCGGTGTCAG
TGGCCCCAGGGCAGACGGCCAAGATTACCTGTGGGGGAAGTGACATTGGAAATAAAA
ATGCCCACTGGTACCAGCAGAAGCCAGGCCAGGCCCTGTCCTGGTCGTCTATGATG
ATTACGACCGGCCCTCAGGGATCTCTGAGCGATTCTCTGGCTCCAACTCTGGGGACG
CGGCCACCCTGACGATCAGCACGGTCGAAGTCGGGGATGAGGCCGACTATTTCTGTC
AGGTGTGGGACGGTAGTGGTGATCCTTTTTGGGTGTTCGGCGGAGGGACCCAGCTCA
CCGTTTTAGGTGCGGCCGCAACTACCACCCCTGCCCCTCGGCCGCCGACTCCGGCC
CCAACCATCGCAAGCCAACCCTCTCCTTGCGCCCCGAAGCTTGCCGCCCGGCCGC
GGGTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTACTG
CAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGG
GGGGATGCGAACTGCGCGTCAAGTTCTCACGGTCCGCCGACGCCCCCGCATATCAA
CAGGGCCAGAATCAGCTCTACAACGAGCTGAACCTGGGAAGGAGAGAGGAGTACGA
CGTGCTGGACAAGCGACGCGGACGCGACCCGGAGATGGGGGGGAAACCACGGCGG
AAAAACCCTCAGGAAGGACTGTACAACGAACTCCAGAAAGACAAGATGGCGGAAGCC
TACTCAGAAATCGGGATGAAGGGAGAGCGGAGGAGGGGAAAGGGTCACGACGGGCT
GTACCAGGGACTGAGCACCGCCACTAAGGATACCTACGATGCCTTGCATATGCAAGC
ACTCCCACCCCGG

LTG2069: LP-M19217-29-CD8 TM-41BB-CD3 zeta amino acid sequence (SEQ ID NO: 30)

MLLLVTSLLLCELPHPAFLLIPEVQLVQSGAEVKKPGASVKVSCKASGYTFTSYYMHWVR
QAPGQGLEWMGMINPSGGSTSYAQKFQGRVTMTRDTSTSTVYMELSSLRSEDTAVYYC
ARSDRGITATDAFDIWGQGTMVTVSSGGGGSGGGGSGGGGSQSVLTQPPSVSVAPGQT
AKITCGGSDIGNKNAHWYQQKPGQAPVLVVYDDYDRPSGISERFSGSNSGDAATLTISTV
EVGDEADYFCQVWDGSGDPFWVFGGGTQLTVLGAAATTTPAPRPPTPAPTIASQPLSLR
PEACRPAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGL
YQGLSTATKDTYDALHMQALPPR

FIGURE 2F

LTG2070: LP-M19217-38-CD8 TM-41BB-CD3 zeta nucleic acid sequence (SEQ ID NO:31)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAAGAGGCCTGGGGC
CTCAGTGAAGGTCTCCTGCAAGGCTTCTGGATACACCTTCACCAGCTACTATATGCAC
TGGGTGCGACAGGCCCCTGGACGAGGGCTTGAGTGGATGGGATTAATCAACCCTAGT
GGTGGTAGCACAAGCTACGCACAGGAGTTCCAGGGCAGAGTCACCATGACCAGGGA
CATGTCCACGAGCACAGTCTACATGGAGCTGAGCAGCCTGAGATCTGAGGACACGGC
CGTGTATTACTGTGCGAGATCGGATCGGGGAATTAGCGCCACGGACGCTTTTGATAT
CTGGGGCCAAGGGACAATGGTCACCGTCTCTTCAGGCGGAGGAGGCTCCGGGGGAG
GAGGTTCCGGGGGCGGGGGTTCCCAGTCTGTGCTGACTCAGCCACCCTCGGTGTCA
GTGGCCCCAGGGCAGATGGCCAAGATTACCTGTGGGGGAAGTGACATTGGAAATAAA
AATGTCCACTGGTACCAGCAGAAGCCAGGCCAGGCCCCTGTCCTGGTCGTCTATGAT
GATTACAACCGGCCCTCAGGGATCCCTGAGCGATTCTCTGGCTCCAACTCTGGGGAC
GCGGCCACCCTGACGATCAGCACGGTCGAAGTCGGGGATGAGGCCGACTATTTCTGT
CAGGTATGGGACGGTAGTGGTGATCCTTATGGGTGTTCGGCGGAGGGACCCAGCTC
ACCGATTTAGGTGCGGCCGCAACTACCACCCCTGCCCCTCGGCCGCCGACTCCGGC
CCCAACCATCGCAAGCCAACCCCTCTCCTTGCGCCCCGAAGCTTGCCGCCCGGCCG
CGGGTGGAGCCGTGCATACCCGGGGGCTGGACTTTGCCTGCGATATCTACATTTGGG
CCCCGCTGGCCGGCACTTGCGGCGTGCTCCTGCTGTCGCTGGTCATCACCCTTTACT
GCAAGAGGGGCCGGAAGAAGCTGCTTTACATCTTCAAGCAGCCGTTCATGCGGCCCG
TGCAGACGACTCAGGAAGAGGACGGATGCTCGTGCAGATTCCTGAGGAGGAAGAG
GGGGGATGCGAACTGCGCGTCAAGTTCTCACGGTCCGCCGACGCCCCCGCATATCA
ACAGGGCCAGAATCAGCTCTACAACGAGCTGAACCTGGGAAGGAGAGAGGAGTACG
ACGTGCTGGACAAGCGACGCGGACGCGACCCGGAGATGGGGGGGAAACCACGGCG
GAAAAACCCTCAGGAAGGACTGTACAACGAACTCCAGAAAGACAAGATGGCGGAAGC
CTACTCAGAAATCGGGATGAAGGGAGAGCGGAGGAGGGGAAAGGGTCACGACGGGC
TGTACCAGGGACTGAGCACCGCCACTAAGGATACCTACGATGCCTTGCATATGCAAG
CACTCCCACCCCGG

LTG2070: LP-M19217-38-CD8 TM-41BB-CD3 zeta amino acid sequence (SEQ ID NO: 32)

MLLLVTSLLLCELPHPAFLLIPEVQLVQSGAEVKRPGASVKVSCKASGYTFTSYYMHWVR
QAPGRGLEWMGLINPSGGSTSYAQEFQGRVTMTRDMSTSTVYMELSSLRSEDTAVYYC
ARSDRGISATDAFDIWGQGTMVTVSSGGGGSGGGGSGGGGSQSVLTQPPSVSVAPGQ
MAKITCGGSDIGNKNVHWYQQKPGQAPVLVVYDDYNRPSGIPERFSGSNSGDAATLTIST
VEVGDEADYFCQVWDGSGDPYWVFGGGTQLTDLGAAATTTPAPRPPTPAPTIASQPLSL
RPEACRPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKGHDG
LYQGLSTATKDTYDALHMQALPPR

FIGURE 2G

LTG2071: LP-M19217-40-CD8 TM-41BB-CD3 nucleic acid sequence (SEQ ID NO: 33)

ATGCTGCTGCTGGTGACCAGCCTGCTGCTGTGCGAACTGCCGCATCCGGCGTTTCTG
CTGATTCCGGAGGTCCAGCTGGTACAGTCTGGAGCTGAGGTGAAGAGGCCTGGGGC
CTCAGTGAAGGTCTCCTGCAAGGCTTCTGGATACACCTTCACCAGCTACTATATGCAC
TGGGTGCGACAGGCCCCTGGACAAGGGCTTGTGTGGATGGGATTAATCAACCCTAGT
GGTGGCAGCACAAGCTACGCACAGAAGTTCCAGGGCAGAGTCACCATGACCAGGGA
CACGTCCACGAGCACAGTCTACATGGAGCTGAGCAGCCTGAGATCTGAGGACACGGC
CGTGTATTACTGTGCGAGATCGGATCGGGGAATTACCGCCACGGACGCTTTTGATATC
TGGGGCCAAGGGACAATGGTCACCGTCTCTTCAGGCGGAGGAGGCTCCGGGGGAGG
AGGTTCCGGGGGCGGGGGTTCCCAGTCTGTGCTGACTCAGCCACCCTCGGTCTCAG
TGGCCCCAGGGCAGACGGCCAAGACTACCTGTGGGGGAAGTGACATTGGAAATAAAA
ATGTCCACTGGTACCAGCAGAAGCCAGGCCAGGCCCCTGTCCTGGTCGTCTATGATG
ATTACGACCGGCCCTCAGGGATCCCTGAGCGATTCTCTGGCTCCAACTCTGGGGACG
CGGCCACCCTGACGATCAGCACGGTCGAAGTCGGGGATGAGGCCGACTATGTCTGT
CAGGTGTGGGACGGTAGTGGTGATCCTTATTGGGTGTTCGGCGGAGGGACCCAGCT
CACCGTTTTAGGTGCGGCCGCAACTACCACCCCTGCCCCTCGGCCGCCGACTCCGG
CCCCAACCATCGCAAGCCAACCCCTCTCCTTGCGCCCCGAAGCTTGCCGCCCGGCC
GCGGGTGGAGCCGTGCATACCCGGGGGCTGGACTTTGCCTGCGATATCTACATTTGG
GCCCCGCTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCATGCGGCCC
GTGCAGACGACTCAGGAAGAGGACGGATGCTCGTGCAGATTCCCTGAGGAGGAAGA
GGGGGGATGCGAACTGCGCGTCAAGTTCTCACGGTCCGCCGACGCCCCCGCATATC
AACAGGGCCAGAATCAGCTCTACAACGAGCTGAACCTGGGAAGGAGAGAGGAGTAC
GACGTGCTGGACAAGCGACGCGGACGCGACCCGGAGATGGGGGGGAAACCACGGC
GGAAAAACCCTCAGGAAGGACTGTACAACGAACTCCAGAAAGACAAGATGGCGGAAG
CCTACTCAGAAATCGGGATGAAGGAGAGCGGAGGAGGGGAAAGGGTCACGACGGG
CTGTACCAGGGACTGAGCACCGCCACTAAGGATACCTACGATGCCTTGCATATGCAA
GCACTCCCACCCCGG

LTG2071: LP-M19217-40-CD8 TM-41BB-CD3 zeta amino acid sequence (SEQ ID NO: 34)

MLLLVTSLLLCELPHPAFLLIPEVQLVQSGAEVKRPGASVKVSCKASGYTFTSYYMHWVR
QAPGQGLVWMGLINPSGGSTSYAQKFQGRVTMTRDTSTSTVYMELSSLRSEDTAVYYCA
RSDRGITATDAFDIWGQGTMVTVSSGGGGSGGGGSGGGGSQSVLTQPPSVSVAPGQTA
KTTCGGSDIGNKNVHWYQQKPGQAPVLVVYDDYDRPSGIPERFSGSNSGDAATLTISTVE
VGDEADYVCQVWDGSGDPYWVFGGGTQLTVLGAAATTTPAPRPPTPAPTIASQPLSLRP
EACRPAAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREEYD
VLDKRRGRDPEMGGKPRRKNPQEGLYNELQKDKMAEAYSEIGMKGERRRGKGHDGLY
QGLSTATKDTYDALHMQALPPR

FIGURE 2H

COMPOSITIONS AND METHODS FOR TREATING CANCER WITH ANTI-CD19 IMMUNOTHERAPY

CROSS-REFERENCE TO RELATED APPLICATIONS

This application claims the benefit of priority under 35 U.S.C. Section 119(e) to U.S. Provisional Patent Application No. 62/559,297 filed on Sep. 15, 2017, the entire contents of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. The ASCII copy, created on Sep. 13, 2018, is named Sequence Listing.txt and is 93.7 kilobytes in size.

FIELD OF THE DISCLOSURE

This application relates to the field of cancer, particularly to CD19 antigen binding domains and chimeric antigen receptors (CARs) containing such CD19 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

CD19 is a 85-95 kDa transmembrane cell surface glycoprotein receptor. CD19 is a member of immunoglobulin (Ig) superfamily of proteins, and contains two extracellular Ig-like domains, a transmembrane, and an intracellular signaling domain (Tedder T F, Isaacs, C M, 1989, J Immunol 143:712-171). CD19 modifies B cell receptor signaling, lowering the triggering threshold for the B cell receptor for antigen (Carter, R H, and Fearon, D T, 1992, Science, 256:105-107), and co-ordinates with CD81 and CD21 to regulate this essential B cell signaling complex (Bradbury, L E, Kansas G S, Levy S, Evans R L, Tedder T F, 1992, J Immunol, 149:2841-50). During B cell ontogeny CD19 is able to signal at the pro-B, pre-pre-B cell, pre-B, early B cell stages independent of antigen receptor, and is associated with Src family protein tyrosine kinases, is tyrosine phosphorylated, inducing both intracellular calcium mobilization and inositol phospholipid signaling (Uckun F M, Burkhardt A L, Jarvis L, Jun X, Stealy B, Dibirdik I, Myers D E, Tuel-Ahlgren L, Bolen J B, 1983, J Biol Chem 268:21172-84). The key point of relevance for treatment of B cell malignancies is that CD19 is expressed in a tightly regulated manner on normal B cells, being restricted to early B cell precursors at the stage of IgH gene rearrangement, mature B cells, but not expressed on hematopoietic stem cells, or mature plasma cells (Anderson, K C, Bates, M P, Slaughenhout B L, Pinkus G S, Schlossman S F, Nadler L M, 1984, Blood 63:1424-1433).

The present standard of care for B-lineage leukemias may consists of remission induction treatment by high dose of chemotherapy or radiation, followed by consolidation, and may feature stem cell transplantation and additional courses of chemotherapy as needed (see the world wide web at cancer.gov). High toxicity associated with these treatments, as well as the risk of complications, such as relapse, secondary malignancy, or GVHD, motivate the search for better therapeutic alternatives. The expression of CD19 on both adult and pediatric (pre-B-ALL) B cell malignancies has led to exploiting this target for both antibody and chimeric antigen receptor (CAR)-T cell-based therapy (Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A, 2010, Blood 116:4099-102; Lee D W, Kochenderfer J N, Stetler-Stevenson M, Cui Y K, Delbrook C, Feldman S A, Orentas R, Sabatino M, Shah N N, Steinberg S M, Stroncek D, Tschernia N, Yuan C, Zhang H, Zhang L, Rosenberg S A, Wayne A S, Mackall C L, 2015, Lancet 385:517-28).

A number of novel approaches to treat B cell leukemia and lymphoma have been developed, including bi-specific antibodies that link an anti-CD19 binding motif to a T cell binding motif (i.e. Blinatumomab, Blincyto®) indicated for the treatment of Philadelphia chromosome-negative relapsed or refractory B-cell precursor acute lymphoblastic leukemia (ALL). To date, many of the binding moieties for CD19 employed in CAR constructs utilize a domain derived from murine antibodies. A number of these products are currently being considered for approval including those developed by Novartis and Kite Pharmaceuticals. In April of 2017 Novartis announced that CTL019 (tisagenlecleucel) received FDA breakthrough designation for treatment of adult patients with refractory or recurrent (r/r) DLBCL (diffuse large B cell lymphoma) who failed two or more prior therapies, adding this designation to that for r/r B-cell acute lymphoblastic leukemia (ALL). These indications were based on the Phase II JULIET study (NCT02445248) and the ELIANA study (NCT02435849), respectively. The JULIET trial showed and overall response rate (ORR) of 45%, with a 37% complete response (CR), and an 8% partial response (PR) at three months. In the ELIANA study, 82% of patients infused with the product achieved CR or CR with incomplete count recovery, and the relapse free survival rate at 6 months was 60%. The CAR-T product from Kite Pharmaceuticals (KTE-C19, axicabtagene ciloleucel) was granted breakthrough designation for diffuse large B-cell lymphoma (DLBLC), transformed follicular lymphoma (TFL), and primary mediastinal B-cell lymphoma (PMBCL). In the Kite ZUMA-3 phase II trial of KTE-C19 in r/r ALL, a 73% CR was reported (at 2 months or greater). All information is from company press releases. Whether antibody of CAR-T therapies are utilized, there are still a significant number of patients who are not helped by these therapies, and there is considerable room for improved therapeutic approaches.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after a single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18 (8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15 (18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22 (2):72-78.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1 (1):43-53; Kloss C C et al. Nat Biotechnol. 2013; 31 (1):71-5). A second challenge for the generation of a single ScFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21 (11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with chemical-based dimerizers, such as AP1903, demonstrates one way in which a powerful switch that can control T-cell populations can be initiated pharmacologically (Di Stasi A et al. N Engl J Med. 2011; 365 (18):1673-83). The creation of effector T-cell populations that are immune to the negative regulatory effects of transforming growth factor-β by the expression of a decoy receptor further demonstrates the degree to which effector T cells can be engineered for optimal antitumor activity (Foster A E et al. J Immunother. 2008; 31 (5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. This may be due in part to the murine origin of some of the CAR sequences employed.

The use of Blinotumomab (bi-specific anti-CD19 and anti-CD3 antibody) has shown impressive results for the gravely ill patients who have received this therapy. Nevertheless the durable remission rate is less than 40%, and at best only 50% of responders can be salvaged to hematopoietic stem cell transplant (HSCT) (see Gore et al., 2014, NCT01471782 and Von Stackelberg, et al., 2014, NCT01471782, summarized in: Benjamin, J E, Stein A S, 2016, Therapeutic Advances in Hematology 7:142-156). The requirement of patients who have received either bi-specific antibody or CAR-T therapy to subsequently undergo HSCT in order to maintain durable responses remains an area of active debate. Although high responses are reported for CD19 CAR-T trials, some even greater than 90%, if the trials are re-cast as "intent to treat" trials the number may be closer to 70% (Davis K L, Mackall C L, 2016, Blood Advances 1:265-268). The best results at 12 months post-CAR19 treatment reported show a RFS of 55% and and OS of 79% in patients who were able to receive the T cell product at the University of Pennsylvania (Maude S L, Teachey D T, Rheingold S R, Shaw P A, Aplenc R, Barrett D M, Barker C S, Callahan C, Frey N V, Farzana N, Lacey S F, Zheng A, Levine B, Melenhorst J J, Motley L, Prter D L, June C H, Grupp S A, 2016, J Clin Oncol 34, no15_suppl (May 2016) 3011-3011).

Accordingly, there is an urgent and long felt need in the art for discovering novel compositions and methods for treatment of B-ALL and other CD19-expressing B cell malignancies using an approach that can exhibit specific and efficacious anti-tumor effect without the aforementioned short comings.

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of CD19 and which CARs contain CD19 antigen binding domains that exhibit a high surface expression on transduced T cells, exhibit a high degree of cytolysis of CD19-expressing cells, and in which the transduced T cells demonstrate in vivo expansion and persistence.

SUMMARY

Novel anti-CD19 antibodies or antigen binding domains thereof and chimeric antigen receptors (CARs) that contain such CD19 antigen binding domains are provided herein, as well as host cells (e.g., T cells) expressing the receptors, and nucleic acid molecules encoding the receptors. The CARs exhibit a high surface expression on transduced T cells, with a high degree of cytolysis, and with transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD19 antibody or a fragment thereof is provided comprising a nucleic acid sequence selected from the group consisting of SEQ ID NOs: 1, 3, 5, 7, 9, 11, 13, and 15.

In one embodiment, an isolated polynucleotide encoding a fully human anti-CD19 antibody or a fragment thereof is provided, wherein the antibody or a fragment thereof comprises a fragment selected from the group consisting of an Fab fragment, an F(ab')$_2$ fragment, an Fv fragment, and a single chain Fv (ScFv).

In one embodiment, an isolated polynucleotide encoding a fully human anti-CD19 antibody or a fragment thereof is provided, wherein the antibody or a fragment thereof comprises an amino acid sequence selected from the group consisting of SEQ ID NOs: 2, 4, 6, 8, 10, 12, 14, and 16.

In one aspect, an isolated nucleic acid molecule encoding a chimeric antigen receptor (CAR) is provided comprising, from N-terminus to C-terminus, at least one CD19 antigen binding domain encoded by a nucleotide sequence comprising a nucleic acid sequence selected from the group consisting of SEQ ID NOs: 1, 3, 5, 7, 9, 11, 13, and 15, at least one transmembrane domain, and at least one intracellular signaling domain.

In one embodiment, an isolated nucleic acid molecule encoding the CAR is provided wherein the encoded extracellular CD19 antigen binding domain comprises at least one single chain variable fragment of an antibody that binds to CD19.

In another embodiment, an isolated nucleic acid molecule encoding the CAR is provided wherein the encoded extracellular CD19 antigen binding domain comprises at least one heavy chain variable region of an antibody that binds to CD19.

In yet another embodiment, an isolated nucleic acid molecule encoding the CAR is provided wherein the encoded CAR extracellular CD19 antigen binding domain further comprises at least one lipocalin-based antigen binding antigen (anticalins) that binds to CD19.

In one embodiment, an isolated nucleic acid molecule is provided wherein the encoded extracellular CD19 antigen binding domain is connected to the transmembrane domain by a linker domain.

In another embodiment, an isolated nucleic acid molecule encoding the CAR is provided wherein the encoded CD19 extracellular antigen binding domain is preceded by a sequence encoding a leader or signal peptide.

In yet another embodiment, an isolated nucleic acid molecule encoding the CAR is provided comprising at least one CD19 antigen binding domain encoded by a nucleotide sequence comprising a nucleic acid sequence selected from the group consisting of SEQ ID NOs: 1, 3, 5, 7, 9, 11, 13 and 15 and wherein the CAR additionally encodes an extracellular antigen binding domain targets an antigen that includes, but is not limited to, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, TSLPR, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD19 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on the N-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 17.

In yet another embodiment, an isolated nucleic acid molecule encoding the CAR is provided wherein the encoded leader sequence comprises the amino acid sequence of SEQ ID NO: 18.

In one aspect, a chimeric antigen receptor (CAR) is provided herein comprising, from N-terminus to C-terminus, at least one CD19 antigen binding domain, at least one transmembrane domain, and at least one intracellular signaling domain.

In one embodiment, a CAR is provided wherein the extracellular CD19 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising CD20, CD22, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, TSLPR, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, anti-TSLPR ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 19 (LTG 2050 LP-M19217-CD8 TM-41BB-CD3 zeta CAR nucleic acid sequence (FIG. 2A)). In one embodiment, the nucleic acid sequence encodes a CAR comprising the amino acid sequence of SEQ ID NO: 20 (LTG 2050 LP-M19217-CD8 TM-41BB-CD3 zeta CAR amino acid sequence (FIG. 2A)).

In another embodiment, the nucleic acid sequence encoding a CAR comprises the nucleic acid sequence of SEQ ID NO: 21 (LTG 2065 LP-M19217-1-CD8 TM-41BB-CD3 zeta CAR nucleic acid sequence (FIG. 2B)). In one embodiment, the nucleic acid sequence encodes a CAR comprising the amino acid sequence of SEQ ID NO: 22 (LTG 2065 LP-M19217-1-CD8 TM-41BB-CD3 zeta CAR amino acid sequence (FIG. 2B)).

In another embodiment, the nucleic acid sequence encoding a CAR comprises the nucleic acid sequence of SEQ ID NO: 23 (LTG2066 LP-M19217-2-CD8 TM-41BB-CD3 zeta CAR nucleotide sequence (FIG. 2C)). In one embodiment, the nucleic acid sequence encodes a CAR comprising the amino acid sequence of SEQ ID NO: 24 (LTG 2066 LP-M19217-2-CD8 TM-41BB-CD3 zeta CAR amino acid sequence (FIG. 2C)).

In another embodiment, the nucleic acid sequence encoding a CAR comprises the nucleic acid sequence of SEQ ID NO: 25 (LTG 2067 LP-M19217-7-CD8 TM-41BB-CD3 zeta CAR nucleic acid sequence (FIG. 2D)). In one embodiment, the nucleic acid sequence encodes a CAR comprising the amino acid sequence of SEQ ID NO: 26 (LTG 2067 LP-M19217-7-CD8 TM-41BB-CD3 zeta CAR amino acid sequence (FIG. 2D)).

In another embodiment, the nucleic acid sequence encoding a CAR comprises the nucleic acid sequence of SEQ ID NO: 27 (LTG 2068 LP-M19217-23-CD8 TM-41BB-CD3 zeta CAR nucleic acid sequence (FIG. 2E)). In one embodiment, the nucleic acid sequence encodes a CAR comprising the amino acid sequence of SEQ ID NO: 28 LTG2068 LP-M19217-23-CD8 TM-41BB-CD3 zeta CAR amino acid sequence (FIG. 2E)).

In another embodiment, the nucleic acid sequence encoding a CAR comprises the nucleic acid sequence of SEQ ID NO: 29 (LTG 2069 LP-M19217-29-CD8 TM-41BB-CD3 zeta CAR nucleic acid sequence (FIG. 2F)). In one embodiment, the nucleic acid sequence encodes a CAR comprising the amino acid sequence of SEQ ID NO: 30 (LTG 2069 LP-M19217-29-CD8 TM-41BB-CD3 zeta CAR amino acid sequence (FIG. 2F)).

In another embodiment, the nucleic acid sequence encoding a CAR comprises the nucleic acid sequence of SEQ ID NO: 31 (LTG 2070 LP-M19217-38-CD8 TM-41BB-CD3 zeta CAR nucleic acid sequence (FIG. 2G)). In one embodiment, the nucleic acid sequence encodes a CAR comprising the amino acid sequence of SEQ ID NO: 32 (LTG 2070 LP-M19217-38-CD8 TM-41BB-CD3 zeta CAR amino acid sequence (FIG. 2G)).

In another embodiment, the nucleic acid sequence encoding a CAR comprises the nucleic acid sequence of SEQ ID NO: 33 (LTG 2071 LP-M19217-40-CD8 TM-41BB-CD3 zeta CAR nucleic acid sequence (FIG. 2H)). In one embodiment, the nucleic acid sequence encodes a CAR comprising the amino acid sequence of SEQ ID NO: 34 (LTG 2071 LP-M19217-40-CD8 TM-41BB-CD3 zeta CAR amino acid sequence (FIG. 2H)).

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a human CD19 antigen binding domain comprising the amino acid sequence of SEQ ID NO. 2, 4, 6, 8, 10, 12, 14, or 16, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human cancer includes an adult carcinoma comprising coral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD19, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR-expressing cell.

In yet another aspect, a method for diagnosing a disease, disorder or condition associated with the expression of CD19 on a cell, is provided comprising a) contacting the cell with a human anti-CD19 antibody or fragment thereof, wherein the antibody or a fragment thereof comprises an amino acid sequence selected from the group consisting of SEQ ID NOs: 2, 4, 6, 8, 10, 12, 14, 16; and b) detecting the presence of CD19 wherein the presence of CD19 diagnoses for the disease, disorder or condition associated with the expression of CD19.

In one embodiment, the disease, disorder or condition associated with the expression of CD19 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD19-related disease in a mammal, is provided comprising detecting the expression of CD19 in a sample derived from the mammal comprising: a) contacting the sample with a human anti-CD19 antibody or fragment thereof, wherein the antibody or a fragment thereof comprises an amino acid sequence selected from the group consisting of SEQ ID NOs: 2, 4, 6, 8, 10, 12, 14, or 16; and b) detecting the presence of CD19 wherein the presence of CD19 diagnoses for a CD19-related disease in the mammal.

In another embodiment, a method of inhibiting CD19-dependent T cell inhibition, is provided comprising contacting a cell with a human anti-CD19 antibody or fragment thereof, wherein the antibody or a fragment thereof comprises an amino acid sequence selected from the group consisting of SEQ ID NOs: 2, 4, 6, 8, 10, 12, 14, or 16. In one embodiment, the cell is selected from the group consisting of a CD19-expressing tumor cell, a tumor-associated macrophage, and any combination thereof.

In another embodiment, a method of blocking T-cell inhibition mediated by a CD19-expressing cell and altering the tumor microenvironment to inhibit tumor growth in a mammal, is provided comprising administering to the mammal an effective amount of a composition comprising an isolated anti-CD19 antibody or fragment thereof, wherein the antibody or a fragment thereof comprises an amino acid sequence selected from the group consisting of SEQ ID NOs: 2, 4, 6, 8, 10, 12, 14, and 16. In one embodiment, the cell is selected from the group consisting of a CD19-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD19 antibody or fragment thereof, wherein the antibody or a fragment thereof comprises an amino acid sequence selected from the group consisting of SEQ ID NOs: 2, 4, 6, 8, 10, 12, 14 and 16. In one embodiment, the antibody or fragment thereof inhibits the interaction between a first cell with a T cell, wherein the first cell is selected from the group consisting of a CD19-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD19 and/or one or more of the aforementioned antigens, under conditions sufficient to form an immune complex of the antigen binding domain on the CAR and the extracellular domain of CD19 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD19 antigen binding domain comprising the amino acid sequence of SEQ ID NOs. 2, 4, 6, 8, 10, 12, 14, or 16, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one CD19 antigen binding domain comprising the amino acid sequence of SEQ ID NOs. 2, 4, 6, 8, 10, 12, 14, or 16, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD19 antigen binding domain comprising the amino acid sequence of SEQ ID NOs. 2, 4, 6, 8, 10, 12, 14, or 16, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIGS. 2A-2H depict nucleic acid and amino acid sequences of several chimeric antigen receptors (CARs) containing novel human extracellular CD19 antigen binding domain sequences. The general scheme for the CARs includes, from the N terminus to the C terminus, a Signal peptide, a human anti-CD19 binder single chain fragment variable (ScFv), an extracellular linker, a transmembrane domain, a 4-1BB (CD137) signaling domain, and a CD3 zeta signaling domain.

FIG. 2A depicts a lentiviral vector expressing the CAR LTG2050 (19217 ScFv-CD8 TM-41BB-CD3 zeta) nucleic acid sequence (SEQ ID NO: 19) and the encoded amino acid sequence (SEQ ID NO: 20).

FIG. 2B depicts a lentiviral vector expressing the CAR LTG2065 (M19217-1 ScFv-CD8 TM-41BB-CD3 zeta) nucleic acid sequence (SEQ ID NO: 21) and the encoded amino acid sequence (SEQ ID NO: 22).

FIG. 2C depicts a lentiviral vector expressing the CAR LTG2066 (M19217-2 ScFv CD8 TM-41BB-CD3 zeta) nucleotide sequence (SEQ ID NO: 23) and the encoded amino acid sequence (SEQ ID NO: 24).

FIG. 2D depicts a lentiviral vector expressing the CAR LTG2067 (M19217-7 ScFv CD8 TM-41BB-CD3 zeta) nucleic acid sequence (SEQ ID NO: 25) and the encoded amino acid sequence (SEQ ID NO: 26).

FIG. 2E depicts a lentiviral vector expressing the CAR LTG2068 (M19217-23 ScFv CD8 TM-41BB-CD3 zeta) nucleic acid sequence (SEQ ID NO: 27) and the encoded amino acid sequence (SEQ ID NO: 28).

FIG. 2F depicts a lentiviral vector expressing the CAR LTG2069 (M19217-29 ScFv CD8 TM-41BB-CD3 zeta) nucleic acid sequence (SEQ ID NO: 29) and the encoded amino acid sequence (SEQ ID NO: 30).

FIG. 2G depicts a lentiviral vector expressing the CAR LTG2070 (M19217-38 ScFv CD8 TM-41BB-CD3 zeta) nucleic acid sequence (SEQ ID NO: 31) and the encoded amino acid sequence (SEQ ID NO: 32).

FIG. 2H depicts a lentiviral vector expressing the CAR LTG2071 (M19217-40 ScFv CD8 TM-41BB-CD3 zeta) nucleic acid sequence (SEQ ID NO: 33) and the encoded amino acid sequence (SEQ ID NO: 34).

DETAILED DESCRIPTION

Definitions

Figure 1:
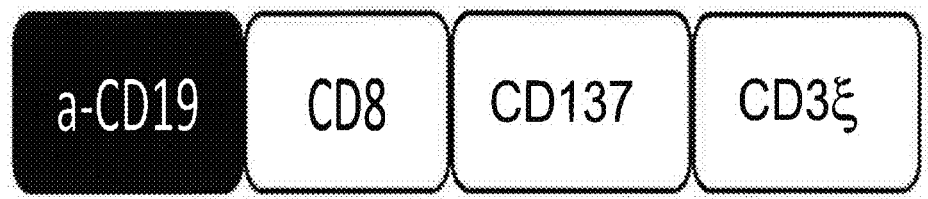
FIG. 1 depicts a schematic of the general domain structure of CARs with novel extracellular CD19 antigen binding domain sequences. A chimeric antigen receptor is composed of an extracellular CD19-binding ScFv domain, a CD8 spacer and transmembrane domain, an intracellular signaling CD137 costimulatory domain and CD3 z signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−.20% or in some instances .+−.10%, or in some instances .+−.5%, or in some instances .+−.1%, or in some instances .+−.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnol-*

*ogy: a Comprehensive Desk Reference*, published by VCH Publishers, Inc., 1995; and other similar references.

The present disclosure provides for CD19 antibodies or fragments thereof as well as chimeric antigen receptors (CARs) having such CD19 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

In light of this discovery, a series of CD19 binders from a human scFv expression library have been developed. These fully-human CD19 CARs are less likely to induce an allergic or rejection response by the patient as they are no longer of murine origin (see Maus M V, Haas A R, Beatty G L, Albeda S M, Levine B L, Liu X, Zhao Y, Kalos M, June C H, 2013, Cancer Immunology Research, 1:26-31). Thus, when these "fully human" CARs are expressed in T cells and then infused into patients, they are likely to be more therapeutically effective. These human sequence-derived CAR binders may be used for the treatment of human cancer, leukemias, and lymphomas that express the CD19 antigen, including; but not limited to, B-ALL, DLBCL, FL.

The CARs disclosed herein are expressed at a high level in a cell. A cell expressing the CAR has a high in vivo proliferation rate, produces large amounts of cytokines, and has a high cytotoxic activity against a cell having, on its surface, a CD19 antigen to which a CAR binds. The use of a human extracellular CD19 antigen-binding domain results in generation of a CAR that functions better in vivo, while avoiding the induction of anti-CAR immunity in the host immune response and the killing of the CAR T cell population. The CARs expressing the entirely human extracellular CD19 ScFv antigen-binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD19. This latter property allows investigators to better tune efficacy vs toxicity, and/or tissue specificity of the CAR T product, since lower-affinity binders may have higher specificity to tumors vs normal tissues due to higher expression of CD19 on tumors than normal tissue, which may prevent on-target off tumor toxicity and bystander cell killing.

What follows is a detailed description of the inventive CARs including a description of their extracellular CD19 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD19 antigen binding domain capable of binding to CD19, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD19. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, BCMA, ROR1, and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD19 and the tumors associated with expression of CD19 comprise lung mesothelioma, ovarian, and pancreatic cancers that express high levels of the extracellular protein CD19, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, CD38, CD123, CD138, BCMA, c-Met, PSMA, Glycolipid F77, EGFRvIII, GD-2, FGFR4, TSLPR, NY-ESO-1 TCR, MAGE A3 TCR, and the like.

In a preferred embodiment, the antigen binding domain portion of the CAR targets the extracellular CD19 antigen.

In one preferred embodiment, the isolated nucleic acid molecule encoding the extracellular CD19 VH-2 antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular CD19 VH-2 antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular CD19 VH-4 antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular CD19 VH-4 antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular CD19 ScFv 9 antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular CD19 ScFv 9 antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the extracellular CD19 ScFv 10 antigen binding domain comprises a nucleotide sequence of SEQ ID NO: 7, or a sequence with 85%, 90%, 95%, 96%, 97%, 98% or 99% identity thereof. In one embodiment, an isolated nucleic acid molecule is provided wherein the encoded extracellular CD19 ScFv 10 antigen binding domain comprises an amino acid sequence of SEQ ID NO: 8, or an amino acid sequence with 85%, 90%, 95%, 96%, 97%, 98% or 99% identity to an amino acid sequence of SEQ ID NO: 8.

In one preferred embodiment, the isolated nucleic acid molecule encoding the extracellular CD19 ScFv 12 antigen binding domain comprises a nucleotide sequence of SEQ ID NO: 9, or a sequence with 85%, 90%, 95%, 96%, 97%, 98% or 99% identity thereof. In one embodiment, an isolated nucleic acid molecule is provided wherein the encoded extracellular CD19 ScFv 12 antigen binding domain comprises an amino acid sequence of SEQ ID NO: 10, or an amino acid sequence with 85%, 90%, 95%, 96%, 97%, 98% or 99% identity to an amino acid sequence of SEQ ID NO: 10.

In one preferred embodiment, the isolated nucleic acid molecule encoding the extracellular CD19 ScFv 15 antigen binding domain comprises a nucleotide sequence of SEQ ID NO: 11, or a sequence with 85%, 90%, 95%, 96%, 97%, 98% or 99% identity thereof. In one embodiment, an isolated nucleic acid molecule is provided wherein the encoded extracellular CD19 ScFv 15 antigen binding domain comprises an amino acid sequence of SEQ ID NO: 12, or an amino acid sequence with 85%, 90%, 95%, 96%, 97%, 98% or 99% identity to an amino acid sequence of SEQ ID NO: 12.

In one preferred embodiment, the isolated nucleic acid molecule encoding the extracellular CD19 ScFv 15 antigen binding domain comprises a nucleotide sequence of SEQ ID NO: 13, or a sequence with 85%, 90%, 95%, 96%, 97%, 98% or 99% identity thereof. In one embodiment, an isolated nucleic acid molecule is provided wherein the encoded extracellular CD19 ScFv 15 antigen binding domain comprises an amino acid sequence of SEQ ID NO: 14, or an amino acid sequence with 85%, 90%, 95%, 96%, 97%, 98% or 99% identity to an amino acid sequence of SEQ ID NO: 14.

In one preferred embodiment, the isolated nucleic acid molecule encoding the extracellular CD19 ScFv 15 antigen binding domain comprises a nucleotide sequence of SEQ ID NO: 15, or a sequence with 85%, 90%, 95%, 96%, 97%, 98% or 99% identity thereof. In one embodiment, an isolated nucleic acid molecule is provided wherein the encoded extracellular CD19 ScFv 15 antigen binding domain comprises an amino acid sequence of SEQ ID NO: 16, or an amino acid sequence with 85%, 90%, 95%, 96%, 97%, 98% or 99% identity to an amino acid sequence of SEQ ID NO: 16.

In the various embodiments of the CD19-specific CARs disclosed herein, the general scheme is set forth in FIG. 1 and includes, from the N-terminus to the C-terminus, a signal or leader peptide, anti-CD19 ScFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 19, and encodes the CAR comprising the amino acid sequence as set forth in SEQ ID NO: 20 [LTG 2050 LP-M19217-CD8 TM-41BB-CD3 zeta amino acid sequence (as depicted in FIG. 2A)].

In one embodiment, the nucleic acid sequence encoding a CAR comprises the nucleic acid sequence of SEQ ID NO: 19, or a sequence with 85%, 90%, 95%, 96%, 97%, 98% or 99% identity thereof, and encodes the CAR comprising the amino acid sequence as set forth in SEQ ID NO: 20 or a sequence with 85%, 90%, 95%, 96%, 97%, 98% or 99% identity thereof LTG 2050 LP-M19217-CD8 TM-41BB-CD3 zeta amino acid sequence (as depicted in FIG. 2A)].

In another embodiment, the nucleic acid sequence encoding a CAR comprises the nucleic acid sequence of SEQ ID NO: 21, and encodes the CAR comprising the amino acid sequence as set forth in SEQ ID NO: 22 [LTG 2065 LP-M19217-1-CD8 TM-41BB-CD3 zeta amino acid sequence (as depicted in FIG. 2B)].

In another embodiment, the nucleic acid sequence encoding a CAR comprises the nucleic acid sequence of SEQ ID NO: 21 or a sequence with 85%, 90%, 95%, 96%, 97%, 98% or 99% identity thereof, and encodes the CAR comprising the amino acid sequence as set forth in SEQ ID NO: 22 or a sequence with 85%, 90%, 95%, 96%, 97%, 98% or 99% identity thereof [LTG 2065 LP-M19217-1-CD8 TM-41BB-CD3 zeta amino acid sequence (as depicted in FIG. 2B)].

In another embodiment, the nucleic acid sequence encoding a CAR comprises the nucleic acid sequence of SEQ ID NO: 23, and encodes the CAR comprising the amino acid sequence as set forth in SEQ ID NO: 24 LTG 2066 LP-M19217-2-CD8 TM-41BB-CD3 zeta CAR amino acid sequence (as depicted in FIG. 2C)].

In another embodiment, the nucleic acid sequence encoding a CAR comprises the nucleic acid sequence of SEQ ID NO: 23 or a sequence with 85%, 90%, 95%, 96%, 97%, 98% or 99% identity thereof, and encodes the CAR comprising the amino acid sequence as set forth in SEQ ID NO: 24 or a sequence with 85%, 90%, 95%, 96%, 97%, 98% or 99% identity thereof [LTG 2066 LP-M19217-2-CD8 TM-41BB-CD3 zeta CAR amino acid sequence (as depicted in FIG. 2C)].

In yet another embodiment, the nucleic acid sequence encoding a CAR comprises the nucleic acid sequence of SEQ ID NO: 25, and encodes the CAR comprising the amino acid sequence as set forth in SEQ ID NO: 26 [LTG2067 LP-M19217-7-CD8 TM-41BB-CD3 zeta amino acid sequence (as depicted in FIG. 2D)].

In yet another embodiment, the nucleic acid sequence encoding a CAR comprises the nucleic acid sequence of SEQ ID NO: 25 or a sequence with 85%, 90%, 95%, 96%, 97%, 98% or 99% identity thereof, and encodes the CAR comprising the amino acid sequence as set forth in SEQ ID NO: 26 or a sequence with 85%, 90%, 95%, 96%, 97%, 98% or 99% identity thereof [LTG2067 LP-M19217-7-CD8 TM-41BB-CD3 amino acid sequence (as depicted in FIG. 2D)].

In yet another embodiment, the nucleic acid sequence encoding a CAR comprises the nucleic acid sequence of SEQ ID NO: 27, and encodes the CAR comprising the amino acid sequence as set forth in SEQ ID NO: 28 [LTG2068 LP-M19217-23-CD8 TM-41BB-CD3 zeta amino acid sequence (as depicted in FIG. 2E)].

In yet another embodiment, the nucleic acid sequence encoding a CAR comprises the nucleic acid sequence of SEQ ID NO: 27 or a sequence with 85%, 90%, 95%, 96%, 97%, 98% or 99% identity thereof, and encodes the CAR comprising the amino acid sequence as set forth in SEQ ID NO: 28 or a sequence with 85%, 90%, 95%, 96%, 97%, 98% or 99% identity thereof [LTG2068 LP-M19217-23-CD8 TM-41BB-CD3 zeta amino acid sequence (as depicted in FIG. 2E)].

In yet another embodiment, the nucleic acid sequence encoding a CAR comprises the nucleic acid sequence of SEQ ID NO: 29, and encodes the CAR comprising the amino acid sequence as set forth in SEQ ID NO: 30 [(LTG2069 LP-M19217-29-CD8 TM-41BB-CD3 zeta amino acid sequence (as depicted in FIG. 2F)].

In yet another embodiment, the nucleic acid sequence encoding a CAR comprises the nucleic acid sequence of SEQ ID NO: 29 or a sequence with 85%, 90%, 95%, 96%, 97%, 98% or 99% identity thereof, and encodes the CAR comprising the amino acid sequence as set forth in SEQ ID NO: 30 or a sequence with 85%, 90%, 95%, 96%, 97%, 98% or 99% identity thereof [LTG2069 LP-M19217-29-CD8 TM-41BB-CD3 zeta amino acid sequence (as depicted in FIG. 2F)].

In yet another embodiment, the nucleic acid sequence encoding a CAR comprises the nucleic acid sequence of SEQ ID NO: 31, and encodes the CAR comprising the amino acid sequence as set forth in SEQ ID NO: 32 [(LTG2070 LP-M19217-38-CD8 TM-41BB-CD3 zeta amino acid sequence (as depicted in FIG. 2G)].

In yet another embodiment, the nucleic acid sequence encoding a CAR comprises the nucleic acid sequence of SEQ ID NO: 31 or a sequence with 85%, 90%, 95%, 96%, 97%, 98% or 99% identity thereof, and encodes the CAR comprising the amino acid sequence as set forth in SEQ ID NO: 32 or a sequence with 85%, 90%, 95%, 96%, 97%, 98% or 99% identity thereof [(LTG2070 LP-M19217-38-CD8 TM-41BB-CD3 zeta amino acid sequence (as depicted in FIG. 2G)].

In yet another embodiment, the nucleic acid sequence encoding a CAR comprises the nucleic acid sequence of SEQ ID NO: 33, and encodes the CAR comprising the amino acid sequence as set forth in SEQ ID NO: 34 [(LTG2071 LP-M19217-40-CD8 TM-41BB-CD3 zeta amino acid sequence (as depicted in FIG. 2H)].

In yet another embodiment, the nucleic acid sequence encoding a CAR comprises the nucleic acid sequence of SEQ ID NO: 33 or a sequence with 85%, 90%, 95%, 96%, 97%, 98% or 99% identity thereof, and encodes the CAR comprising the amino acid sequence as set forth in SEQ ID NO: 34 or a sequence with 85%, 90%, 95%, 96%, 97%, 98% or 99% identity thereof [(LTG2071 LP-M19217-40-CD8 TM-41BB-CD3 zeta amino acid sequence (as depicted in FIG. 2H)].

Figure 3:
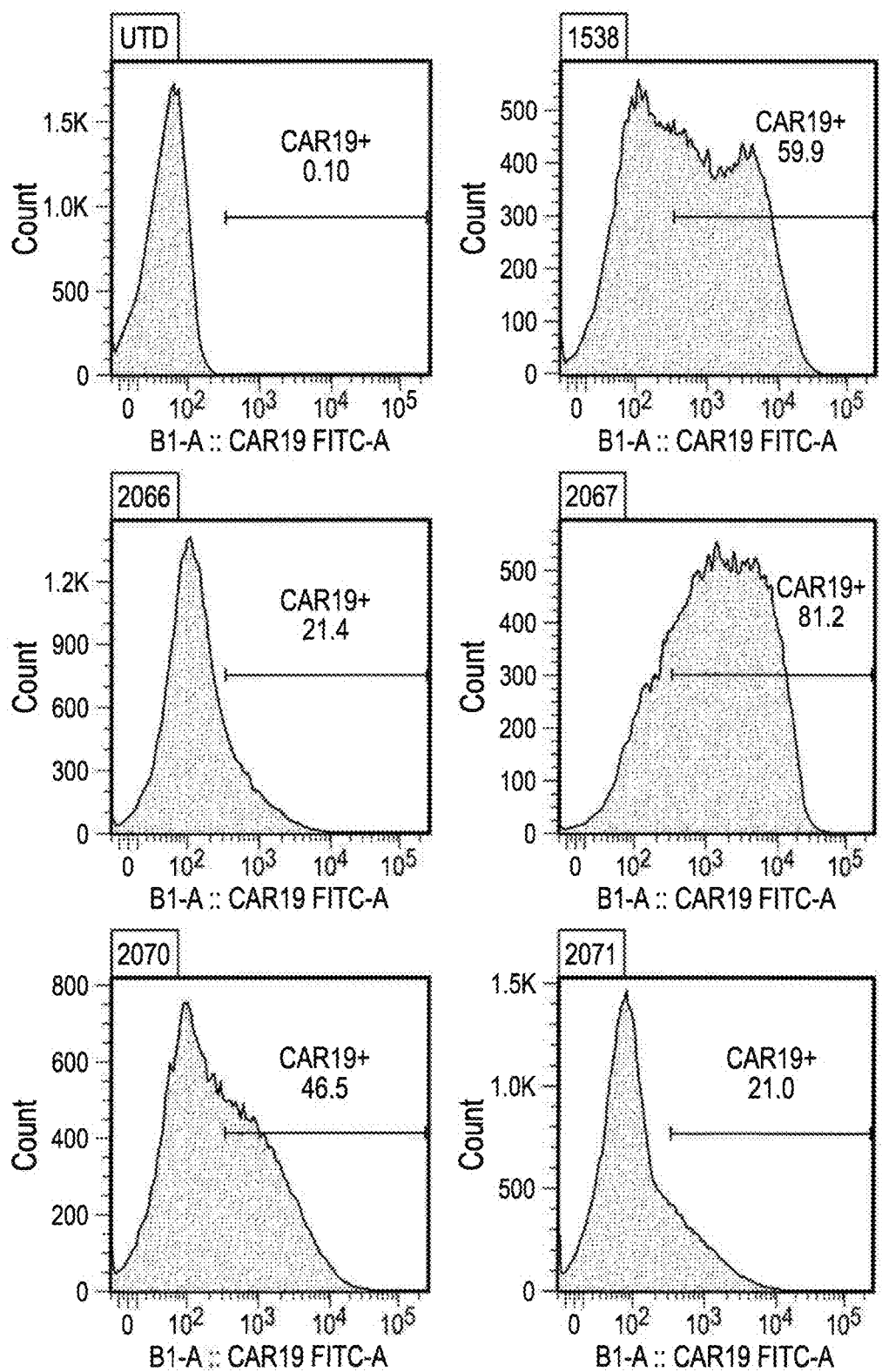
FIG. 3 depicts anti-CD19 CAR surface expression in primary human T cells. CAR T cells redirected to CD19 tumor antigen via the use of ScFv domains (as listed in each panel) were generated by lentiviral transduction with CAR expression constructs. CART detection was performed by flow cytometry. T cells were washed twice in cold PBS-EDTA buffer and stained with CD19-Fc peptide followed by anti Fc-AF647 reagent. At least 20,000 cells were acquired for each analysis. Cells were gated based on forward scatter and side scatter, singlet discrimination, and 7AAD negativity so that only viable cells were analyzed. Data were acquired on MACSQuant 10 flow cytometer in the APC channel. UTD, un-transduced negative control cells. The marker in each panel identifies the CAR-expressing population, and are listed as percent of total transduced T cells analyzed.
Figure 3:
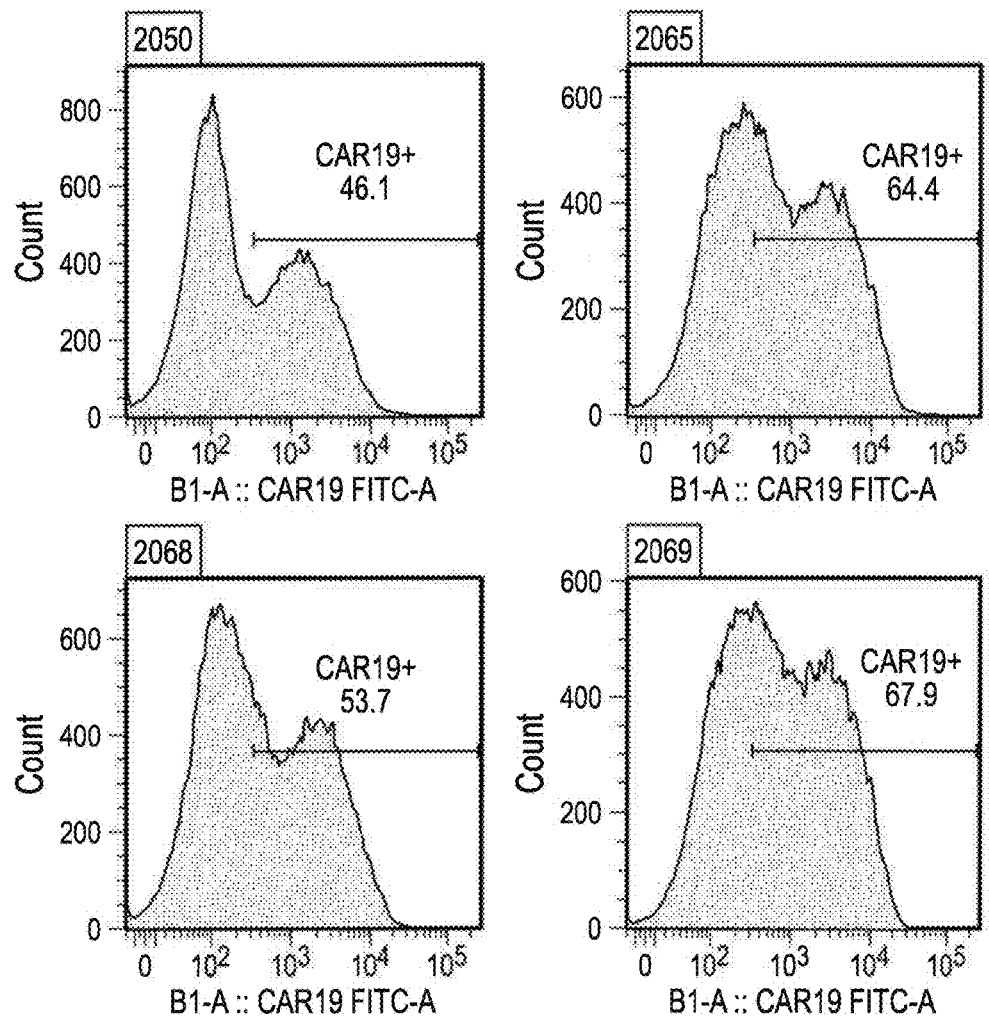

The surface expression of anti-CD19 CARs incorporating single chain fragment variable (ScFv) sequences reactive with CD19 antigen, is shown in Example 2 infra and summarized in Table 2. The expression level for each ScFv- or VH-containing CAR was determined by flow cytometric analysis of LV-transduced T cells from healthy donors using a recombinant CD19-Fc peptide, followed by anti-human Fc F(ab')2 fragment conjugated to AF647, and detected in the APC channel, (c.f., FIG. 3). The ScFv-based anti-CD19 CAR constructs LTG2050, LTG2065-LTG2071 were highly expressed in human primary T cells (as indicated by the gated population) as compared to non-transduced T cell controls (non-gated cell population). Representative results from one donor are shown.

Figure 4:
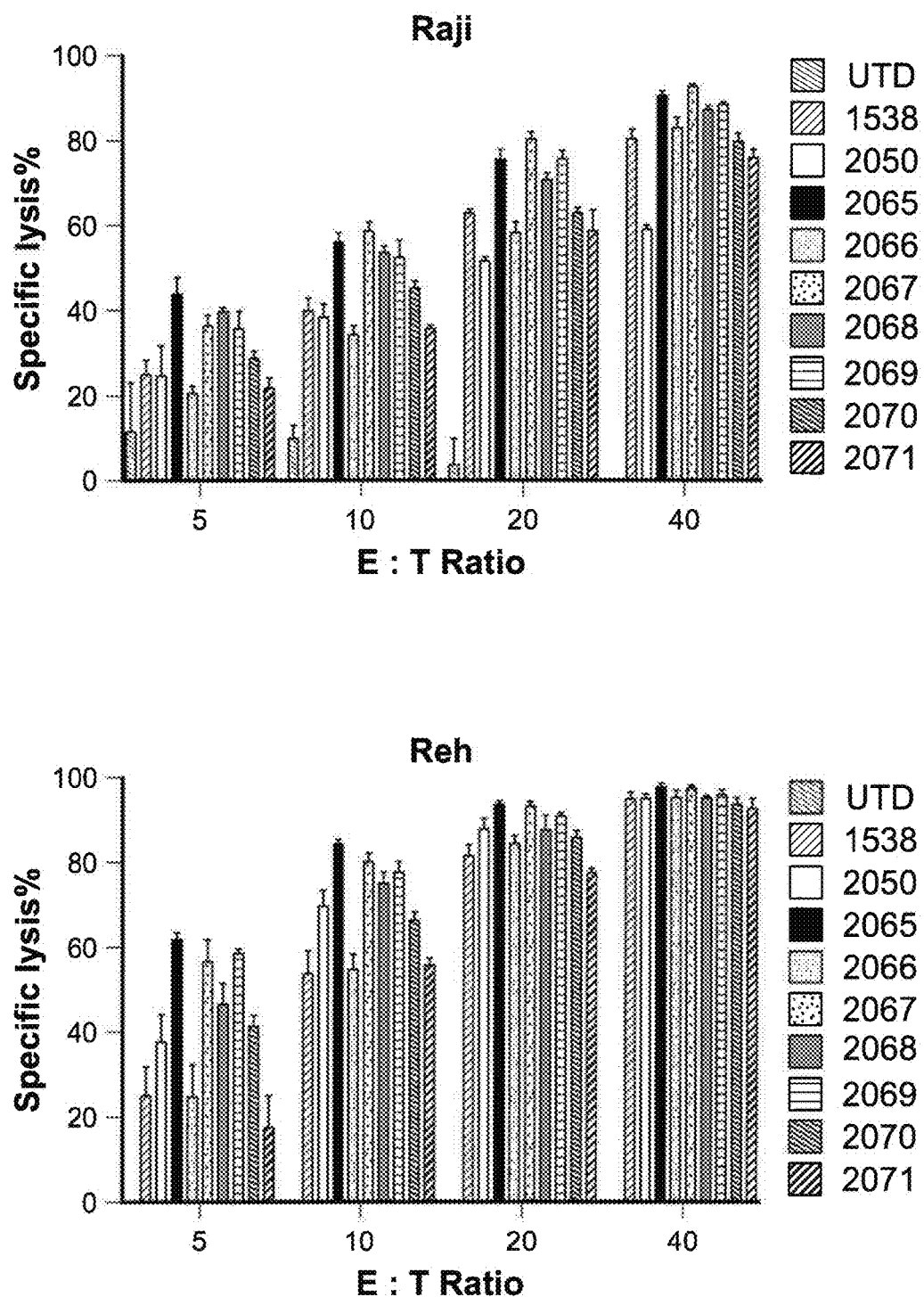
FIG. 4 depicts anti CD19 CAR T cells incorporating ScFv binders (LTG2050, 2065-2071) mediating cytolysis of CD19-positive tumors in vitro. CAR T cells expressing anti-CD19 constructs were incubated with CD19-positive cell lines (Raji and Reh), or CD19-negative lines (K562 and 293T) that were stably transduced with firefly luciferase, at effector to target ratio of 5, 10, 20, and 40 (x-axis) overnight. Then, CART cytotoxic activity was assessed by luciferase activity measurement as described in the Materials and Methods. Each bar is the mean of 3 technical replicates and error bars represent SD. UTD—untransduced T cell negative control, 1538-LTG1538 FMC63 murine anti-CD19 CAR positive control.
Figure 4:
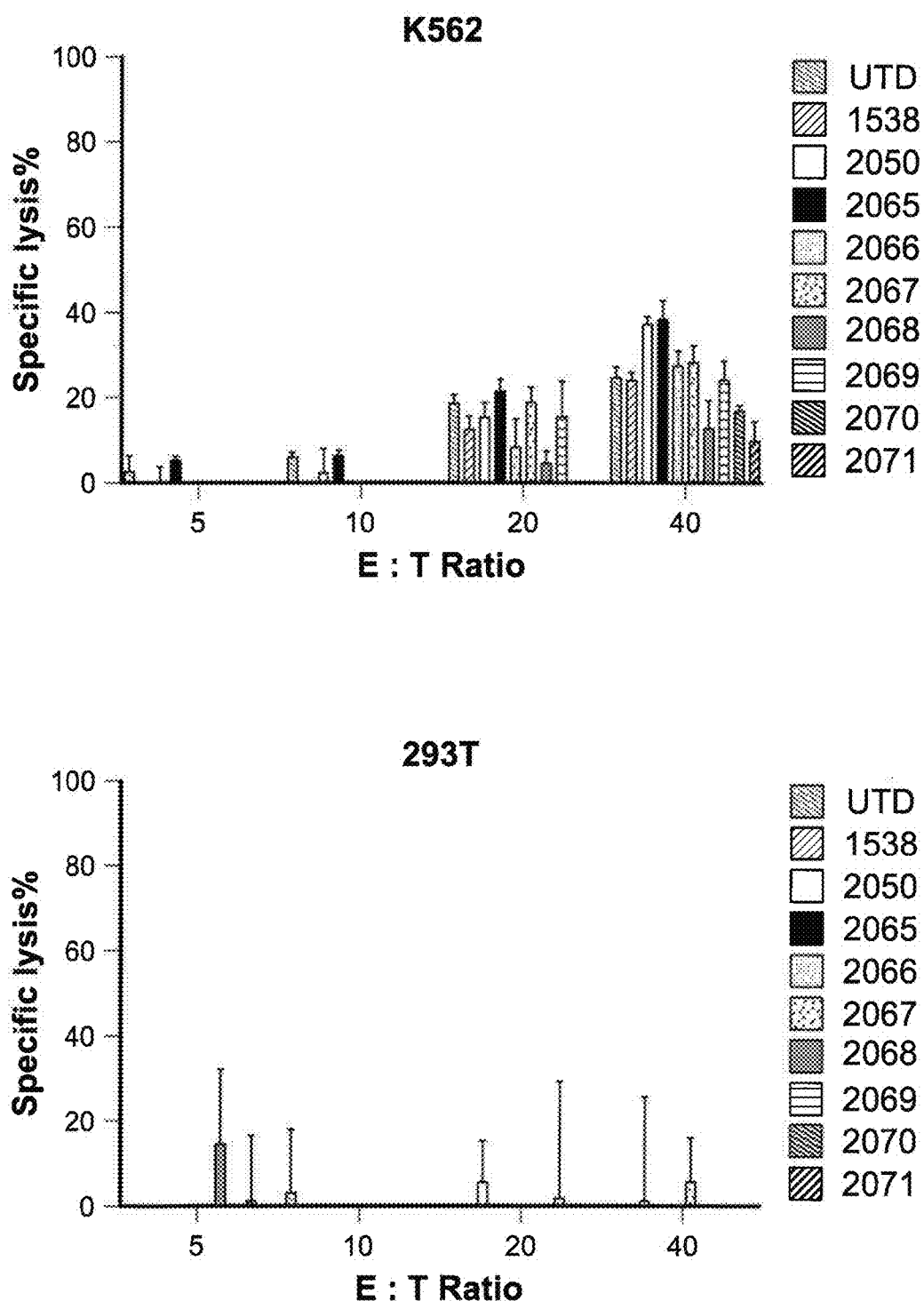

As shown in Example 2 and FIG. 4, high cytolytic activity of the CD19 CARs was demonstrated when lentiviral vectors (LV) expressing the following CARs were created and tested for anti-leukemia activity. Each experimental CAR contains the 4-1BB/CD3-zeta chain signaling motif and the specific anti-CD19 binding motif/domain noted therein. Leukemia target lines with varying CD19 surface expression were used: Raji and Reh; and CD19 negative K562 and 293T. ScFv-based anti-CD19 CAR constructs LTG2050 and LTG2065-2071 were able to efficiently lyse CD19-high tumor lines Raji and Reh, whereas they had no specific lytic activity against K562 or 293T, (cf., FIG. 4). These results demonstrate the efficiency and specificity of the generated CAR constructs.

The capacity of anti-CD19 CAR T cells for cytokine secretion was then evaluated. Tumor cells were co-incubated with CAR T cells or control T cells at effector to target ratio of 10:1 overnight, and culture supernatants were analyzed by ELISA for IFN gamma, TNF alpha and IL-2 (cf., FIG. 5). Of note, CAR T-expressing cells LTG2065, LTG2066, LTG2067, LTG2068, LTG2069, LTG2070, and LTG2071 elaborated high levels of IFN gamma, TNF alpha and IL-2, whereas the negative control (untransduced, UN) yielded no appreciable cytokine induction. Surprisingly, CD19 CAR LTG2050 yielded significantly lower levels of induced cytokines against tumor lines tested. The CAR that was tested as a positive control, LTG1538, which expressed the murine FMC63 CD19 binder (SEQ ID NO: 47), had lower activity than all binders tested except for LTG2050. The high vitro cytolytic function of LTG2050, which had low cytokine production ability, suggests that multiple CAR T functional endpoints need to be tested on construct by construct basis. Moreover, the superiority of the LTG2065-2071 human CD19 binders to the murine FMC63 scFv was clearly demonstrated in the cytokine production assays.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular human CD19 ScFv antigen binding domains, other nucleotide and/or amino acid variants within the CD19 variable ScFv antigen binding domains may be used to derive heavy-chain only binding domains, or subsets thereof, and thus comprise the CD19 antigen binding domains for use in the CARs described herein. In one embodiment, the other nucleotide and/or amino acid variant within the CD19 variable ScFv antigen binding domains include, for example, the CD19 variable ScFv antigen binding domains-containing variant labelled as FMC63 (SEQ ID NO: 46 and SEQ ID NO: 47 (nucleotide sequence and amino acid sequence, respectively) (cf., Example 1)

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD33. Preferably, the antigen binding domain in the CAR is anti-CD33 ScFv, wherein the nucleic acid sequence of the anti-CD33 ScFv comprises the sequence set forth in SEQ ID NO: 48. In one embodiment, the anti-CD33 ScFv comprises the nucleic acid sequence that encodes the amino acid sequence of SEQ ID NO: 49. In another embodiment, the anti-CD33 ScFv portion of the CAR comprises the amino acid sequence set forth in SEQ ID NO: 49.

In one exemplary embodiment, the antigen binding domain portion of the CAR additionally targets mesothelin. Preferably, the antigen binding domain in the CAR is anti-mesothelin ScFv, wherein the nucleic acid sequence of the anti-mesothelin ScFv comprises the nucleotide sequence set forth in SEQ ID NO: 50. In one embodiment, the anti-mesothelin ScFv comprises the nucleic acid sequence that encodes the amino acid sequence of SEQ ID NO: 51. In another embodiment, the anti-mesothelin ScFv portion of the CAR comprises the amino acid sequence set forth in SEQ ID NO: 51.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of *Staphylococci, Streptococcus, Escherichia coli, Pseudomonas,* or *Salmonella*. Particularly, there is provided a CAR capable of binding to an antigen derived from an infectious bacterium, for example, *Helicobacter pyloris, Legionella pneumophilia,* a bacterial strain of *Mycobacteria* sps. (e.g. *M. tuberculosis, M. avium, M. intracellulare, M. kansaii,* or *M. gordonea*), *Staphylococcus aureus, Neisseria gonorrhoeae, Neisseria meningitides, Listeria monocytogenes, Streptococcus pyogenes,* Group A *Streptococcus,* Group B *Streptococcus (Streptococcus agalactiae), Streptococcus pneumoniae,* or *Clostridium tetani,* or a combination thereof.

2. Transmembrane Domain

With respect to the transmembrane domain, the CAR comprises one or more transmembrane domains fused to the extracellular CD19 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 35. In one embodiment, the CD8 transmembrane domain comprises the nucleic acid sequence that encodes the amino acid sequence of SEQ ID NO: 36. In another embodiment, the CD8 transmembrane domain comprises the amino acid sequence of SEQ ID NO: 36.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 36, or a sequence with 95-99% identity to an amino acid sequence of SEQ ID NO: 36.

In some instances, the transmembrane domain of the CAR comprises the CD8.alpha.hinge domain. In one embodiment, the CD8 hinge domain comprises the nucleic acid sequence of SEQ ID NO: 37. In one embodiment, the CD8 hinge domain comprises the nucleic acid sequence that encodes the amino acid sequence of SEQ ID NO: 38. In another embodiment, the CD8 hinge domain comprises the amino acid sequence of SEQ ID NO: 38, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239, 104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 39) which is a hinge region of CD8.alpha. (NCBI RefSeq: NP.sub.—001759.3), amino acid numbers 135 to 195 of CD8.beta. (GenBank:

AAA35664.1), amino acid numbers 315 to 396 of CD4 (NCBI RefSeq: NP.sub.—000607.1), or amino acid numbers 137 to 152 of CD28 (NCBI RefSeq: NP.sub.—006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 18.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.—932170.1), amino acid numbers 45 to 86 of Fc.epsilon.RI.gamma. (NCBI RefSeq: NP.sub.—004097.1), amino acid numbers 201 to 244 of Fc.epsilon.RI.beta. (NCBI RefSeq: NP.sub.—000130.1), amino acid numbers 139 to 182 of CD3.gamma. (NCBI RefSeq: NP.sub.—000064.1), amino acid numbers 128 to 171 of CD3 .delta. (NCBI RefSeq: NP.sub.—000723.1), amino acid numbers 153 to 207 of CD3.epsilon. (NCBI RefSeq: NP.sub.—000724.1), amino acid numbers 402 to 495 of CD5 (NCBI RefSeq: NP.sub.—055022.2), amino acid numbers 707 to 847 of 0022 (NCBI RefSeq: NP.sub.—001762.2), amino acid numbers 166 to 226 of CD79a (NCBI RefSeq: NP.sub.—001774.1), amino acid numbers 182 to 229 of CD79b (NCBI RefSeq: NP.sub.—000617.1), and amino acid numbers 177 to 252 of CD66d (NCBI RefSeq: NP.sub.—001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.—001758.2), amino acid numbers 421 to 458 of CD4 (NCBI RefSeq: NP.sub.—000607.1), amino acid numbers 402 to 495 of CD5 (NCBI RefSeq: NP.sub.—055022.2), amino acid numbers 207 to 235 of CD8.alpha. (NCBI RefSeq: NP.sub.—001759.3), amino acid numbers 196 to 210 of CD83 (GenBank: AAA35664.1), amino acid numbers 181 to 220 of CD28 (NCBI RefSeq: NP.sub.—006130.1), amino acid numbers 214 to 255 of CD137 (4-1BB, NCBI RefSeq: NP.sub.—001552.2), amino acid numbers 241 to 277 of CD134 (OX40, NCBI RefSeq: NP.sub.—003318.1), and amino acid numbers 166 to 199 of ICOS (NCBI RefSeq: NP.sub.—036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 40 and the signaling domain of CD3-zeta comprises the nucleic acid sequence set forth in SEQ ID NO: 42 and in the variant nucleic acid sequence set forth in SEQ ID NO: 44. In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 40, and the signaling domain of CD3-zeta comprises the nucleic acid sequence set forth in SEQ ID NO: 42, or in another embodiment, the CD3-zeta variant nucleic acid sequence set forth in SEQ ID NO: 44.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 41 and the signaling domain of CD3-zeta comprises the nucleic acid sequence that encodes the amino acid sequence of SEQ ID NO: 43, or in another embodiment, the CD3-zeta variant nucleic acid that encodes the amino acid sequence of SEQ ID NO: 45.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 41 and the signaling domain of CD3-zeta comprises the amino acid sequence set forth in SEQ ID NO: 43 and the variant amino acid sequence set forth in SEQ ID NO: 45.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3 (10):1299-1304), or a 3'-N-amide analog (Lau et al., 1995, Bioorg-Med-Chem. 3 (10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses.

The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λÜ TIO, λÜ TI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17 (8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell on which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells, memory T cells, memory stem cells, i.e. Tscm, naive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., meduUoblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44 (2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055, 303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of CD19-Specific Antibodies from a Fully Human Phage and Yeast-Displayed ScFv Library Materials and Methods:

a) Production of Human ScFv and CD19-Specific Antibodies

A naïve human ScFv (recombinant single chain fragment variable of immunoglobulin) phage display library (approximate diversity, $10^{10}$ unique specificities), constructed from peripheral blood B cells of 50 healthy donors (Z. Y. Zhu and D. S. Dimitrov, unpublished data), were used for selection of ScFvs for recombinant human CD19 protein (Miltenyi Biotec, unpublished). Amplified libraries of $10^{12}$ phage-displayed ScFv were incubated with 5, 3, and 1, µg of coated CD19 in a 5×100-µl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 µl 2YT medium containing 100 µg/ml carbenicillin and 0.2% glucose in 96-well plates by using the automated BioRobotics BioPick colony picking system (Genomic Solutions, Ann Arbor, Mich.). After the bacterial cultures reached an optical density at 600 nm (OD600) of 0.5, helper phage M13K07 at a multiplicity of infection (MOI) of 10 and kanamycin at 50 µg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying ScFvs or VHs with high CD19 binding affinity. The supernatants were incubated for 2 h at room temperature with recombinant human CD19 coated at 50 ng per well in 96-well plates and washed five times with PBST, (after overnight incubation at 4° C. it was blocked with 3% nonfat milk in PBS and washed three times with PBS containing 0.05% Tween 20.) CD19-bound phage were detected using horseradish peroxidase-conjugated goat anti-M13 antibody. After incubation with the antibody, the non-specifically bound antibody was removed by washing wells, and the 3,3',5,5'-tetramethylbenzidine (TMB) substrate was added, and solution absorbance at 450 nm (A450) measured. Clones that bound to CD19 with A450 of >1.0 were selected for further characterization.

b) Expression and Purification of Selected Soluble ScFvs.

The VH and VL of the selected clones were DNA sequenced, and the ScFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 µg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, Mo.). After 30 min incubation with rotation at 50 rpm at room temperature, the resuspended pellet was centrifuged at 25,000×g for 25 min at 4° C., and the supernatant was used for ScFv purification using the Ni-NTA resin following vendor protocol (Qiagen).

c) ELISA binding assay 50 µl of the diluted recombinant human CD19 in PBS at 2 ug/ml was coated in a 96-well plate at 4° C. overnight. Purified ScFv with His and Flag tags were serially diluted and added into the target protein coated wells. After washing, a 1:3000 diluted HRP conjugated anti-Flag antibody was added for 1 hr at RT. After washing, 3, 3, 5, 5'-Tetramethylbenzidine (TMB) substrate was added, 1N $H_2SO_4$ was added to stop the reaction after incubation at room temperature for 10 minutes, and the O.D. was read at 450 nm to quantify the relative ability of ScFv to bind CD19.

d) Yeast Display of scFv Library.

The same ScFv starting material as for phage display was also incorporated into a yeast ScFv display system. To supplement phage-based scFv analysis, yeast libraries expressing the human scFv library were also screened. To enrich the yeast expressing scFvs that bind to both the recombinant CD19-Fc and the CD19 expressed on the cell surface of the CHOK1 cells, cell panning on CHOK1 transfected with CD19 cells was performed. For the first round of panning on the cell surface, two days prior to panning, the CHOK1-CD19 cells were seeded into 6-well plates and grown to 50% confluency in F12 K medium. $5×10^7$ yeast cells were then washed 2× with PBSA buffer and resuspended into 3 mL F12 K medium, and then gently added dropwise to the CHOK1-CD19 cells. After rocking gently on ice for 2 hours, the CHOK1-CD19 cells were then washed 3 times with ice-cold PBSA to remove the yeast cells that did not bind to the CHOK1-CD19, and 0.05% Trypsin-EDTA (Gibco) was then used to dissociate the CHOK1-CD19 cells and bound yeast cells from the plate. The cell mix containing both the yeast and CHOK1 cells were then inoculated into 10 mL SDCAA medium and amplified overnight at 30° C. and then induced in SGCAA medium at 30° C. for 16 hours. For the second round of cell panning, a similar protocol as above was performed, but more stringent wash conditions were used. This method of panning yielded the m19217 binder. Further characterization of this binder as well as others from phage display indicated that affinity maturation was required, as the biological characteristics of the CAR created from this hit were still not optimal.

To increase the affinity of m19217, a yeast-display m19217 mutant scFv library was created by using error-prone PCR to create random point mutations in scFv gene sequences. After electroporation, the resulting mutant library was then grown overnight at 30° C. for 16 hours in SDCAA medium and then switched into SGCAA medium at 30° C. for another 16 hours. The mutant library was then sorted through MACS (immunomagnetic column, Miltenyi Biotec) with CD19-Fc as the capture antigen to downsize the library and to increase the population of mutants that could bind to CD19-Fc. The strongest binders were then selected by double staining the pools with Anti-c-Myc-Alexa 488 and CD19-Fc/Anti-Hu-Fc and selecting for the binders that had the highest binding affinities as well as c-Myc expression levels. This process was then repeated two more times, until flow cytometry of yeast particles with fluorescently tagged antigen yielded average binding affinities of the mutant pools that were increased over the starting construct. Binding affinities were estimated by flow cytometry of yeast pools using decreasing amounts of labeled CD19. This process resulted in an increase of EC50 (Effective concentration for 50% binding of labeled CD19 on yeast displaying ScFv) for M19217 of 0.5 ug/ml to an affinity of <0.01 ug/ml for the affinity matured binders (M19217-1, 19217-2, M19217-7, M19217-23, M19217-29, M19217-38, M19217-40).

Results:

Due to the unique challenges of CD19 structure, phage display candidates did not yield biologically functional CAR constructs and thus ScFv identification that yielded biologically active binders were generated by yeast display. Based upon flow cytometry analysis of yeast-displayed ScFv, eight ScFv clones specific for recombinant human CD19 were identified and labeled as human anti-CD19 ScFv binders M19217 (LTG2050, founder clone, EC50 of 0.5 ug/ml), and the following affinity matured binders (EC50<0.01 ug/ml): M19217-1 (LTG2065), M19217-2 (LTG2066), M19217-7 (LTG2067), M19217-23 (LTG2068), M19217-29 (LTG2069), M19217-38 (LTG2070), and M19217-40 (LTG2071) respectively. The generation of chimeric antigen receptors expressing the LTG2050, LTG2065, LTG2066, LTG2067, LTG2068, LTG2069, LTG2070, and LTG2071 human anti-CD19 binders is outlined in Example 2, infra.

Example 2

CARs Expressing Anti-CD19 Fully Human Binding Sequences

Homo sapiens CD19 (B4, CVID3, Leu-12) is a well-investigated cell surface glycoprotein expressed on B cell leukemias and lymphomas. At least two antibody drug conjugates, (SGN-CD19A Denintuzumab Mafodotin (Seattle Genetics) and SAR3419 Coltuximab Ravtansine are being evaluated in phase II clinical trials. A phase one study of SGN-19A showed a 35% CRc in the optimal treatment group (Fathi A T, Borate U, DeAngelo D J, O'Brien M M, Trippett T, Shah B D, Hale G A, Foran J M, Silverman L B, Tibes R, Cramer S, Pauly M, Kim S, Kostic A, Huang X, Pan Y, Chen R, 2015, Blood 126:1328). However, due to disappointing phase II results for SAR3419, development is on hold (Coiffer B, Thieblemont C, de Guibert S, Dupuis J, Ribrag V, Bouabdallah R, Morschhauser F, Navarro R, Le Gouill S, Haioun C, Houot R, Cassasnovas O, Holte H, Lamy T, Broussais F, Payrard S, Hatteville L, Tilly H, 2016, Bt J Haematolo 173:722-30). The use of a bi-specific anti-$CD^3$/anti-CD19 antibody (Blinotumomab) was discussed above. Given the current advances with T-cell based therapy with CD19 CARs, the best approach is certainly cell-based immunotherapy and the CAR constructs presented here are an innovative new approach to creating and implementing new CD19 binding moieties derived from human sequences.

The novel anti-CD19 CAR-T constructs described here have high levels of cell surface expression in primary human T cells and specific and potent cytotoxic and cytokine functions against CD19-positive tumor cells. CD19 CARs were designed using CD19 binding sequences derived from ScFv candidates identified by phage display, as in Example 1, and for characterization were cloned into lentiviral expression vectors that contained selected structural and signaling domains under the control of the EF1a promoter and tested in vitro for transduction efficiency, killing function and cytokine production in both model cell lines and primary human T cells. Table 1 summarizes the nomenclature used. CAR Construct LTG#1538 is the relevant comparator, as this mouse-derived sequence is the current binder employed in commercial development (See KTE-C19, Kite Pharma, and CTL019, Novartis).

TABLE 1

Construct LTG numbers and corresponding ScFv binder designations used in the design of fully human CD19 CARs

| CAR Construct LTG# | huCAR19 ScFv binder |
|---|---|
| UTD | Untransduced T cell control |
| 1538 | FMC63 murine CAR19 control |
| 2050 | M19217 |
| 2065 | M19217-1 |
| 2066 | M19217-2 |
| 2067 | M19217-7 |
| 2068 | M19217-23 |
| 2069 | M19217-29 |
| 2070 | M19217-38 |
| 2071 | M19217-40 |

Materials and Methods:

(a) Cell Lines

The Burkitt lymphoma cell line Raji and the chronic myelogenous leukemia line K562 were purchased from American Tissue Culture Collection (ATCC, Manassass, Va.). Cells were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). Human Embryonic kidney line 293T was purchased from ATCC and propagated in CD FortiCho medium (Gibco/Thermo Fisher Scientific, Grand Island, N.Y.). Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones.

(b) Creation of Chimeric Antigen Receptor (CAR)—Expression Vectors

CAR antigen-binding domains, ScFv, sequences were derived from human anti-CD19 ScFv fragments. CAR T constructs were generated by linking the binder sequence in frame to CD8a linking and transmembrane domains (UniProt sequence ID P01732, aa 138-206), and then to 4-1BB (CD137, aa 214-255, UniProt sequence ID Q07011) signaling domain and CD3 zeta signaling domain (CD247, aa 52-163, Ref sequence ID: NP_000725.1). CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T cell Purification and Transduction

Human primary T cells from healthy volunteers were purified from whole blood or buffy coats (purchased from commercial provider with donor's written consent) using immunomagnetic bead selection of CD4+ and CD8+ cells according to manufacturer's protocol (Miltenyi Biotec, Bergisch Gladbach, Germany). T cells were cultivated in TexMACS medium supplemented with 200 IU/ml IL-2 at a density of 0.3 to 2×10$^6$ cells/ml, activated with CD3/CD28 MACS® GMP T Cell TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 3. Cultures were propagated in TexMACS medium supplemented with 200 IU/ml IL-2 until harvest on day 8-12.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1−(sample CPS−min CPS)/(max CPS−min CPS)). Supernatants from co-cultures at E:T ratio of 10:1 were removed and analyzed by ELISA (eBioscience, San Diego, Calif.) for IFNγ, TNFα and IL-2 concentration.

(e) Flow Cytometric Analysis

For cell staining, half a million CAR T transduced cells were harvested from culture, washed two times in cold AutoMACS buffer supplemented with 0.5% bovine serum albumin (Miltenyi Biotec), and CAR surface expression detected by staining with CD19-Fc peptide (R&D, Minneapolis, Minn.) followed by anti Fc-AF647 conjugate (Jackson ImmunoResearch, West Grove, Pa.). Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

Results:

In order to evaluate the novel anti-CD19 fully human ScFv binding sequences, CAR constructs were designed incorporating each one of the ScFv sequences, Table 1, ScFv1 (M19217), ScFv2 (M19217-1), ScFv3 (M19217-2), ScFv4 (M19217-7), ScFv5 (M19217-23), ScFv6 (M19217-29), ScFv7 (M19217-38), ScFv8 (M19217-40), as a tumor antigen binding domain. In each CAR design, the tumor targeting domain was followed by a linker and transmembrane domains derived from the human CD8 protein, a 4-1BB costimulatory domain and a CD3 zeta signaling domain (Table 2 infra). CAR construct encoding murine immunoglobulin-derived FMC63 binder sequence was used as a positive control.

TABLE 2

List of CD19 - Targeting CAR Constructs

LTG1538: FMC63-CD8 TM-41BB-CD3 zeta, control
LTG2050: ScFv1-CD8 TM-41BB-CD3 zeta
LTG2065: ScFv2-CD8TM-4-1BB-CD3 zeta
LTG2066: ScFv3-CD8TM-4-1BB-CD3 zeta
LTG2067: ScFv4-CD8TM-4-1BB-CD3 zeta
LTG2068: ScFv5-CD8TM-4-1BB-CD3 zeta
LTG2069: ScFv6-CD8TM-4-1BB-CD3 zeta
LTG2070: ScFv7-CD8TM-4-1BB-CD3 zeta
LTG2071: ScFv8-CD8TM-4-1BB-CD3 zeta T cells Transduced with Anti-CD19 Chimeric Antigen Receptors Demonstrate Surface Expression and Cytolytic Activity.

a) Surface Expression of Anti-CD19 CARs

To evaluate the novel anti-CD19 CARs, lentiviral vectors (LV) encoding CAR constructs under the control of human EF1a promoter were generated as described in Materials and Methods. Then, human primary T cells derived from healthy donors were transduced lentiviral vectors encoding CARs. Non-transduced cells from same donor (NT) or GFP-transduced cells from same donor served as negative controls. Data is representative of results from at least 3 assays from different donors.

T cells were activated on culture Day 0 with TransAct T cell reagent (active engagement of CD3 and CD28 antigens, Miltenyi Biotec, Inc.) in the presence of IL-2 as described in Materials and Methods. On culture Day 8-10, expression of anti-CD19 CARs on T cell surface was detected by CD19-Fc peptide followed by anti Fc-AF647 and analyzed by flow cytometry. Anti-CD19 CAR constructs selected each demonstrated surface CAR expression. Using untransduced T cells as a negative control (0%) the following CAR expression levels were seen: LTG1538, 60%; LTG2050, 46%; LTG2065, 64%; LTG2066, 21%; LTG2067, 81%; LTG2068, 54%; LTG2069, 68%; LTG2070, 47%; LTG2071, 21%.

b) Cytolytic Assay and Cytokine Assay of Anti-CD19 CARs

Figure 5:
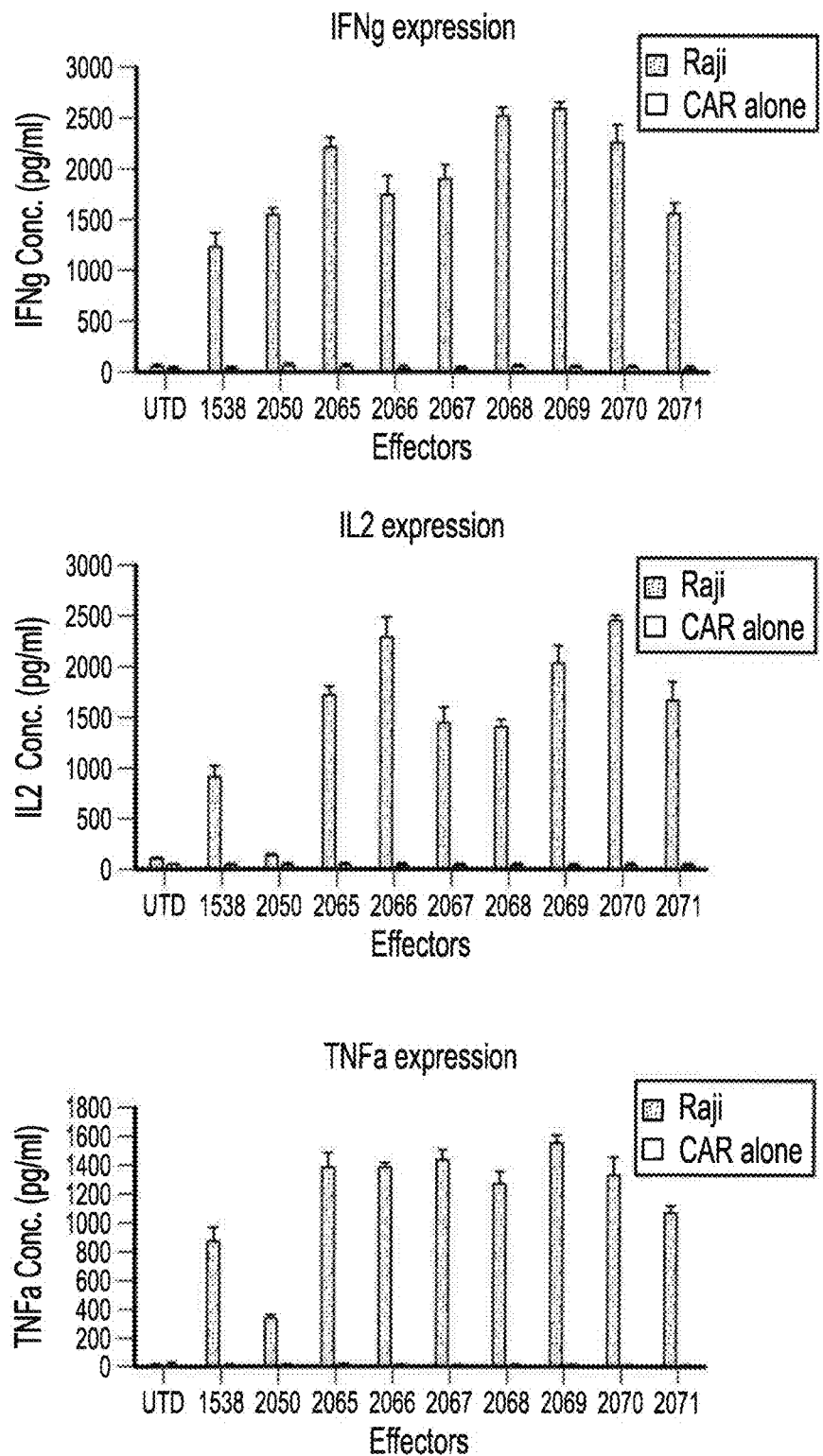
FIG. 5 depicts CD19-specific CART cell production of high levels of cytokines when co-cultured with the CD19-positive leukemia line (dark gray), or T cells were incubated alone (gray). The assay was carried out overnight at E:T ratio of 10:1, then supernatants were analyzed for cytokine concentrations by ELISA. N=2 technical replicates +/−SD. Negative controls: UT—un-transduced T cells, 1538-FMC63 murine CD19 positive control-transduced T cells. LTG numbers of each LV used to transduce human T cells are listed on the x-axis.

To demonstrate the cytolytic function of the generated CART cells, a luciferase-based killing assay was performed by combining CAR-T with CD19-positive Raji-luc cells, CD19-positive Reh-luc cells, CD19-negative K562-luc, or CD19-negative 293T-luc cells at E:T ratios of 40:1, 20:1, or 10:1 in overnight cell killing assays as described in Materials and Methods (FIG. 4). Selected constructs (LTG2050, LTG2065-2071) showed dose-dependent, CD19-specific tumor killing. Then, we measured the concentration of inflammatory cytokines IFN-gamma, TNF-alpha and IL-2 secreted by CAR T cells transduced with CAR19 constructs, when challenged by CD19-positive cell tumor cells (FIG. 5). CAR T cells alone controls were included for each construct, in order to test for basal levels of cytokine production. Levels of TNF-alpha, IFN-gamma and IL-2 were strongly induced by T cells exposed to CD19$^+$ Raji cells. Furthermore, none of the constructs demonstrated cytokine production above baseline in the absence of tumor cell targets. Therefore, CAR T constructs LTG2050, LTG2065-2071 are specific for CD19$^+$ tumor lines. Interestingly, construct LTG2050, despite efficient in vitro killing of CD19-positive cell lines, elaborated low levels of IL-2 as detected by ELISA. Therefore, CAR design and binder choice are not trivial, as some binders active in a soluble IgG or ScFv format and amenable to expression on T cell surface in a CAR T format, are nevertheless inefficient in killing or producing cytokines when co-incubated with CD19-positive tumors. Binders that were not expressed on the surface of T cells in our CAR expression vectors, or which did not evidence strong lytic activity against CD19-positive cell lines are not included herein, though many were found during screening.

In summary, high functionality of novel fully human anti-CD19 CAR constructs LTG2050, LTG2065, LTG2066, LTG2067, LTG2068, LTG2069, LTG2070, and LTG2071 (Table 1 infra) was demonstrated. All CAR constructs, except LTG2050, were superior to the positive control, murine FMC63 (LTG1538), and thus are expected to have more potent therapeutic activity.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
nucleotide sequence of CD19-reactive ScFv1 binding domain (LTG2050)
                                                                SEQ ID NO: 1
GAGGTCCAGCTGGTACAGTCTGGAGCTGAGGTGAAGAAGCCTGGGGCCTCAGTGAAGGTCTCCTGCAAGGCTTCTGGATACAC CTTCACCAGCTACTATATGCACTGGGTGCGACAGGCCCCTGGACAAGGGCTTGAGTGGATGGGAATAATCAACCCTAGTGGTG GTAGCACAAGCTACGCACAGAAGTTCCAGGGCAGAGTCACCATGACCAGGGACACGTCCACGAGCACAGTCTACATGGAGCTG AGCAGCCTGAGATCTGAGGACACGGCCGTGTATTACTGTGCGAGATCGGATCGGGGAATTACCGCCACGGACGCTTTTGATAT CTGGGGCCAAGGGACAATGGTCACCGTCTCTTCAGGAGGTGGCGGGTCTGGTGGAGGCGGTAGCGGTGGTGGCGGATCCCAGT CTGTGCTGACTCAGCCACCCTCGGTGTCAGTGGCCCCAGGGCAGACGGCCAAGATTACCTGTGGGGGAAGTGACATTGGAAAT
```

```
AAAAATGTCCACTGGTACCAGCAGAAGCCAGGCCAGGCCCCTGTCCTGGTCGTCTATGATGATTACGACCGGCCCTCAGGGAT

CCCTGAGCGATTCTCTGGCTCCAACTCTGGGGACGCGGCCACCCTGACGATCAGCACGGTCGAAGTCGGGGATGAGGCCGACT

ATTTCTGTCAGGTGTGGGACAGTAGTGGTGATCCTTATTGGGTGTTCGGCGGAGGGACCCAGCTCACCGTTTTAGGT
``` amino acid sequence of CD19-reactive ScFv1 binding domain (LTG2050)
SEQ ID NO: 2

```
EVQLVQSGAEVKKPGASVKVSCKASGYTFTSYYMHWVRQAPGQGLEWMGIINPSGGSTSYAQKFQGRVTMTRDTSTSTVYMEL

SSLRSEDTAVYYCARSDRGITATDAFDIWGQGTMVTVSSGGGGSGGGGSGGGGSQSVLTQPPSVSVAPGQTAKITCGGSDIGN

KNVHWYQQKPGQAPVLVVYDDYDRPSGIPERFSGSNSGDAATLTISTVEVGDEADYFCQVWDSSGDPYWVFGGGTQLTVLG
``` nucleotide sequence of CD19-reactive ScFv2 binding domain (LTG2065)
SEQ ID NO: 3

```
GAGGTCCAGCTGGTACAGTCTGGAGCTGAGGTGAAGAAGCCTGGGGCCTCAGTGAAGGTCTCCTGCAAGGCTTCTGGATACAC

CTTCACCAGCTACTATATGCACTGGGTGCGACAGGCCCCTGGACAAGGGCTTGAGTGGATGGGATTAATCAACCCTAGTGGTG

GTAGCACAAGCTACGCACAGAAGTTCCAGGGCAGAGTCACCATGACCAGGGACACGTCCACGAGCACAGTCTACATGGAGCTG

AGCAGCCTGAGATCTGAGGACACGGCCGTGTATTACTGTGCAGATCGGATCGGGGAATTACCGCCACGGACGCTTTTGATAT

CTGGGGCCAAGGGACAATGGTCACCGTCTCTTCAGGCGGAGGAGGCTCCGGGGGAGGAGGTTCCGGGGGCGGGGGTTCCCAGT

CTGTGCTGACTCAGCCACCCTCGGTGTCAGTGGCCCCAGGGCGGATGGCCAAGATTACCTGTGGGGGAAGTGACATTGGAAAT

AAAAATGTCCACTGGTATCAGCAGAAGCCAGGCCAGGCCCCTGTCCTGGTTGTCTATGATGATTACGACCGGCCCTCAGGGAT

CCCTGAGCGATTCTCTGGCTCCAACTCTGGGGACGCGGCCACCCTGACGATCAGCACGGTCGAAGTCGGGGATGAGGCCGACT

ATTTCTGTCAGGTGTGGGACGGTAGTGGTGATCCTTATTGGATGTTCGGCGGAGGGACCCAGCTCACCGTTTTAGGT
``` amino acid sequence of CD19-reactive ScFv2 binding domain (LTG2065)
SEQ ID NO: 4

```
EVQLVQSGAEVKKPGASVKVSCKASGYTFTSYYMHWVRQAPGQGLEWMGLINPSGGSTSYAQKFQGRVTMTRDTSTSTVYMEL

SSLRSEDTAVYYCARSDRGITATDAFDIWGQGTMVTVSSGGGGSGGGGSGGGGSQSVLTQPPSVSVAPGRMAKITCGGSDIGN

KNVHWYQQKPGQAPVLVVYDDYDRPSGIPERFSGSNSGDAATLTISTVEVGDEADYFCQVWDGSGDPYWMFGGGTQLTVLG
``` nucleotide sequence of CD19-reactive ScFv3 binding domain (LTG2066)
SEQ ID NO: 5

```
GAGGTCCAGCTGGTACAGTCTGGAGCTGAGGTGAAGAAGCCTGGGGCCTCAGTGAAGGTCTCCTGCAAGGCTTCCGGATACAC

CTTCACCAGCTACTACATGCACTGGGTGCGACAGGCCCCTGGACAAGGGTTTGAGTGGATGGGATTAATCAACCCTAGTGGTA

GTAGCACAAGCTACGCACAGAAGTTCCAGGGCAGAGTCACCATGACCAGGGACACGTCCACGAGCACAGTCTACATGGAGCTG

AGCAACCTGAGATCTGAGGACACGGCCGTGTATTACTGTGCAGATCGGATCGGGGAATTACCGCCACGGACGCTTTTGATAT

CTGGGGCCAAGGGACAATGGTCACCGTCTCTTCAGGCGGAGGAGGCTCCGGGGGAGGAGGTTCCGGGGGCGGGGGTTCCCAGT

CTGTGCTGACTCAGCCACCCTCGGTGCCAGTGGCCCCAGGGCAGACGGCCAAGATTATCTGTGGGGGAAGTGACATTGGAAAT

AAAAATGTCCACTGGTACCAGCAGAAGCCAGGCCAGGCCCCTGTCCTGGTCGTCTATGATGACTACGACCGGCCCTCAGGGAT

CCCTGAGCGATTCTCTGGCTCCAACTCTGGGGACGCGGCCACCCTGACGATCAGCACGGTTGAAGTCGGGGATGAGGCCGACT

ATTTCTGTCAGGTGTGGGACGGTAGTGGTGATCCTTATTGGGTGTTCGGCGGAGGGACCCAGCTCACCGTCTTAGGT
``` amino acid sequence of CD19-reactive ScFv3 binding domain (LTG2066)
SEQ ID NO: 6

```
EVQLVQSGAEVKKPGASVKVSCKASGYTFTSYYMHWVRQAPGQGFEWMGLINPSGSSTSYAQKFQGRVTMTRDTSTSTVYMEL

SNLRSEDTAVYYCARSDRGITATDAFDIWGQGTMVTVSSGGGGSGGGGSGGGGSQSVLTQPPSVPVAPGQTAKIICGGSDIGN

KNVHWYQQKPGQAPVLVVYDDYDRPSGIPERFSGSNSGDAATLTISTVEVGDEADYFCQVWDGSGDPYWVFGGGTQLTVLG
``` nucleotide sequence of CD19-reactive ScFv4 binding domain (LTG2067)
SEQ ID NO: 7

```
GAGGTCCAGCTGGTACAGTCTGGAGCTGAGGTGAACAAGCCTGGTGCCTCAGTGAAGGTCTCCTGCAAGGCTTCTGGATACAC

CTTCACCAGCTACTATATGCACTGGGTGCGACAGGCCCCTGGACAAGGGCTTGAGTGGATGGGAATGATCAACCCTAGTGGTG

GTAGCACAAGCTACGCACAGAAGTTCCAGGGCAGAGTCACCATGACCAGGGACACGTCCACGAGCACAGTCTACATGGAGCTG

AGCAGCCTGAGATCTGAGGACACGGCCGTGTATTACTGTGCAGATCGGATCGGGGAATTACCTCCACGGACGCTTTTGATAT
```

CTGGGGCCAAGGGACAATGGTCACCGTCTCTTCAGGCGGAGGAGGCTCCGGGGGAGGAGGTTCCGGGGGCGGGGGTTCCCAGT

CTGTGCTGACTCAGCCACCCTCGGTGTCATTGGCCCCAGGGCAGACGGCCAAGATTACCTGTGGGGGAAGTGACATTGGAAAT

AAAAATGTCCACTGGTACCAGCAGAAGCCAGGCCAGGCCCCTGTCCTAGTCGTCTATGATGATTACAACCGGCCCTCAGGGAT

CCCTGAGCGATTCTCTGGCTCCAACTCTGGGGACTCAGCCACCCTGACGATCAGCACGGTCGAAGTCGGGGATGAGGCCGACT

ATTTCTGTCAGGTGTGGGACGGTAGTGGTGATCCTTATTGGGTGTTCGGCGGAGGGACCCAGCTCACCGTTTTAGGT amino acid sequence of CD19-reactive ScFv4 binding domain (LTG2067)
SEQ ID NO: 8
EVQLVQSGAEVNKPGASVKVSCKASGYTFTSYYMHWVRQAPGQGLEWMGMINPSGGSTSYAQKFQGRVTMTRDTSTSTVYMEL SSLRSEDTAVYYCARSDRGITSTDAFDIWGQGTMVTVSSGGGGSGGGGSGGGGSQSVLTQPPSVSLAPGQTAKITCGGSDIGN KNVHWYQQKPGQAPVLVVYDDYNRPSGIPERFSGSNSGDSATLTISTVEVGDEADYFCQVWDGSGDPYWVFGGGTQLTVLG nucleotide sequence of CD19-reactive ScFv5 binding domain (LTG2068)
SEQ ID NO: 9
GAGGTCCAGCTGGTACAGTCTGGAGCTGAGGTGAAGAAGCCTGGGGCCTCAGTGAAGGTCTCCTGCAAGGCATCTGGATACAC CTTCACCGGCTACTATATGCACTGGGTGCGGCAGGCCCCTGGACAAGGGCTTGAGTGGATAGGATTAATCAACCCTAGTGGTG GTAGCACAAGCTACGAACAGAAGTTCCAGGGCAGAGTCGCCATGACCAGGGACACGTCAACGAGCACAGTCTACATGGAGCTG AGCAGCCTGAGATCTGAGGACACGGCCGTGTATTACTGTGCGAGATCGGATCGGGGAATTACCGCCACGGACGCTTTTGATAT CTGGGGCCAAGGGACAATGGTCACCGTCTCTTCAGGCGGAGGAGGCTCCGGGGGAGGAGGTTCCGGGGGCGGGGGTTCCCAGT CTGTGCTGACTCAGCCACCCTCGGTGTCAGTGGCCCCAGGGCAGACGGCCAAGATTACCTGTGGGGGAAGTGACATTGGAGAT AAAAATGTCCACTGGTACCAGCAGAAGCCAGGCCAGGCCCCTGTCCTGGTCGTCTATGATGATTACGACCGGCCCTCAGGGAT CCCTGAGCGATTCTCTGGCTCCAACTCTGGGGACGCGGCCACCCTGACGATCAGCACGGTCGAAGTCGGGGATGAGGCCGACT

ATTTCTGTCAGGTGTGGGACGGTATTGGTGATCCCTATTGGGTGTTCGGCGGAGGGACCCAGCTCACCGTTTTAGGT amino acid sequence of CD19-reactive ScFv5 binding domain (LTG2068)
SEQ ID NO: 10
EVQLVQSGAEVKKPGASVKVSCKASGYTFTGYYMHWVRQAPGQGLEWIGLINPSGGSTSYEQKFQGRVAMTRDTSTSTVYMEL SSLRSEDTAVYYCARSDRGITATDAFDIWGQGTMVTVSSGGGGSGGGGSGGGGSQSVLTQPPSVSVAPGQTAKITCGGSDIGD KNVHWYQQKPGQAPVLVVYDDYDRPSGIPERFSGSNSGDAATLTISTVEVGDEADYFCQVWDGIGDPYWVFGGGTQLTVLG nucleotide sequence of CD19-reactive ScFv6 binding domain (LTG2069)
SEQ ID NO: 11
GAGGTCCAGCTAGTACAGTCTGGAGCTGAGGTGAAGAAGCCTGGGGCCTCAGTGAAGGTCTCCTGCAAGGCTTCTGGATACAC CTTCACCAGCTACTATATGCACTGGGTGCGACAGGCCCCTGGACAAGGGCTTGAGTGGATGGGAATGATCAACCCTAGTGGTG GTAGCACAAGCTACGCACAGAAGTTCCAGGGCAGAGTCACCATGACCAGGGACACGTCCACGAGCACAGTCTACATGGAGCTG AGCAGCCTGAGATCTGAGGACACGGCCGTGTATTACTGTGCGAGATCGGATCGGGGAATTACCGCCACGGACGCTTTTGATAT CTGGGGCCAAGGGACAATGGTCACCGTCTCTTCAGGCGGAGGAGGCTCCGGGGGAGGAGGTTCCGGGGGCGGGGGTTCCCAGT CTGTGCTGACTCAGCCACCCTCGGTGTCAGTGGCCCCAGGGCAGACGGCCAAGATTACCTGTGGGGGAAGTGACATTGGAAAT AAAAATGCCCACTGGTACCAGCAGAAGCCAGGCCAGGCCCCTGTCCTGGTCGTCTATGATGATTACGACCGGCCCTCAGGGAT CTCTGAGCGATTCTCTGGCTCCAACTCTGGGGACGCGGCCACCCTGACGATCAGCACGGTCGAAGTCGGGGATGAGGCCGACT

ATTTCTGTCAGGTGTGGGACGGTAGTGGTGATCCTTTTTGGGTGTTCGGCGGAGGGACCCAGCTCACCGTTTTAGGT amino acid sequence of CD19-reactive ScFv6 binding domain (LTG2069)
SEQ ID NO: 12
EVQLVQSGAEVKKPGASVKVSCKASGYTFTSYYMHWVRQAPGQGLEWMGMINPSGGSTSYAQKFQGRVTMTRDTSTSTVYMEL SSLRSEDTAVYYCARSDRGITATDAFDIWGQGTMVTVSSGGGGSGGGGSGGGGSQSVLTQPPSVSVAPGQTAKITCGGSDIGN KNAHWYQQKPGQAPVLVVYDDYDRPSGISERFSGSNSGDAATLTISTVEVGDEADYFCQVWDGSGDPFWVFGGGTQLTVLG nucleotide sequence of CD19-reactive ScFv7 binding domain (LTG2070)
SEQ ID NO: 13
GAGGTCCAGCTGGTACAGTCTGGAGCTGAGGTGAAGAGGCCTGGGGCCTCAGTGAAGGTCTCCTGCAAGGCTTCTGGATACAC CTTCACCAGCTACTATATGCACTGGGTGCGACAGGCCCCTGGACGAGGGCTTGAGTGGATGGGATTAATCAACCCTAGTGGTG GTAGCACAAGCTACGCACAGGAGTTCCAGGGCAGAGTCACCATGACCAGGGACATGTCCACGAGCACAGTCTACATGGAGCTG AGCAGCCTGAGATCTGAGGACACGGCCGTGTATTACTGTGCGAGATCGGATCGGGGAATTAGCGCCACGGACGCTTTTGATAT
CTGGGGCCAAGGGACAATGGTCACCGTCTCTTCAGGCGGAGGAGGCTCCGGGGGAGGAGGTTCCGGGGGCGGGGGTTCCCAGT
CTGTGCTGACTCAGCCACCCTCGGTGTCAGTGGCCCCAGGGCAGATGGCCAAGATTACCTGTGGGGGAAGTGACATTGGAAAT
AAAAATGTCCACTGGTACCAGCAGAAGCCAGGCCAGGCCCCTGTCCTGGTCGTCTATGATGATTACAACCGGCCCTCAGGGAT
CCCTGAGCGATTCTCTGGCTCCAACTCTGGGGACGCGGCCACCCTGACGATCAGCACGGTCGAAGTCGGGGATGAGGCCGACT
ATTTCTGTCAGGTATGGGACGGTAGTGGTGATCCTTATTGGGTGTTCGGCGGAGGGACCCAGCTCACCGATTTAGGT amino acid sequence of CD19-reactive ScFv7 binding domain (LTG2070)
SEQ ID NO: 14
EVQLVQSGAEVKRPGASVKVSCKASGYTFTSYYMHWVRQAPGRGLEWMGLINPSGGSTSYAQEFQGRVTMTRDMSTSTVYMEL
SSLRSEDTAVYYCARSDRGISATDAFDIWGQGTMVTVSSGGGGSGGGGSGGGGSQSVLTQPPSVSVAPGQMAKITCGGSDIGN
KNVHWYQQKPGQAPVLVVYDDYNRPSGIPERFSGSNSGDAATLTISTVEVGDEADYFCQVWDGSGDPYWVFGGGTQLTDLG nucleotide sequence of CD19-reactive ScFv8 binding domain (LTG2071)
SEQ ID NO: 15
GAGGTCCAGCTGGTACAGTCTGGAGCTGAGGTGAAGAGGCCTGGGGCCTCAGTGAAGGTCTCCTGCAAGGCTTCTGGATACAC
CTTCACCAGCTACTATATGCACTGGGTGCGACAGGCCCCTGGACAAGGGCTTGTGTGGATGGGATTAATCAACCCTAGTGGTG
GCAGCACAAGCTACGCACAGAAGTTCCAGGGCAGAGTCACCATGACCAGGGACACGTCCACGAGCACAGTCTACATGGAGCTG
AGCAGCCTGAGATCTGAGGACACGGCCGTGTATTACTGTGCGAGATCGGATCGGGGAATTACCGCCACGGACGCTTTTGATAT
CTGGGGCCAAGGGACAATGGTCACCGTCTCTTCAGGCGGAGGAGGCTCCGGGGGAGGAGGTTCCGGGGGCGGGGGTTCCCAGT
CTGTGCTGACTCAGCCACCCTCGGTCTCAGTGGCCCCAGGGCAGACGGCCAAGACTACCTGTGGGGGAAGTGACATTGGAAAT
AAAAATGTCCACTGGTACCAGCAGAAGCCAGGCCAGGCCCCTGTCCTGGTCGTCTATGATGATTACGACCGGCCCTCAGGGAT
CCCTGAGCGATTCTCTGGCTCCAACTCTGGGGACGCGGCCACCCTGACGATCAGCACGGTCGAAGTCGGGGATGAGGCCGACT
ATGTCTGTCAGGTGTGGGACGGTAGTGGTGATCCTTATTGGGTGTTCGGCGGAGGGACCCAGCTCACCGTTTTAGGT amino acid sequence of CD19-reactive ScFv8 binding domain (LTG2071)
SEQ ID NO: 16
EVQLVQSGAEVKRPGASVKVSCKASGYTFTSYYMHWVRQAPGQGLVWMGLINPSGGSTSYAQKFQGRVTMTRDTSTSTVYMEL
SSLRSEDTAVYYCARSDRGITATDAFDIWGQGTMVTVSSGGGGSGGGGSGGGGSQSVLTQPPSVSVAPGQTAKTTCGGSDIGN
KNVHWYQQKPGQAPVLVVYDDYDRPSGIPERFSGSNSGDAATLTISTVEVGDEADYVCQVWDGSGDPYWVFGGGTQLTVLG nucleotide sequence of leader/signal peptide sequence (LP)
SEQ ID NO: 17
atgctgctgctggtgaccagcctgctgctgtgcgaactgccgcatccggcgtttctgctgattccg amino acid sequence of leader/signal peptide sequence (LP)
SEQ ID NO: 18
MLLLVTSLLLCELPHPAFLLIP nucleotide sequence of LTG2050 (LP-M19217-CD8 TM-41BB-CD3 zeta)
SEQ ID NO: 19
ATGCTTCTCCTGGTCACCTCCCTGCTCCTCTGCGAACTGCCTCACCCTGCCTTCCTTCTGATTCCTGAGGTCCAGCTGGTACA
GTCTGGAGCTGAGGTGAAGAAGCCTGGGGCCTCAGTGAAGGTCTCCTGCAAGGCTTCTGGATACACCTTCACCAGCTACTATA
TGCACTGGGTGCGACAGGCCCCTGGACAAGGGCTTGAGTGGATGGGAATAATCAACCCTAGTGGTGGTAGCACAAGCTACGCA
CAGAAGTTCCAGGGCAGAGTCACCATGACCAGGGACACGTCCACGAGCACAGTCTACATGGAGCTGAGCAGCCTGAGATCTGA
GGACACGGCCGTGTATTACTGTGCGAGATCGGATCGGGGAATTACCGCCACGGACGCTTTTGATATCTGGGGCCAAGGGACAA
TGGTCACCGTCTCTTCAGGAGGTGGCGGGTCTGGTGGAGGCGGTAGCGGTGGTGGCGGATCCCAGTCTGTGCTGACTCAGCCA
CCCTCGGTGTCAGTGGCCCCAGGGCAGACGGCCAAGATTACCTGTGGGGAAGTGACATTGGAAATAAAAATGTCCACTGGTA
CCAGCAGAAGCCAGGCCAGGCCCCTGTCCTGGTCGTCTATGATGATTACGACCGGCCCTCAGGGATCCCTGAGCGATTCTCTG
GCTCCAACTCTGGGGACGCGGCCACCCTGACGATCAGCACGGTCGAAGTCGGGGATGAGGCCGACTATTTCTGTCAGGTGTGG
GACAGTAGTGGTGATCCTTATTGGGTGTTCGGCGGAGGGACCCAGCTCACCGTTTTAGGTGCGGCCGCAACTACCACCCCTGC
CCCTCGGCCGCCGACTCCGGCCCCAACCATCGCAAGCCAACCCCTCTCCTTGCGCCCCGAAGCTTGCCGCCCCGGCCGCGGGTG

```
GAGCCGTGCATACCCGGGGGCTGGACTTTGCCTGCGATATCTACATTTGGGCCCCGCTGGCCGGCACTTGCGGCGTGCTCCTG

CTGTCGCTGGTCATCACCCTTTACTGCAAGAGGGGCCGGAAGAAGCTGCTTTACATCTTCAAGCAGCCGTTCATGCGGCCCGT

GCAGACGACTCAGGAAGAGGACGGATGCTCGTGCAGATTCCCTGAGGAGGAAGAGGGGGATGCGAACTGCGCGTCAAGTTCT

CACGGTCCGCCGACGCCCCCGCATATCAACAGGGCCAGAATCAGCTCTACAACGAGCTGAACCTGGGAAGGAGAGAGGAGTAC

GACGTGCTGGACAAGCGACGCGGACGCGACCCGGAGATGGGGGGGAAACCACGGCGGAAAAACCCTCAGGAAGGACTGTACAA

CGAACTCCAGAAAGACAAGATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACTCCCACCCCGG
``` amino acid sequence of LTG2050 (LP-M19217-CD8 TM-41BB-CD3 zeta)
SEQ ID NO: 20

```
MLLLVTSLLLCELPHPAFLLIPEVQLVQSGAEVKKPGASVKVSCKASGYTFTSYYMHWVRQAPGQGLEWMGIINPSGGSTSYA

QKFQGRVTMTRDTSTSTVYMELSSLRSEDTAVYYCARSDRGITATDAFDIWGQGTMVTVSSGGGGSGGGGSGGGGSQSVLTQP

PSVSVAPGQTAKITCGGSDIGNKNVHWYQQKPGQAPVLVVYDDYDRPSGIPERFSGSNSGDAATLTISTVEVGDEADYFCQVW

DSSGDPYWVFGGGTQLTVLGAAATTTPAPRPPTPAPTIASQPLSLRPEACRFAAGGAVHTRGLDFACDIYIWAPLAGTCGVLL

LSLVITLYCKRGRKKLLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2065 (LP-M19217-1-CD8 TM-41BB-CD3 zeta)
SEQ ID NO: 21

```
ATGCTGCTGCTGGTGACCAGCCTGCTGCTGTGCGAACTGCCGCATCCGGCGTTTCTGCTGATTCCGGAGGTCCAGCTGGTACA

GTCTGGAGCTGAGGTGAAGAAGCCTGGGGCCTCAGTGAAGGTCTCCTGCAAGGCTTCTGGATACACCTTCACCAGCTACTATA

TGCACTGGGTGCGACAGGCCCCTGGACAAGGGCTTGAGTGGATGGGATTAATCAACCCTAGTGGTGGTAGCACAAGCTACGCA

CAGAAGTTCCAGGGCAGAGTCACCATGACCAGGGACACGTCCACGAGCACAGTCTACATGGAGCTGAGCAGCCTGAGATCTGA

GGACACGGCCGTGTATTACTGTGCGAGATCGGATCGGGGAATTACCGCCACGGACGCTTTTGATATCTGGGGCCAAGGGACAA

TGGTCACCGTCTCTTCAGGCGGAGGAGGCTCCGGGGGAGGAGGTTCCGGGGGCGGGGGTTCCCAGTCTGTGCTGACTCAGCCA

CCCTCGGTGTCAGTGGCCCCAGGGCGGATGGCCAAGATTACCTGTGGGGGAAGTGACATTGGAAATAAAAATGTCCACTGGTA

TCAGCAGAAGCCAGGCCAGGCCCCTGTCCTGGTTGTCTATGATGATTACGACCGGCCCTCAGGGATCCCTGAGCGATTCTCTG

GCTCCAACTCTGGGGACGCGGCCACCCTGACGATCAGCACGGTCGAAGTCGGGGATGAGGCCGACTATTTCTGTCAGGTGTGG

GACGGTAGTGGTGATCCTTATTGGATGTTCGGCGGAGGGACCCAGCTCACCGTTTTAGGTGCGGCCGCAACTACCACCCCTGC

CCCTCGGCCGCCGACTCCGGCCCCAACCATCGCAAGCCAACCCCTCTCCTTGCGCCCCGAAGCTTGCCGCCCGGCCGCGGGTG

GAGCCGTGCATACCCGGGGGCTGGACTTTGCCTGCGATATCTACATTTGGGCCCCGCTGGCCGGCACTTGCGGCGTGCTCCTG

CTGTCGCTGGTCATCACCCTTTACTGCAAGAGGGGCCGGAAGAAGCTGCTTTACATCTTCAAGCAGCCGTTCATGCGGCCCGT

GCAGACGACTCAGGAAGAGGACGGATGCTCGTGCAGATTCCCTGAGGAGGAAGAGGGGGATGCGAACTGCGCGTCAAGTTCT

CACGGTCCGCCGACGCCCCCGCATATCAACAGGGCCAGAATCAGCTCTACAACGAGCTGAACCTGGGAAGGAGAGAGGAGTAC

GACGTGCTGGACAAGCGACGCGGACGCGACCCGGAGATGGGGGGGAAACCACGGCGGAAAAACCCTCAGGAAGGACTGTACAA

CGAACTCCAGAAAGACAAGATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACTCCCACCCCGG
``` amino acid sequence of LTG2065 (LP-M19217-1-CD8 TM-41BB-CD3 zeta)
SEQ ID NO: 22

```
MLLLVTSLLLCELPHPAFLLIPEVQLVQSGAEVKKPGASVKVSCKASGYTFTSYYMHWVRQAPGQGLEWMGLINPSGGSTSYA

QKFQGRVTMTRDTSTSTVYMELSSLRSEDTAVYYCARSDRGITATDAFDIWGQGTMVTVSSGGGGSGGGGSGGGGSQSVLTQP

PSVSVAPGRMAKITCGGSDIGNKNVHWYQQKPGQAPVLVVYDDYDRPSGIPERFSGSNSGDAATLTISTVEVGDEADYFCQVW

DGSGDPYWMFGGGTQLTVLGAAATTTPAPRPPTPAPTIASQPLSLRPEACRPAAGGAVHTRGLDFACDIYIWAPLAGTCGVLL

LSLVITLYCKRGRKKLLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2066 (LP-M19217-2-CD8 TM-41BB-CD3 zeta)

-continued

SEQ ID NO: 23
```
ATGCTGCTGCTGGTGACCAGCCTGCTGCTGTGCGAACTGCCGCATCCGGCGTTTCTGCTGATTCCGGAGGTCCAGCTGGTACA
GTCTGGAGCTGAGGTGAAGAAGCCTGGGGCCTCAGTGAAGGTCTCCTGCAAGGCTTCCGGATACACCTTCACCAGCTACTACA
TGCACTGGGTGCGACAGGCCCCTGGACAAGGGTTTGAGTGGATGGGATTAATCAACCCTAGTGGTAGTAGCACAAGCTACGCA
CAGAAGTTCCAGGGCAGAGTCACCATGACCAGGGACACGTCCACGAGCACAGTCTACATGGAGCTGAGCAACCTGAGATCTGA
GGACACGGCCGTGTATTACTGTGCGAGATCGGATCGGGGAATTACCGCCACGGACGCTTTTGATATCTGGGGCCAAGGGACAA
TGGTCACCGTCTCTTCAGGCGGAGGAGGCTCCGGGGGAGGAGGTTCCGGGGGCGGGGGTTCCCAGTCTGTGCTGACTCAGCCA
CCCTCGGTGCCAGTGGCCCCAGGGCAGACGGCCAAGATTATCTGTGGGGGAAGTGACATTGGAAATAAAAATGTCCACTGGTA
CCAGCAGAAGCCAGGCCAGGCCCCTGTCCTGGTCGTCTATGATGACTACGACCGGCCCTCAGGGATCCCTGAGCGATTCTCTG
GCTCCAACTCTGGGGACGCGGCCACCCTGACGATCAGCACGGTTGAAGTCGGGGATGAGGCCGACTATTTCTGTCAGGTGTGG
GACGGTAGTGGTGATCCTTATTGGGTGTTCGGCGGAGGGACCCAGCTCACCGTCTTAGGTGCGGCCGCAACTACCACCCCTGC
CCCTCGGCCGCCGACTCCGGCCCCAACCATCGCAAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGGGCCCCGCTGGCCGGCACTTGCGGCGTGCTCCTG
CTGTCGCTGGTCATCACCCTTTACTGCAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGGGGGGATGCGAACTGCGCGTCAAGTTCT
CACGGTCCGCCGACGCCCCCGCATATCAACAGGGCCAGAATCAGCTCTACAACGAGCTGAACCTGGGAAGGAGAGAGGAGTAC
GACGTGCTGGACAAGCGACGCGGACGCGACCCGGAGATGGGGGGGAAACCACGGCGGAAAAACCCTCAGGAAGGACTGTACAA
CGAACTCCAGAAAGACAAGATGGCGGAAGCCTACTCAGAAATCGGGATGAAGGGAGAGCGGAGGAGGGGAAAGGGTCACGACG
GGCTGTACCAGGGACTGAGCACCGCCACTAAGGATACCTACGATGCCTTGCATATGCAAGCACTCCCACCCCGG
``` amino acid sequence of LTG2066 (LP-M19217-2-CD8 TM-41BB-CD3 zeta)
SEQ ID NO: 24
```
MLLLVTSLLLCELPHPAFLLIPEVQLVQSGAEVKKPGASVKVSCKASGYTFTSYYMHWVRQAPGQGFEWMGLINPSGSSTSYA
QKFQGRVTMTRDTSTSTVYMELSNLRSEDTAVYYCARSDRGITATDAFDIWGQGTMVTVSSGGGGSGGGGSGGGGSQSVLTQP
PSVPVAPGQTAKIICGGSDIGNKNVHWYQQKPGQAPVLVVYDDYDRPSGIPERFSGSNSGDAATLTISTVEVGDEADYFCQVW
DGSGDPYWVFGGGTQLTVLGAAATTTPAPRPPTPAPTIASQPLSLRPEACRPAAGGAVHTRGLDFACDIYIWAPLAGTCGVLL
LSLVITLYCKRGRKKLLYIFKQPFMRPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2067 (LP-M19217-7-CD8 TM-41BB-CD3 zeta)
SEQ ID NO: 25
```
ATGCTGCTGCTGGTGACCAGCCTGCTGCTGTGCGAACTGCCGCATCCGGCGTTTCTGCTGATTCCGGAGGTCCAGCTGGTACA
GTCTGGAGCTGAGGTGAACAAGCCTGGTGCCTCAGTGAAGGTCTCCTGCAAGGCTTCTGGATACACCTTCACCAGCTACTATA
TGCACTGGGTGCGACAGGCCCCTGGACAAGGGCTTGAGTGGATGGGAATGATCAACCCTAGTGGTGGTAGCACAAGCTACGCA
CAGAAGTTCCAGGGCAGAGTCACCATGACCAGGGACACGTCCACGAGCACAGTCTACATGGAGCTGAGCAGCCTGAGATCTGA
GGACACGGCCGTGTATTACTGTGCGAGATCGGATCGGGGAATTACCTCCACGGACGCTTTTGATATCTGGGGCCAAGGGACAA
TGGTCACCGTCTCTTCAGGCGGAGGAGGCTCCGGGGGAGGAGGTTCCGGGGGCGGGGGTTCCCAGTCTGTGCTGACTCAGCCA
CCCTCGGTGTCATTGGCCCCAGGGCAGACGGCCAAGATTACCTGTGGGGGAAGTGACATTGGAAATAAAAATGTCCACTGGTA
CCAGCAGAAGCCAGGCCAGGCCCCTGTCCTAGTCGTCTATGATGATTACAACCGGCCCTCAGGGATCCCTGAGCGATTCTCTG
GCTCCAACTCTGGGGACTCAGCCACCCTGACGATCAGCACGGTTGAAGTCGGGGATGAGGCCGACTATTTCTGTCAGGTGTGG
GACGGTAGTGGTGATCCTTATTGGGTGTTCGGCGGAGGGACCCAGCTCACCGTTTTAGGTGCGGCCGCAACTACCACCCCTGC
CCCTCGGCCGCCGACTCCGGCCCCAACCATCGCAAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGGGCCCCGCTGGCCGGCACTTGCGGCGTGCTCCTG
CTGTCGCTGGTCATCACCCTTTACTGCAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGGGGGGATGCGAACTGCGCGTCAAGTTCT
```

```
CACGGTCCGCCGACGCCCCCGCATATCAACAGGGCCAGAATCAGCTCTACAACGAGCTGAACCTGGGAAGGAGAGAGGAGTAC

GACGTGCTGGACAAGCGACGCGGACGCGACCCGGAGATGGGGGGGAAACCACGGCGGAAAAACCCTCAGGAAGGACTGTACAA

CGAACTCCAGAAAGACAAGATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACTCCCACCCCGG
``` amino acid sequence of LTG2067 (LP-M19217-7-CD8 TM-41BB-CD3 zeta)
SEQ ID NO: 26
```
MLLLVTSLLLCELPHPAFLLIPEVQLVQSGAEVNKPGASVKVSCKASGYTFTSYYMHWVRQAPGQGLEWMGMINPSGGSTSYA QKFQGRVTMTRDTSTSTVYMELSSLRSEDTAVYYCARSDRGITSTDAFDIWGQGTMVTVSSGGGGSGGGGSGGGGSQSVLTQP PSVSLAPGQTAKITCGGSDIGNKNVHWYQQKPGQAPVLVVYDDYNRPSGIPERFSGSNSGDSATLTISTVEVGDEADYFCQVW DGSGDPYWVFGGGTQLTVLGAAATTTPAPRPPTPAPTIASQPLSLRPEACRPAAGGAVHTRGLDFACDIYIWAPLAGTCGVLL LSLVITLYCKRGRKKLLYIFKQPFMRPVQTTQEEDGCSCRFPEEEEGGCELRVKFSRSADAPAYQQGQNQLYNELNLGRREEY DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2068 (LP-M19217-23-CD8 TM-41BB-CD3 zeta)
SEQ ID NO: 27
```
ATGCTGCTGCTGGTGACCAGCCTGCTGCTGTGCGAACTGCCGCATCCGGCGTTTCTGCTGATTCCGGAGGTCCAGCTGGTACA GTCTGGAGCTGAGGTGAAGAAGCCTGGGGCCTCAGTGAAGGTCTCCTGCAAGGCATCTGGATACACCTTCACCGGCTACTATA TGCACTGGGTGCGGCAGGCCCCTGGACAAGGGCTTGAGTGGATAGGATTAATCAACCCTAGTGGTGGTAGCACAAGCTACGAA CAGAAGTTCCAGGGCAGAGTCGCCATGACCAGGGACACGTCAACGAGCACAGTCTACATGGAGCTGAGCAGCCTGAGATCTGA GGACACGGCCGTGTATTACTGTGCGAGATCGGATCGGGGAATTACCGCCACGGACGCTTTTGATATCTGGGGCCAAGGGACAA TGGTCACCGTCTCTTCAGGCGGAGGAGGCTCCGGGGGAGGAGGTTCCGGGGGCGGGGGTTCCCAGTCTGTGCTGACTCAGCCA CCCTCGGTGTCAGTGGCCCCAGGGCAGACGGCCAAGATTACCTGTGGGGGAAGTGACATTGGAGATAAAAATGTCCACTGGTA CCAGCAGAAGCCAGGCCAGGCCCCTGTCCTGGTCGTCTATGATGATTACGACCGGCCCTCAGGGATCCCTGAGCGATTCTCTG GCTCCAACTCTGGGGACGCGGCCACCCTGACGATCAGCACGGTCGAAGTCGGGGATGAGGCCGACTATTTCTGTCAGGTGTGG GACGGTATTGGTGATCCCTATTGGGTGTTCGGCGGAGGGACCCAGCTCACCGTTTTAGGTGCGGCCGCAACTACCACCCCTGC CCCTCGGCCGCCGACTCCGGCCCCAACCATCGCAAGCCAACCCCTCTCCTTGCGCCCCGAAGCTTGCCGCCCGGCCGCGGGTG GAGCCGTGCATACCCGGGGGCTGGACTTTGCCTGCGATATCTACATTTGGGCCCCGCTGGCCGGCACTTGCGGCGTGCTCCTG CTGTCGCTGGTCATCACCCTTTACTGCAAGAGGGGCCGGAAGAAGCTGCTTTACATCTTCAAGCAGCCGTTCATGCGGCCCGT GCAGACGACTCAGGAAGAGGACGGATGCTCGTGCAGATTCCCTGAGGAGGAAGAGGGGGGATGCGAACTGCGCGTCAAGTTCT CACGGTCCGCCGACGCCCCCGCATATCAACAGGGCCAGAATCAGCTCTACAACGAGCTGAACCTGGGAAGGAGAGAGGAGTAC GACGTGCTGGACAAGCGACGCGGACGCGACCCGGAGATGGGGGGGAAACCACGGCGGAAAAACCCTCAGGAAGGACTGTACAA CGAACTCCAGAAAGACAAGATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACTCCCACCCCGG
``` amino acid sequence of LTG2068 (LP-M19217-23-CD8 TM-41BB-CD3 zeta)
SEQ ID NO: 28
```
MLLLVTSLLLCELPHPAFLLIPEVQLVQSGAEVKKPGASVKVSCKASGYTFTGYYMHWVRQAPGQGLEWIGLINPSGGSTSYE QKFQGRVAMTRDTSTSTVYMELSSLRSEDTAVYYCARSDRGITATDAFDIWGQGTMVTVSSGGGGSGGGGSGGGGSQSVLTQP PSVSVAPGQTAKITCGGSDIGDKNVHWYQQKPGQAPVLVVYDDYDRPSGIPERFSGSNSGDAATLTISTVEVGDEADYFCQVW DGIGDPYWVFGGGTQLTVLGAAATTTPAPRPPTPAPTIASQPLSLRPEACRPAAGGAVHTRGLDFACDIYIWAPLAGTCGVLL LSLVITLYCKRGRKKLLYIFKQPFMRPVQTTQEEDGCSCRFPEEEEGGCELRVKFSRSADAPAYQQGQNQLYNELNLGRREEY DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2069 (LP-M19217-29-CD8 TM-41BB-CD3 zeta)
SEQ ID NO: 29
```
ATGCTGCTGCTGGTGACCAGCCTGCTGCTGTGCGAACTGCCGCATCCGGCGTTTCTGCTGATTCCGGAGGTCCAGCTAGTACA GTCTGGAGCTGAGGTGAAGAAGCCTGGGGCCTCAGTGAAGGTCTCCTGCAAGGCTTCTGGATACACCTTCACCAGCTACTATA TGCACTGGGTGCGACAGGCCCCTGGACAAGGGCTTGAGTGGATGGGAATGATCAACCCTAGTGGTGGTAGCACAAGCTACGCA
```

-continued

```
CAGAAGTTCCAGGGCAGAGTCACCATGACCAGGGACACGTCCACGAGCACAGTCTACATGGAGCTGAGCAGCCTGAGATCTGA
GGACACGGCCGTGTATTACTGTGCGAGATCGGATCGGGGAATTACCGCCACGGACGCTTTTGATATCTGGGGCCAAGGGACAA
TGGTCACCGTCTCTTCAGGCGGAGGAGGCTCCGGGGGAGGAGGTTCCGGGGGCGGGGGTTCCCAGTCTGTGCTGACTCAGCCA
CCCTCGGTGTCAGTGGCCCCAGGGCAGACGGCCAAGATTACCTGTGGGGGAAGTGACATTGGAAATAAAAATGCCCACTGGTA
CCAGCAGAAGCCAGGCCAGGCCCCTGTCCTGGTCGTCTATGATGATTACGACCGGCCCTCAGGGATCTCTGAGCGATTCTCTG
GCTCCAACTCTGGGGACGCGGCCACCCTGACGATCAGCACGGTCGAAGTCGGGGATGAGGCCGACTATTTCTGTCAGGTGTGG
GACGGTAGTGGTGATCCTTTTTGGGTGTTCGGCGGAGGGACCCAGCTCACCGTTTTAGGTGCGGCCGCAACTACCACCCCTGC
CCCTCGGCCGCCGACTCCGGCCCCAACCATCGCAAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGGGCCCCGCTGGCCGGCACTTGCGGCGTGCTCCTG
CTGTCGCTGGTCATCACCCTTTACTGCAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGGGGGATGCGAACTGCGCGTCAAGTTCT
CACGGTCCGCCGACGCCCCCGCATATCAACAGGGCCAGAATCAGCTCTACAACGAGCTGAACCTGGGAAGGAGAGAGGAGTAC
GACGTGCTGGACAAGCGACGCGGACGCGACCCGGAGATGGGGGGGAAACCACGGCGGAAAAACCCTCAGGAAGGACTGTACAA
CGAACTCCAGAAAGACAAGATGGCGGAAGCCTACTCAGAAATCGGGATGAAGGGAGAGCGGAGGAGGGGAAAGGGTCACGACG
GGCTGTACCAGGGACTGAGCACCGCCACTAAGGATACCTACGATGCCTTGCATATGCAAGCACTCCCACCCCGG
``` amino acid sequence of LTG2069 (LP-M19217-29-CD8 TM-41BB-CD3 zeta)

SEQ ID NO: 30

```
MLLLVTSLLLCELPHPAFLLIPEVQLVQSGAEVKKPGASVKVSCKASGYTFTSYYMHWVRQAPGQGLEWMGMINPSGGSTSYA
QKFQGRVTMTRDTSTSTVYMELSSLRSEDTAVYYCARSDRGITATDAFDIWGQGTMVTVSSGGGGSGGGGSGGGGSQSVLTQP
PSVSVAPGQTAKITCGGSDIGNKNAHWYQQKPGQAPVLVVYDDYDRPSGISERFSGSNSGDAATLTISTVEVGDEADYFCQVW
DGSGDPFWVFGGGTQLTVLGAAATTTPAPRPPTPAPTIASQPLSLRPEACRPAAGGAVHTRGLDFACDIYIWAPLAGTCGVLL
LSLVITLYCKRGRKKLLYIFKQPFMRPVQTTQEEDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRRGKGHDGLYQGLSTATKDTYDALHMQALPPR
``` nucleotide sequence of LTG2070 (LP-M19217-38-CD8 TM-41BB-CD3 zeta)

SEQ ID NO: 31

```
ATGCTGCTGCTGGTGACCAGCCTGCTGCTGTGCGAACTGCCGCATCCGGCGTTTCTGCTGATTCCGGAGGTCCAGCTGGTACA
GTCTGGAGCTGAGGTGAAGAGGCCTGGGGCCTCAGTGAAGGTCTCCTGCAAGGCTTCTGGATACACCTTCACCAGCTACTATA
TGCACTGGGTGCGACAGGCCCCTGGACGAGGGCTTGAGTGGATGGGATTAATCAACCCTAGTGGTGGTAGCACAAGCTACGCA
CAGGAGTTCCAGGGCAGAGTCACCATGACCAGGGACATGTCCACGAGCACAGTCTACATGGAGCTGAGCAGCCTGAGATCTGA
GGACACGGCCGTGTATTACTGTGCGAGATCGGATCGGGGAATTAGCGCCACGGACGCTTTTGATATCTGGGGCCAAGGGACAA
TGGTCACCGTCTCTTCAGGCGGAGGAGGCTCCGGGGGAGGAGGTTCCGGGGGCGGGGGTTCCCAGTCTGTGCTGACTCAGCCA
CCCTCGGTGTCAGTGGCCCCAGGGCAGATGGCCAAGATTACCTGTGGGGGAAGTGACATTGGAAATAAAAATGTCCACTGGTA
CCAGCAGAAGCCAGGCCAGGCCCCTGTCCTGGTCGTCTATGATGATTACAACCGGCCCTCAGGGATCCCTGAGCGATTCTCTG
GCTCCAACTCTGGGGACGCGGCCACCCTGACGATCAGCACGGTCGAAGTCGGGGATGAGGCCGACTATTTCTGTCAGGTATGG
GACGGTAGTGGTGATCCTTATTGGGTGTTCGGCGGAGGGACCCAGCTCACCGATTTAGGTGCGGCCGCAACTACCACCCCTGC
CCCTCGGCCGCCGACTCCGGCCCCAACCATCGCAAGCCAACCCCTCTCCTTGCGCCCCGAAGCTTGCCGCCCGGCCGCGGGTG
GAGCCGTGCATACCCGGGGGCTGGACTTTGCCTGCGATATCTACATTTGGGCCCCGCTGGCCGGCACTTGCGGCGTGCTCCTG
CTGTCGCTGGTCATCACCCTTTACTGCAAGAGGGGCCGGAAGAAGCTGCTTTACATCTTCAAGCAGCCGTTCATGCGGCCCGT
GCAGACGACTCAGGAAGAGGACGGATGCTCGTGCAGATTCCCTGAGGAGGAAGAGGGGGATGCGAACTGCGCGTCAAGTTCT
CACGGTCCGCCGACGCCCCCGCATATCAACAGGGCCAGAATCAGCTCTACAACGAGCTGAACCTGGGAAGGAGAGAGGAGTAC
GACGTGCTGGACAAGCGACGCGGACGCGACCCGGAGATGGGGGGGAAACCACGGCGGAAAAACCCTCAGGAAGGACTGTACAA
CGAACTCCAGAAAGACAAGATGGCGGAAGCCTACTCAGAAATCGGGATGAAGGGAGAGCGGAGGAGGGGAAAGGGTCACGACG
```

-continued

GGCTGTACCAGGGACTGAGCACCGCCACTAAGGATACCTACGATGCCTTGCATATGCAAGCACTCCCACCCCGG amino acid sequence of LTG2070 (LP-M19217-38-CD8 TM-41BB-CD3 zeta)
SEQ ID NO: 32

MLLLVTSLLLCELPHPAFLLIPEVQLVQSGAEVKRPGASVKVSCKASGYTFTSYYMHWVRQAPGRGLEWMGLINPSGGSTSYA

QEFQGRVTMTRDMSTSTVYMELSSLRSEDTAVYYCARSDRGISATDAFDIWGQGTMVTVSSGGGGSGGGGSGGGGSQSVLTQP

PSVSVAPGQMAKITCGGSDIGNKNVHWYQQKPGQAPVLVVYDDYNRPSGIPERFSGSNSGDAATLTISTVEVGDEADYFCQVW

DGSGDPYWVFGGGTQLTDLGAAATTTPAPRPPTPAPTIASQPLSLRPEACRPAAGGAVHTRGLDFACDIYIWAPLAGTCGVLL

LSLVITLYCKRGRKKLLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDTYDALHMQALPPR nucleotide sequence of LTG2071 (LP-M19217-40-CD8 TM-41BB-CD3 zeta)
SEQ ID NO: 33

ATGCTGCTGCTGGTGACCAGCCTGCTGCTGTGCGAACTGCCGCATCCGGCGTTTCTGCTGATTCCGGAGGTCCAGCTGGTACA

GTCTGGAGCTGAGGTGAAGAGGCCTGGGGCCTCAGTGAAGGTCTCCTGCAAGGCTTCTGGATACACCTTCACCAGCTACTATA

TGCACTGGGTGCGACAGGCCCCTGGACAAGGGCTTGTGTGGATGGGATTAATCAACCCTAGTGGTGGCAGCACAAGCTACGCA

CAGAAGTTCCAGGGCAGAGTCACCATGACCAGGGACACGTCCACGAGCACAGTCTACATGGAGCTGAGCAGCCTGAGATCTGA

GGACACGGCCGTGTATTACTGTGCGAGATCGGATCGGGGAATTACCGCCACGGACGCTTTTGATATCTGGGGCCAAGGGACAA

TGGTCACCGTCTCTTCAGGCGGAGGAGGCTCCGGGGGAGGAGGTTCCGGGGGCGGGGGTTCCCAGTCTGTGCTGACTCAGCCA

CCCTCGGTCTCAGTGGCCCCAGGGCAGACGGCCAAGACTACCTGTGGGGGAAGTGACATTGGAAATAAAAATGTCCACTGGTA

CCAGCAGAAGCCAGGCCAGGCCCCTGTCCTGGTCGTCTATGATGATTACGACCGGCCCTCAGGGATCCCTGAGCGATTCTCTG

GCTCCAACTCTGGGGACGCGGCCACCCTGACGATCAGCACGGTCGAAGTCGGGGATGAGGCCGACTATGTCTGTCAGGTGTGG

GACGGTAGTGGTGATCCTTATTGGGTGTTCGGCGGAGGGACCCAGCTCACCGTTTTAGGTGCGGCCGCAACTACCACCCCTGC

CCCTCGGCCGCCGACTCCGGCCCCAACCATCGCAAGCCAACCCCTCTCCTTGCGCCCCGAAGCTTGCCGCCCGGCCGCGGGTG

GAGCCGTGCATACCCGGGGGCTGGACTTTGCCTGCGATATCTACATTTGGGCCCCGCTGGCCGGCACTTGCGGCGTGCTCCTG

CTGTCGCTGGTCATCACCCTTTACTGCAAGAGGGGCCGGAAGAAGCTGCTTTACATCTTCAAGCAGCCGTTCATGCGGCCCGT

GCAGACGACTCAGGAAGAGGACGGATGCTCGTGCAGATTCCCTGAGGAGGAAGAGGGGGGATGCGAACTGCGCGTCAAGTTCT

CACGGTCCGCCGACGCCCCCGCATATCAACAGGGCCAGAATCAGCTCTACAACGAGCTGAACCTGGGAAGGAGAGAGGAGTAC

GACGTGCTGGACAAGCGACGCGGACGCGACCCGGAGATGGGGGGGAAACCACGGCGGAAAAACCCTCAGGAAGGACTGTACAA

CGAACTCCAGAAAGACAAGATGGCGGAAGCCTACTCAGAAATCGGGATGAAGGGAGAGCGGAGGAGGGGAAAGGGTCACGACG

GGCTGTACCAGGGACTGAGCACCGCCACTAAGGATACCTACGATGCCTTGCATATGCAAGCACTCCCACCCCGG amino acid sequence of LTG2071 (LP-M19217-40-CD8 TM-41BB-CD3 zeta)
SEQ ID NO: 34

MLLLVTSLLLCELPHPAFLLIPEVQLVQSGAEVKRPGASVKVSCKASGYTFTSYYMHWVRQAPGQGLVWMGLINPSGGSTSYA

QKFQGRVTMTRDTSTSTVYMELSSLRSEDTAVYYCARSDRGITATDAFDIWGQGTMVTVSSGGGGSGGGGSGGGGSQSVLTQP

PSVSVAPGQTAKTTCGGSDIGNKNVHWYQQKPGQAPVLVVYDDYDRPSGIPERFSGSNSGDAATLTISTVEVGDEADYVCQVW

DGSGDPYWVFGGGTQLTVLGAAATTTPAPRPPTPAPTIASQPLSLRPEACRPAAGGAVHTRGLDFACDIYIWAPLAGTCGVLL

LSLVITLYCKRGRKKLLYIFKQPFMRPVQTTQEEDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRRGKGHDGLYQGLSTATKDTYDALHMQALPPR nucleotide sequence of DNA CD8 transmembrane domain
SEQ ID NO: 35 atttgggccccgctggccggcacttgcggcgtgctcctgctgtcgctggtcatcacccttactgc amino acid sequence of CD8 transmembrane domain
SEQ ID NO: 36

IWAPLAGTCGVLLLSLVITLYC nucleotide sequence of DNA CD8 hinge domain

-continued actaccaccctgcccctcggccgccgactccggccccaaccatcgcaagccaaccctctccttgcgccccgaagcttgccg cccggccgcgggtggagccgtgcatacccgggggctggactttgcctgcgatatctac amino acid sequence of CD8 hinge domain

SEQ ID NO: 38

TTTPAPRPPTPAPTIASQPLSLRPEACRPAAGGAVHTRGLDFACDIY amino acid sequence of amino acid numbers 137 to 206 hinge and transmembrane region of CD8.alpha. (NCBIRefSeq: NP.sub.--001759.3)

SEQ ID NO: 39

TTTPAPRPPTPAPTIASQPLSLRPEACRPAAGGAVHTRGLDFACDIYIWAPLAGTCGVLLLSLVITLYC nucleotide sequence of DNA signaling domain of 4-1BB

SEQ ID NO: 40 aagaggggccggaagaagctgctttacatcttcaagcagccgttcatgcggcccgtgcagacgactcaggaagaggacggatg ctcgtgcagattccctgaggaggaagagggggatgcgaactg amino acid sequence of signaling domain of 4-1BB

SEQ ID NO: 41

KRGRKKLLYIFKQPFMRPVQTTQEEDGCSCRFPEEEEGGCEL nucleotide sequence of intracellular signaling domain of CD3-zeta

SEQ ID NO: 42 cgcgtcaagttctcacggtccgccgacgcccccgcatatcaacagggccagaatcagctctacaacgagctgaacctgggaag gagagaggagtacgacgtgctggacaagcgacgcggacgcgacccggagatgggggggaaaccacggcggaaaaaccctcagg aaggactgtacaacgaactccagaaagacaagatggcggaagcctactcagaaatcgggatgaagggagagcggaggagggga aagggtcacgacgggctgtaccagggactgagcaccgccactaaggatacctacgatgccttgcatatgcaagcactcccacc ccgg amino acid sequence of CD3-zeta

SEQ ID NO: 43

RVKFSRSADAPAYQQGQNQLYNELNLGRREEYDVLDKRRGRDPEMGGKPRRKNPQEGLYNELQKDKMAEAYSEIGMKGERRRG

KGHDGLYQGLSTATKDTYDALHMQALPPR nucleotide sequence of intracellular signaling domain of CD3-zeta variant

SEQ ID NO: 44 cgcgtcaagttctcacggtccgccgacgcccccgcatataaacagggccagaatcagctctacaacgagctgaacctgggaag gagagaggagtacgacgtgctggacaagcgacgcggacgcgacccggagatgggggggaaaccacggcggaaaaaccctcagg aaggactgtacaacgaactccagaaagacaagatggcggaagcctactcagaaatcgggatgaagggagagcggaggagggga aagggtcacgacgggctgtaccagggactgagcaccgccactaaggatacctacgatgccttgcatatgcaagcactcccacc ccgg amino acid sequence of CD3-zeta signaling domain variant

SEQ ID NO: 45

RVKFSRSADAPAYKQGQNQLYNELNLGRREEYDVLDKRRGRDPEMGGKPRRKNPQEGLYNELQKDKMAEAYSEIGMKGERRRG

KGHDGLYQGLSTATKDTYDALHMQALPPR nucleotide sequence of ScFv CD19 (FMC63)

SEQ ID NO: 46 gacattcagatgactcagaccacctcttccttgtccgcgtcactgggagacagagtgaccatctcgtgtcgcgcaagccagga tatctccaagtacctgaactggtaccaacagaagcccgacgggactgtgaagctgctgatctaccacacctcacgcctgcaca gcggagtgccaagcagattctccggctccggctcgggaaccgattactcgcttaccattagcaacctcgagcaggaggacatc gctacctacttctgccagcaaggaaataccctgccctacaccttcggcggaggaaccaaattggaaatcaccggcggaggagg ctccggggggaggaggttccgggggcggggggttccgaagtgaagctccaggagtccggccccggcctggtggcgccgtcgcaat cactctctgtgacctgtaccgtgtcgggagtgtccctgcctgattacggcgtgagctggattcggcagccgccgcggaagggc ctggaatggctgggtgtcatctggggatccgagactacctactacaactcggccctgaagtcccgcctgactatcatcaaaga caactcgaagtcccaggtctttctgaagatgaactccctgcaaactgacgacaccgccatctattactgtgctaagcactact actacggtggaagctatgctatggactactggggcaaggcacttcggtgactgtgtcaagc amino acid sequence of ScFv CD19 (FMC63)

-continued nucleotide sequence of anti-CD33 ScFv (LTG1936)
SEQ ID NO: 48
CAGGTGCAGCTGGTGCAATCTGGGGCAGAGGTGAAAAAGCCCGGGGAGTCTCTGAGGATCTCCTGTAAGGGTTCTGGATTCAG
TTTTCCCACCTACTGGATCGGCTGGGTGCGCCAGATGCCCGGGAAAGGCCTGGAGTGGATGGGGATCATCTATCCTGGTGACT
CTGATACCAGATACAGCCCGTCCTTCCAAGGCCAGGTCACCATCTCAGCCGACAAGTCCATCAGCACCGCCTACCTGCAGTGG
AGCAGCCTGAAGGCCTCGGACACCGCCATGTATTACTGTGCGAGACTAGTTGGAGATGGCTACAATACGGGGGCTTTTGATAT
CTGGGGCCAAGGGACAATGGTCACCGTCTCTTCAGGAGGTGGCGGGTCTGGTGGTGGCGGTAGCGGTGGTGGCGGATCCGATA
TTGTGATGACCCACACTCCACTCTCTCTGTCCGTCACCCCTGGACAGCCGGCCTCCATCTCCTGCAAGTCTAGTCAGAGCCTC
CTGCATAGTAATGGAAAGACCTATTTGTATTGGTACCTGCAGAAGCCAGGCCAGCCTCCACAGCTCCTGATCTATGGAGCTTC
CAACCGGTTCTCTGGAGTGCCAGACAGGTTCAGTGGCAGCGGGTCAGGGACAGATTTCACACTGAAAATCAGCCGGGTGGAGG
CTGAGGATGTTGGGGTTTATTACTGCATGCAAAGTATACAGCTTCCTATCACCTTCGGCCAAGGGACACGACTGGAGATTAAA amino acid sequence of anti-CD33 ScFv (LTG1936)
SEQ ID NO: 49
QVQLVQSGAEVKKPGESLRISCKGSGFSFPTYWIGWVRQMPGKGLEWMGIIYPGDSDTRYSPSFQGQVTISADKSISTAYLQW
SSLKASDTAMYYCARLVGDGYNTGAFDIWGQGTMVTVSSGGGGSGGGGSGGGGSDIVMTHTPLSLSVTPGQPASISCKSSQSL
LHSNGKTYLYWYLQKPGQPPQLLIYGASNRFSGVPDRFSGSGSGTDFTLKISRVEAEDVGVYYCMQSIQLPITFGQGTRLEIK nucleotide sequence of anti-mesothelin ScFv (LTG1904)
SEQ ID NO: 50
GAGGTCCAGCTGGTACAGTCTGGGGGAGGCTTGGTACAGCCTGGGGGGTCCCTGAGACTCTCCTGTGCAGCCTCTGGATTCAC
CTTTGATGATTATGCCATGCACTGGGTCCGGCAAGCTCCAGGGAAGGGCCTGGAGTGGGTCTCAGGTATTAGTTGGAATAGTG
GTAGCATAGGCTATGCGGACTCTGTGAAGGGCCGATTCACCATCTCCAGAGACAACGCCAAGAACTCCCTGTATCTGCAAATG
AACAGTCTGAGAGCTGAGGACACGGCCTTGTATTACTGTGCAAAAGATTATCGTCAGTGGCTGGACCCTTTAACTACTGGGG
CCAGGGCACCCTGGTCACCGTCTCCTCAGGAGGTGGCGGGTCTGGTGGAGGCGGTAGCGGCGGTGGCGGATCCTCTTCTGAGC
TGACTCAGGACCCTGCTGTGTCTGTGGCCTTGGGACAGACAGTCAGGATCACATGCAAGGAGACAGCCTCAGAAGCTATTAT
GCAAGCTGGTACCAGCAGAAGCCAGGACAGGCCCCTGTACTTGTCATCTATGGTAAAAACAACCGGCCCTCAGGGATCCCAGA
CCGATTCTCTGGCTCCAGCTCAGGAAACACAGCTTCCTTGACCATCACTGGGGCTCAGGCGGAGGATGAGGCTGACTATTACT
GTAACTCCCGGGACAGCAGTGGTAACCATCTGGTATTCGGCGGAGGCACCCAGCTGACCGTCCTCGGT amino acid sequence of anti-mesothelin ScFv (LTG1904)
SEQ ID NO: 51
EVQLVQSGGGLVQPGGSLRLSCAASGFTFDDYAMHWVRQAPGKGLEWVSGISWNSGSIGYADSVKGRFTISRDNAKNSLYLQM
NSLRAEDTALYYCAKDLSSVAGPFNYWGQGTLVTVSSGGGGSGGGGSGGGGSSSELTQDPAVSVALGQTVRITCQGDSLRSYY
ASWYQQKPGQAPVLVIYGKNNRPSGIPDRFSGSSSGNTASLTITGAQAEDEADYYCNSRDSSGNHLVFGGGTQLTVLG

---

What is claimed is:

1. A method of treating CD19-expressing cancer in a subject in need thereof, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises the amino acid sequence of SEQ ID NO: 20, 22, 24, 26, 28, 30, 32, or 34.

2. The method of claim 1, wherein the cancer is a hematological cancer.

3. The method of claim 2, wherein the hematological cancer is leukemia, lymphoma, or multiple myeloma.

4. The method of claim 3, wherein the leukemia is chronic lymphocytic leukemia (CLL), acute lymphocytic leukemia (ALL), or chronic myelogenous leukemia (CML).

5. The method of claim 3, wherein the lymphoma is mantle cell lymphoma, non-Hodgkin's lymphoma or Hodgkin's lymphoma.

6. The method of claim 1, wherein the cancer is an adult carcinoma selected from the group consisting of an oral and pharynx cancer, digestive system cancers, respiratory system cancers, bones and joint cancers, soft tissue cancers, skin cancers, pediatric tumors, tumors of the central nervous system, and cancers of the breast, the genital system, the urinary system, the eye and orbit, the endocrine system, and the brain and other nervous system, or any combination thereof.

* * * * *

SEQUENCE LISTING

<160> NUMBER OF SEQ IDS: 51

<210> SEQ ID NO 1
<211> LENGTH: 741
<212> TYPE: DNA
<213> ORGANISM: Artificial Sequence
<220> FEATURE:
<223> OTHER INFORMATION: CD19-reactive ScFv1 binding domain (LTG2050)

<400> SEQUENCE: 1
gaggtccagc tggtacagtc tggagctgag gtgaagaagc tggggcctc agtgaaggtc      60

```
tcctgcaagg cttctggata caccttcacc agctactata tgcactgggt gcgacaggcc    120
cctggacaag ggcttgagtg gatgggaata atcaacccta gtggtggtag cacaagctac    180
gcacagaagt tccagggcag agtcaccatg accagggaca cgtccacgag cacagtctac    240
atggagctga gcagcctgag atctgaggac acggccgtgt attactgtgc gagatcggat    300
cggggaatta ccgccacgga cgcttttgat atctggggcc aagggacaat ggtcaccgtc    360
tcttcaggag gtggcgggtc tggtggaggc ggtagcggtg gtggcggatc ccagtctgtg    420
ctgactcagc cacccctcgt gtcagtggcc cagggcagac ggccaagat tacctgtggg    480 ggaagtgaca ttggaaataa aaatgtccac tggtaccagc agaagccagg ccaggcccct    540
gtcctggtcg tctatgatga ttacgaccgg ccctcaggga tccctgagcg attctctggc    600
tccaactctg ggacgcggc caccctgacg atcagcacgg tcgaagtcgg ggatgaggcc    660
gactatttct gtcaggtgtg ggacagtagt ggtgatcctt attgggtgtt cggcggaggg    720
acccagctca ccgttttagg t                                              741
```

```
<210> SEQ ID NO 2
<211> LENGTH: 247
<212> TYPE: PRT
<213> ORGANISM: Artificial Sequence
<220> FEATURE:
<223> OTHER INFORMATION: CD19-reactive ScFv1 binding domain (LTG2050)

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Ser Gly Gly Gly Ser Gln Ser Val Leu Thr Gln Pro
    130                 135                 140

Pro Ser Val Ser Val Ala Pro Gly Gln Thr Ala Lys Ile Thr Cys Gly
145                 150                 155                 160

Gly Ser Asp Ile Gly Asn Lys Asn Val His Trp Tyr Gln Gln Lys Pro
                165                 170                 175

Gly Gln Ala Pro Val Leu Val Val Tyr Asp Asp Tyr Asp Arg Pro Ser
            180                 185                 190

Gly Ile Pro Glu Arg Phe Ser Gly Ser Asn Ser Gly Asp Ala Ala Thr
        195                 200                 205

Leu Thr Ile Ser Thr Val Glu Val Gly Asp Glu Ala Asp Tyr Phe Cys
    210                 215                 220

Gln Val Trp Asp Ser Ser Gly Asp Pro Tyr Trp Val Phe Gly Gly Gly
225                 230                 235                 240
```

Thr Gln Leu Thr Val Leu Gly
            245

<210> SEQ ID NO 3
<211> LENGTH: 741
<212> TYPE: DNA
<213> ORGANISM: Artificial Sequence
<220> FEATURE:
<223> OTHER INFORMATION: CD19-reactive ScFv2 binding domain (LTG2065)

<400> SEQUENCE: 3

```
gaggtccagc tggtacagtc tggagctgag gtgaagaagc ctggggcctc agtgaaggtc      60
tcctgcaagg cttctggata caccttcacc agctactata tgcactgggt gcgacaggcc     120
cctggacaag gcttgagtg gatgggatta atcaaccta gtggtggtag cacaagctac       180
gcacagaagt tccagggcag agtcaccatg accaggaca cgtccacgag cacagtctac      240
atggagctga gcagcctgag atctgaggac acggccgtgt attactgtgc gagatcggat     300
cggggaatta ccgccacgga cgcttttgat atctggggcc aagggacaat ggtcaccgtc     360
tcttcaggcg aggaggctc cggggagga ggttccgggg cgggggttc ccagtctgtg         420 ctgactcagc caccctcggt gtcagtggcc ccagggcgga tggccaagat acctgtgggg     480
ggaagtgaca ttggaaataa aaatgtccac tggtatcagc agaagccagg ccaggcccct     540
gtcctggttg tctatgatga ttcgaccggg ccctcaggga tccctgagcg attctctggc     600
tccaactctg ggacgcggc caccctgacg atcagcacgg tcgaagtcgg ggatgaggcc      660
gactatttct gtcaggtgtg ggacggtagt ggtgatcctt attggatgtt cggcggaggg     720
acccagctca ccgttttagg t                                                741
```

<210> SEQ ID NO 4
<211> LENGTH: 247
<212> TYPE: PRT
<213> ORGANISM: Artificial Sequence
<220> FEATURE:
<223> OTHER INFORMATION: CD19-reactive ScFv2 binding domain (LTG2065)

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Leu Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Gln Ser Val Leu Thr Gln Pro
    130                 135                 140

Pro Ser Val Ser Val Ala Pro Gly Arg Met Ala Lys Ile Thr Cys Gly
145                 150                 155                 160

Gly Ser Asp Ile Gly Asn Lys Asn Val His Trp Tyr Gln Lys Pro
            165                 170                 175

Gly Gln Ala Pro Val Leu Val Val Tyr Asp Asp Tyr Asp Arg Pro Ser
        180                 185                 190

Gly Ile Pro Glu Arg Phe Ser Gly Ser Asn Ser Gly Asp Ala Ala Thr
    195                 200                 205

Leu Thr Ile Ser Thr Val Glu Val Gly Asp Glu Ala Asp Tyr Phe Cys
    210                 215                 220

Gln Val Trp Asp Gly Ser Gly Asp Pro Tyr Trp Met Phe Gly Gly Gly
225                 230                 235                 240

Thr Gln Leu Thr Val Leu Gly
                245

<210> SEQ ID NO 5
<211> LENGTH: 741
<212> TYPE: DNA
<213> ORGANISM: Artificial Sequence
<220> FEATURE:
<223> OTHER INFORMATION: CD19-reactive ScFv3 binding domain (LTG2066)

<400> SEQUENCE: 5

```
gaggtccagc tggtacagtc tggagctgag gtgaagaagc tggggcctc  agtgaaggtc      60
tcctgcaagg cttccggata caccttcacc agctactaca tgcactgggt gcgacaggcc     120
cctggacaag ggtttgagtg gatgggatta atcaaccctc gtggtagtag cacaagctac     180
gcacagaagt tccagggcag agtcaccatg accagggaca cgtccacgag cacagtctac     240
atggagctga gcaacctgag atctgaggac acggccgtgt attactgtgc gagatcggat     300
cggggaatta ccgccacgga cgcttttgat atctggggcc aagggacaat ggtcaccgtc     360
tcttcaggcg gaggaggctc cggggaggga ggttccgggg cggggttc  ccagtctgtg     420
ctgactcagc acccctcggt gccagtggcc cagggcaga cggccaagat tatctgtggg     480
ggaagtgaca ttggaaataa aaatgtccac tggtaccagc agaagccagg ccaggcccct     540
gtcctggtcg tctatgatga ctacgaccgg ccctcaggga tccctgagcg attctctggc     600
tccaactctg ggacgcggc  cacctgacg  atcagcacgg ttgaagtcgg ggatgaggcc     660
gactatttct gtcaggtgtg ggacggtagt ggtgatcctt attgggtgtt cggcggaggg     720
acccagctca ccgtcttagg t                                                 741
```

<210> SEQ ID NO 6
<211> LENGTH: 247
<212> TYPE: PRT
<213> ORGANISM: Artificial Sequence
<220> FEATURE:
<223> OTHER INFORMATION: CD19-reactive ScFv3 binding domain (LTG2066)

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Phe Glu Trp Met
        35                  40                  45

Gly Leu Ile Asn Pro Ser Gly Ser Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Asn Leu Arg Ser Glu Asp Thr Ala Val Tyr Tyr Cys
            85                  90                  95

Ala Arg Ser Asp Arg Gly Ile Thr Ala Thr Asp Ala Phe Asp Ile Trp
        100                 105                 110

Gly Gln Gly Thr Met Val Thr Val Ser Gly Gly Gly Gly Ser Gly
        115                 120                 125

Gly Gly Gly Ser Gly Gly Gly Ser Gln Ser Val Leu Thr Gln Pro
        130                 135                 140

Pro Ser Val Pro Val Ala Pro Gly Gln Thr Ala Lys Ile Ile Cys Gly
145                 150                 155                 160

Gly Ser Asp Ile Gly Asn Lys Asn Val His Trp Tyr Gln Gln Lys Pro
                165                 170                 175

Gly Gln Ala Pro Val Leu Val Val Tyr Asp Asp Tyr Asp Arg Pro Ser
            180                 185                 190

Gly Ile Pro Glu Arg Phe Ser Gly Ser Asn Ser Gly Asp Ala Ala Thr
            195                 200                 205

Leu Thr Ile Ser Thr Val Glu Val Gly Asp Glu Ala Asp Tyr Phe Cys
        210                 215                 220

Gln Val Trp Asp Gly Ser Gly Asp Pro Tyr Trp Val Phe Gly Gly Gly
225                 230                 235                 240

Thr Gln Leu Thr Val Leu Gly
                245

<210> SEQ ID NO 7
<211> LENGTH: 741
<212> TYPE: DNA
<213> ORGANISM: Artificial Sequence
<220> FEATURE:
<223> OTHER INFORMATION: CD19-reactive ScFv4 binding domain (LTG2067)

<400> SEQUENCE: 7
gaggtccagc tggtacagtc tggagctgag gtgaacaagc ctggtgcctc agtgaaggtc      60
tcctgcaagg cttctggata caccttcacc agctactata tgcactgggt gcgacaggcc     120
cctggacaag gcttgagtg gatgggaatg atcaacccta gtggtggtag cacaagctac      180
gcacagaagt tccagggcag agtcaccatg accagggaca cgtccacgag cacagtctac     240
atggagctga gcagcctgag atctgaggac acggccgtgt attactgtgc gagatcggat     300
cggggaatta cctccacgga cgcttttgat atctggggcc aagggacaat ggtcaccgtc     360
tcttcaggcg gaggaggctc cggggggagga ggttccgggg gcgggggttc ccagtctgtg    420
ctgactcagc caccctcggt gtcattggcc ccagggcaga cggccaagat tacctgtggg     480
ggaagtgaca ttggaaataa aaatgtccac tggtaccagc agaagccagg ccaggcccct    540
gtcctagtcg tctatgatga ttacaaccgg ccctcaggga tccctgagcg attctctggc    600
tccaactctg gggactcagc caccctgacg atcagcacgg tcgaagtcgg ggatgaggcc    660
gactatttct gtcaggtgtg ggacggtagt ggtgatcctt attgggtgtt cggcggaggg    720
acccagctca ccgttttagg t                                              741

<210> SEQ ID NO 8
<211> LENGTH: 247
<212> TYPE: PRT
<213> ORGANISM: Artificial Sequence
<220> FEATURE:
<223> OTHER INFORMATION: CD19-reactive ScFv4 binding domain (LTG2067)

<400> SEQUENCE: 8

```
Glu Val Gln Leu Val Gln Ser Gly Ala Glu Val Asn Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Met Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Asp Arg Gly Ile Thr Ser Thr Asp Ala Phe Asp Ile Trp
            100                 105                 110
Gly Gln Gly Thr Met Val Thr Val Ser Ser Gly Gly Gly Gly Ser Gly
        115                 120                 125
Gly Gly Gly Ser Gly Gly Gly Gly Ser Gln Ser Val Leu Thr Gln Pro
    130                 135                 140
Pro Ser Val Ser Leu Ala Pro Gly Gln Thr Ala Lys Ile Thr Cys Gly
145                 150                 155                 160
Gly Ser Asp Ile Gly Asn Lys Asn Val His Trp Tyr Gln Gln Lys Pro
            165                 170                 175
Gly Gln Ala Pro Val Leu Val Val Tyr Asp Asp Tyr Asn Arg Pro Ser
        180                 185                 190
Gly Ile Pro Glu Arg Phe Ser Gly Ser Asn Ser Gly Asp Ser Ala Thr
    195                 200                 205
Leu Thr Ile Ser Thr Val Glu Val Gly Asp Glu Ala Asp Tyr Phe Cys
210                 215                 220
Gln Val Trp Asp Gly Ser Gly Asp Pro Tyr Trp Val Phe Gly Gly Gly
225                 230                 235                 240
Thr Gln Leu Thr Val Leu Gly
            245
```

```
<210> SEQ ID NO 9
<211> LENGTH: 741
<212> TYPE: DNA
<213> ORGANISM: Artificial Sequence
<220> FEATURE:
<223> OTHER INFORMATION: CD19-reactive ScFv5 binding domain (LTG2068)

<400> SEQUENCE: 9
gaggtccagc tggtacagtc tggagctgag gtgaagaagc ctggggcctc agtgaaggtc      60
tcctgcaagg catctggata caccttcacc ggctactata tgcactgggt gcggcaggcc     120
cctggacaag gcttgagtg gataggatta atcaacccta gtggtggtag cacaagctac      180
gaacagaagt tccagggcag agtcgccatg accaggaca cgtcaacgag cacagtctac      240
atggagctga gcagcctgag atctgaggac acggccgtgt attactgtgc gagatcggat     300
cggggaatta ccgccacgga cgcttttgat atctggggcc aagggacaat ggtcaccgtc     360
tcttcaggcg gaggaggctc cgggggagga ggttccgggg cgggggttc ccagtctgtg      420
ctgactcagc caccctcggt gtcagtggcc ccagggcaga cggccaagat tacctgtggg    480
ggaagtgaca ttggagataa aaatgtccac tggtaccagc agaagccagg ccaggcccct     540
gtcctggtcg tctatgatga ttacgaccgg ccctcaggga tccctgagcg attctctggc    600
```

```
tccaactctg gggacgcggc caccctgacg atcagcacgg tcgaagtcgg ggatgaggcc     660
gactatttct gtcaggtgtg ggacggtatt ggtgatccct attgggtgtt cggcggaggg     720
acccagctca ccgttttagg t                                               741
```

```
<210> SEQ ID NO 10
<211> LENGTH: 247
<212> TYPE: PRT
<213> ORGANISM: Artificial Sequence
<220> FEATURE:
<223> OTHER INFORMATION: CD19-reactive ScFv5 binding domain (LTG2068)

<400> SEQUENCE: 10
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Leu Ile Asn Pro Ser Gly Gly Ser Thr Ser Tyr Glu Gln Lys Phe
    50                  55                  60

Gln Gly Arg Val Ala Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Pro Ser Val Ser Val Ala Pro Gly Gln Thr Ala Lys Ile Thr Cys Gly
145                 150                 155                 160

Gly Ser Asp Ile Gly Asp Lys Asn Val His Trp Tyr Gln Gln Lys Pro
                165                 170                 175

Gly Gln Ala Pro Val Leu Val Val Tyr Asp Asp Tyr Asp Arg Pro Ser
            180                 185                 190

Gly Ile Pro Glu Arg Phe Ser Gly Ser Asn Ser Gly Asp Ala Ala Thr
        195                 200                 205

Leu Thr Ile Ser Thr Val Glu Val Gly Asp Glu Ala Asp Tyr Phe Cys
    210                 215                 220

Gln Val Trp Asp Gly Ile Gly Asp Pro Tyr Trp Val Phe Gly Gly Gly
225                 230                 235                 240

Thr Gln Leu Thr Val Leu Gly
                245

```
<210> SEQ ID NO 11
<211> LENGTH: 741
<212> TYPE: DNA
<213> ORGANISM: Artificial Sequence
<220> FEATURE:
<223> OTHER INFORMATION: CD19-reactive ScFv6 binding domain (LTG2069)

<400> SEQUENCE: 11
```

```
gaggtccagc tagtacagtc tggagctgag gtgaagaagc ctggggcctc agtgaaggtc     60
tcctgcaagg cttctggata caccttcacc agctactata tgcactgggt gcgacaggcc    120
cctggacaag ggcttgagtg gatgggaatg atcaaccecta gtggtggtag cacaagctac   180
```

```
gcacagaagt tccagggcag agtcaccatg accagggaca cgtccacgag cacagtctac      240
atggagctga gcagcctgag atctgaggac acggccgtgt attactgtgc gagatcggat      300
cggggaatta ccgccacgga cgcttttgat atctggggcc aagggacaat ggtcaccgtc      360
tcttcaggcg gaggaggctc cggggggagga ggttccgggg gcggggggttc ccagtctgtg    420
```
```
gcacagaagt tccagggcag agtcaccatg accagggaca cgtccacgag cacagtctac      240
atggagctga gcagcctgag atctgaggac acggccgtgt attactgtgc gagatcggat      300
cggggaatta ccgccacgga cgcttttgat atctggggcc aagggacaat ggtcaccgtc      360
tcttcaggcg gaggaggctc cgggggagga ggttccgggg gcggggttc ccagtctgtg       420 ctgactcagc caccctcggt gtcagtggcc ccagggcaga cggccaagat acctgtggg       480 ggaagtgaca ttggaaataa aaatgcccac tggtaccagc agaagccagg ccaggcccct      540
gtcctggtcg tctatgatga ttacgaccgg ccctcaggga tctctgagcg attctctggc      600
tccaactctg ggacgcggc caccctgacg atcagcacgg tcgaagtcgg ggatgaggcc       660
gactatttct gtcaggtgtg ggacggtagt ggtgatcctt tttgggtgtt cggcggaggg      720
acccagctca ccgttttagg t                                                741
```

<210> SEQ ID NO 12
<211> LENGTH: 247
<212> TYPE: PRT
<213> ORGANISM: Artificial Sequence
<220> FEATURE:
<223> OTHER INFORMATION: CD19-reactive ScFv6 binding domain (LTG2069)

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Met Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Thr Ala Thr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Pro Ser Val Ser Val Ala Pro Gly Gln Thr Ala Lys Ile Thr Cys Gly
145                 150                 155                 160

Gly Ser Asp Ile Gly Asn Lys Asn Ala His Trp Tyr Gln Gln Lys Pro
                165                 170                 175

Gly Gln Ala Pro Val Leu Val Val Tyr Asp Asp Tyr Asp Arg Pro Ser
            180                 185                 190

Gly Ile Ser Glu Arg Phe Ser Gly Ser Asn Ser Gly Asp Ala Ala Thr
        195                 200                 205

Leu Thr Ile Ser Thr Val Glu Val Gly Asp Glu Ala Asp Tyr Phe Cys
    210                 215                 220

Gln Val Trp Asp Gly Ser Gly Asp Pro Phe Trp Val Phe Gly Gly Gly
225                 230                 235                 240

Thr Gln Leu Thr Val Leu Gly
                245

<210> SEQ ID NO 13
<211> LENGTH: 741
<212> TYPE: DNA
<213> ORGANISM: Artificial Sequence
<220> FEATURE:
<223> OTHER INFORMATION: CD19-reactive ScFv7 binding domain (LTG2070)

<400> SEQUENCE: 13

```
gaggtccagc tggtacagtc tggagctgag gtgaagaggc ctggggcctc agtgaaggtc      60
tcctgcaagg cttctggata ccttcacc agctactata tgcactgggt gcgacaggcc      120
cctggacgag gcttgagtg gatgggatta atcaaccta gtggtggtag cacaagctac      180
gcacaggagt tccagggcag agtcaccatg accagggaca tgtccacgag cacagtctac      240
atggagctga gcagcctgag atctgaggac acggccgtgt attactgtgc gagatcggat      300
cggggaatta gcgccacgga cgcttttgat atctggggcc aagggacaat ggtcaccgtc      360
tcttcaggcg gaggaggctc cggggagga ggttccgggg gcggggggttc ccagtctgtg      420
ctgactcagc caccctcggt gtcagtggcc ccagggcaga tggccaagat acctgtggg      480
ggaagtgaca ttggaaataa aaatgtccac tggtaccagc agaagccagg ccaggcccct      540
gtcctggtcg tctatgatga ttacaaccgg ccctcaggga tccctgagcg attctctggc      600
tccaactctg ggacgcggc caccctgacg atcagcacgg tcgaagtcgg ggatgaggcc      660
gactatttct gtcaggtatg ggacggtagt ggtgatcctt attgggtgtt cggcggaggg      720
acccagctca ccgatttagg t                                               741
```

<210> SEQ ID NO 14
<211> LENGTH: 247
<212> TYPE: PRT
<213> ORGANISM: Artificial Sequence
<220> FEATURE:
<223> OTHER INFORMATION: CD19-reactive ScFv7 binding domain (LTG2070)

<400> SEQUENCE: 14

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Arg Gly Leu Glu Trp Met
        35                  40                  45

Gly Leu Ile Asn Pro Ser Gly Gly Ser Thr Ser Tyr Ala Gln Glu Phe
    50                  55                  60

Gln Gly Arg Val Thr Met Thr Arg Asp Met Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Ile Ser Ala Thr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Pro Ser Val Ser Val Ala Pro Gly Gln Met Ala Lys Ile Thr Cys Gly
145                 150                 155                 160

Gly Ser Asp Ile Gly Asn Lys Asn Val His Trp Tyr Gln Gln Lys Pro
                165                 170                 175
```

Gly Gln Ala Pro Val Leu Val Val Tyr Asp Asp Tyr Asn Arg Pro Ser
                180                 185                 190

Gly Ile Pro Glu Arg Phe Ser Gly Ser Asn Ser Gly Asp Ala Ala Thr
            195                 200                 205

Leu Thr Ile Ser Thr Val Glu Val Gly Asp Glu Ala Asp Tyr Phe Cys
        210                 215                 220

Gln Val Trp Asp Gly Ser Gly Asp Pro Tyr Trp Val Phe Gly Gly Gly
225                 230                 235                 240

Thr Gln Leu Thr Asp Leu Gly
                245

<210> SEQ ID NO 15
<211> LENGTH: 741
<212> TYPE: DNA
<213> ORGANISM: Artificial Sequence
<220> FEATURE:
<223> OTHER INFORMATION: CD19-reactive ScFv8 binding domain (LTG2071)

<400> SEQUENCE: 15
gaggtccagc tggtacagtc tggagctgag gtgaagaggc tggggcctc agtgaaggtc      60 tcctgcaagg cttctggata caccttcacc agctactata tgcactgggt gcgacaggcc    120
cctggacaag gcttgtgtg atgggattaa tcaaccta gtggtggcag cacaagctac        180
gcacagaagt tccagggcag agtcaccatg accaggggaca cgtccacgag cacagtctac   240
atggagctga gcagcctgag atctgaggac acggccgtgt attactgtgc gagatcggat    300
cggggaatta ccgccacgga cgcttttgat atctggggcc aagggacaat ggtcaccgtc    360
tcttcaggcg gaggaggctc cggggagga ggttccgggg gcggggttc ccagtctgtg      420 ctgactcagc caccctcggt ctcagtggcc cagggcaga cggccaagac tacctgtggg     480
ggaagtgaca ttggaaataa aaatgtccac tggtaccagc agaagccagg ccaggcccct    540
gtcctggtcg tctatgatga ttacgaccgg ccctcaggga tccctgagcg attctctggc    600
tccaactctg ggacgcggc caccctgacg atcagcacgg tcgaagtcgg ggatgaggcc     660
gactatgtct gtcaggtgtg ggacggtagt ggtgatcctt attgggtgtt cggcggaggg    720
acccagctca ccgttttagg t                                              741

<210> SEQ ID NO 16
<211> LENGTH: 247
<212> TYPE: PRT
<213> ORGANISM: Artificial Sequence
<220> FEATURE:
<223> OTHER INFORMATION: CD19-reactive ScFv8 binding domain (LTG2071)

<400> SEQUENCE: 16

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Val Trp Met
        35                  40                  45

Gly Leu Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Ala Arg Ser Asp Arg Gly Ile Thr Ala Thr Asp Ala Phe Asp Ile Trp
            100                 105                 110
Gly Gln Gly Thr Met Val Thr Val Ser Ser Gly Gly Gly Ser Gly
        115                 120                 125
Gly Gly Gly Ser Gly Gly Gly Ser Gln Ser Val Leu Thr Gln Pro
    130                 135                 140
Pro Ser Val Ser Val Ala Pro Gly Gln Thr Ala Lys Thr Thr Cys Gly
145                 150                 155                 160
Gly Ser Asp Ile Gly Asn Lys Asn Val His Trp Tyr Gln Gln Lys Pro
                165                 170                 175
Gly Gln Ala Pro Val Leu Val Val Tyr Asp Asp Tyr Asp Arg Pro Ser
            180                 185                 190
Gly Ile Pro Glu Arg Phe Ser Gly Ser Asn Ser Gly Asp Ala Ala Thr
        195                 200                 205
Leu Thr Ile Ser Thr Val Glu Val Gly Asp Glu Ala Asp Tyr Val Cys
    210                 215                 220
Gln Val Trp Asp Gly Ser Gly Asp Pro Tyr Trp Val Phe Gly Gly Gly
225                 230                 235                 240
Thr Gln Leu Thr Val Leu Gly
                245
```

<210> SEQ ID NO 17
<211> LENGTH: 66
<212> TYPE: DNA
<213> ORGANISM: Artificial Sequence
<220> FEATURE:
<223> OTHER INFORMATION: leader/signal peptide sequence (LP)

<400> SEQUENCE: 17

```
atgctgctgc tggtgaccag cctgctgctg tgcgaactgc cgcatccggc gtttctgctg      60
attccg                                                                66
```

<210> SEQ ID NO 18
<211> LENGTH: 22
<212> TYPE: PRT
<213> ORGANISM: Artificial Sequence
<220> FEATURE:
<223> OTHER INFORMATION: leader/signal peptide sequence (LP)

<400> SEQUENCE: 18

```
Met Leu Leu Leu Val Thr Ser Leu Leu Leu Cys Glu Leu Pro His Pro
1               5                   10                  15
Ala Phe Leu Leu Ile Pro
            20
```

<210> SEQ ID NO 19
<211> LENGTH: 1485
<212> TYPE: DNA
<213> ORGANISM: Artificial Sequence
<220> FEATURE:
<223> OTHER INFORMATION: LTG2050_(LP-M19217-CD8 TM-41BB-CD3 zeta)

<400> SEQUENCE: 19

```
atgcttctcc tggtcacctc cctgctcctc tgcgaactgc ctcacccgc cttccttctg      60 attcctgagg tccagctggt acagtctgga gctgaggtga agaagcctgg ggcctcagtg    120
aaggtctcct gcaaggcttc tggatacacc ttcaccagct actatatgca ctgggtgcga    180
caggcccctg gacaagggct tgagtggatg gaataatca accctagtgg tggtagcaca     240
agctacgcac agaagttcca gggcagagtc accatgacca gggacacgtc cacgagcaca    300
```

```
gtctacatgg agctgagcag cctgagatct gaggacacgg ccgtgtatta ctgtgcgaga      360
tcggatcggg gaattaccgc cacggacgct tttgatatct ggggccaagg gacaatggtc      420
accgtctctt caggaggtgg cgggtctggt ggaggcggta gcggtggtgg cggatcccag      480
tctgtgctga ctcagccacc ctcggtgtca gtggccccag gcagacggc caagattacc       540 tgtgggggaa gtgacattgg aaataaaaat gtccactggt accagcagaa gccaggccag      600
gcccctgtcc tggtcgtcta tgatgattac gaccggccct cagggatccc tgagcgattc      660
tctggctcca actctgggga cgcggccacc ctgacgatca gcacggtcga agtcggggat      720
gaggccgact atttctgtca ggtgtgggac agtagtggtg atccttattg ggtgttcggc      780
ggagggaccc agctcaccgt tttaggtgcg ccgcaacta ccaccctgc ccctcggccg        840 ccgactccgg ccccaaccat cgcaagccaa cccctctcct tgcgcccga agcttgccgc      900 ccggccgcgg gtggagccgt gcatacccgg gggctggact ttgcctgcga tatctacatt     960
tgggccccgc tggccggcac ttgcggcgtg ctcctgctgt cgctggtcat caccctttac    1020
tgcaagaggg gccggaagaa gctgctttac atcttcaagc agccgttcat gcggcccgtg    1080
cagacgactc aggaagagga cggatgctcg tgcagattcc ctgaggagga agagggggga    1140
tgcgaactgc gcgtcaagtt ctcacggtcc gccgacgccc ccgcatatca acagggccag    1200
aatcagctct acaacgagct gaacctggga aggagagagg agtacgacgt gctggacaag    1260
cgacgcggac gcgacccgga gatggggggg aaaccacggc ggaaaaaccc tcaggaagga    1320
ctgtacaacg aactccagaa agacaagatg gcggaagcct actcagaaat cgggatgaag    1380
ggagagcgga ggaggggaaa gggtcacgac gggctgtacc agggactgag caccgccact    1440
aaggatacct acgatgcctt gcatatgcaa gcactcccac cccgg                    1485
```

<210> SEQ ID NO 20
<211> LENGTH: 495
<212> TYPE: PRT
<213> ORGANISM: Artificial Sequence
<220> FEATURE:
<223> OTHER INFORMATION: LTG2050_(LP-M19217-CD8 TM-41BB-CD3zeta)

<400> SEQUENCE: 20

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Ser Tyr Tyr Met His Trp Val Arg Gln Ala Pro Gly
        50                  55                  60

Gln Gly Leu Glu Trp Met Gly Ile Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Gln
```

```
              145                 150                 155                 160
        Ser Val Leu Thr Gln Pro Pro Ser Val Ser Val Ala Pro Gly Gln Thr
                        165                 170                 175

Ala Lys Ile Thr Cys Gly Gly Ser Asp Ile Gly Asn Lys Asn Val His
                        180                 185                 190

Trp Tyr Gln Gln Lys Pro Gly Gln Ala Pro Val Leu Val Val Tyr Asp
                        195                 200                 205

Asp Tyr Asp Arg Pro Ser Gly Ile Pro Glu Arg Phe Ser Gly Ser Asn
                        210                 215                 220

Ser Gly Asp Ala Ala Thr Leu Thr Ile Ser Thr Val Glu Val Gly Asp
        225                 230                 235                 240

Glu Ala Asp Tyr Phe Cys Gln Val Trp Asp Ser Ser Gly Asp Pro Tyr
                        245                 250                 255

Trp Val Phe Gly Gly Gly Thr Gln Leu Thr Val Leu Gly Ala Ala Ala
                        260                 265                 270

Thr Thr Thr Pro Ala Pro Arg Pro Pro Thr Pro Ala Pro Thr Ile Ala
                        275                 280                 285

Ser Gln Pro Leu Ser Leu Arg Pro Glu Ala Cys Arg Pro Ala Ala Gly
                        290                 295                 300

Gly Ala Val His Thr Arg Gly Leu Asp Phe Ala Cys Asp Ile Tyr Ile
        305                 310                 315                 320

Trp Ala Pro Leu Ala Gly Thr Cys Gly Val Leu Leu Leu Ser Leu Val
                        325                 330                 335

Ile Thr Leu Tyr Cys Lys Arg Gly Arg Lys Lys Leu Leu Tyr Ile Phe
                        340                 345                 350

Lys Gln Pro Phe Met Arg Pro Val Gln Thr Thr Gln Glu Glu Asp Gly
                        355                 360                 365

Cys Ser Cys Arg Phe Pro Glu Glu Glu Glu Gly Gly Cys Glu Leu Arg
                        370                 375                 380

Val Lys Phe Ser Arg Ser Ala Asp Ala Pro Ala Tyr Gln Gln Gly Gln
        385                 390                 395                 400

Asn Gln Leu Tyr Asn Glu Leu Asn Leu Gly Arg Arg Glu Glu Tyr Asp
                        405                 410                 415

Val Leu Asp Lys Arg Arg Gly Arg Asp Pro Glu Met Gly Gly Lys Pro
                        420                 425                 430

Arg Arg Lys Asn Pro Gln Glu Gly Leu Tyr Asn Glu Leu Gln Lys Asp
                        435                 440                 445

Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
        465                 470                 475                 480

Lys Asp Thr Tyr Asp Ala Leu His Met Gln Ala Leu Pro Pro Arg
                        485                 490                 495

<210> SEQ ID NO 21
<211> LENGTH: 1485
<212> TYPE: DNA
<213> ORGANISM: Artificial Sequence
<220> FEATURE:
<223> OTHER INFORMATION: LTG2065 (LP-M19217-1-CD8 TM-41BB-CD3 zeta)

<400> SEQUENCE: 21
atgctgctgc tggtgaccag cctgctgctg tgcgaactgc cgcatccggc gtttctgctg       60
attccggagg tccagctggt acagtctgga gctgaggtga agaagcctgg ggcctcagtg      120
```

```
aaggtctcct gcaaggcttc tggatacacc ttcaccagct actatatgca ctgggtgcga    180
caggcccctg gacaagggct tgagtggatg ggattaatca accctagtgg tggtagcaca    240
agctacgcac agaagttcca gggcagagtc accatgacca gggacacgtc cacgagcaca    300
gtctacatgg agctgagcag cctgagatct gaggacacgg ccgtgtatta ctgtgcgaga    360
tcggatcggg gaattaccgc cacggacgct tttgatatct ggggccaagg gacaatggtc    420
accgtctctt caggcggagg aggctccggg ggaggaggtt ccgggggcgg gggttcccag    480
tctgtgctga ctcagccacc ctcggtgtca gtggccccag gcggatggc caagattacc      540 tgtgggggaa gtgacattgg aaataaaaat gtccactggt atcagcagaa gccaggccag    600
gcccctgtcc tggttgtcta tgatgattac gaccggccct cagggatccc tgagcgattc    660
tctggctcca actctgggga cgcggccacc ctgacgatca gcacggtcga agtcggggat    720
gaggccgact atttctgtca ggtgtgggac ggtagtggtg atccttattg gatgttcggc    780
ggagggaccc agctcaccgt tttaggtgcg gccgcaacta ccaccccctgc ccctcggccg    840 ccgactccgg ccccaaccat cgcaagccaa ccccctctcct tgcgccccga agcttgccgc    900
ccggccgcgg gtggagccgt gcatacccgg gggctggact ttgcctgcga tatctacatt    960 tgggcccgc tggccggcac ttgcggcgtg ctcctgctgt cgctggtcat cacccttac    1020 tgcaagaggg gccggaagaa gctgctttac atcttcaagc agccgttcat gcggcccgtg    1080
cagacgactc aggaagagga cggatgctcg tgcagattcc ctgaggagga agaggggga    1140 tgcgaactgc gcgtcaagtt ctcacggtcc gccgacgccc ccgcatatca acagggccag    1200
aatcagctct acaacgagct gaacctggga aggagagagg agtacgacgt gctggacaag    1260
cgacgcggac gcgacccgga gatggggggg aaaccacggc ggaaaaaccc tcaggaagga    1320
ctgtacaacg aactccagaa agacaagatg gcggaagcct actcagaaat cgggatgaag    1380
ggagagcgga ggaggggaaa gggtcacgac gggctgtacc agggactgag caccgccact    1440
aaggatacct acgatgcctt gcatatgcaa gcactcccac cccgg                    1485
```

<210> SEQ ID NO 22
<211> LENGTH: 495
<212> TYPE: PRT
<213> ORGANISM: Artificial Sequence
<220> FEATURE:
<223> OTHER INFORMATION: LTG2065_(LP-M19217-1-CD8 TM-41BB-CD3 zeta)

<400> SEQUENCE: 22

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Ser Tyr Tyr Met His Trp Val Arg Gln Ala Pro Gly
        50                  55                  60

Gln Gly Leu Glu Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125
```

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Ser Gln
145                 150                 155                 160

Ser Val Leu Thr Gln Pro Pro Ser Val Ser Val Ala Pro Gly Arg Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Met Phe Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 23
<211> LENGTH: 1485
<212> TYPE: DNA
<213> ORGANISM: Artificial Sequence
<220> FEATURE:
<223> OTHER INFORMATION: LTG2066 _(LP-M19217-2-CD8 TM-41BB-CD3 zeta)

<400> SEQUENCE: 23

```
atgctgctgc tggtgaccag cctgctgctg tgcgaactgc cgcatccggc gtttctgctg    60
attccggagg tccagctggt acagtctgga gctgaggtga agaagcctgg ggcctcagtg   120
aaggtctcct gcaaggcttc cggatacacc ttcaccagct actacatgca ctgggtgcga   180
caggcccctg gacaagggtt tgagtggatg ggattaatca ccctagtgg tagtagcaca   240
agctacgcac agaagttcca gggcagagtc accatgacca gggacacgtc cacgagcaca   300
gtctacatgg agctgagcaa cctgagatct gaggacacgg ccgtgtatta ctgtgcgaga   360
tcggatcggg gaattaccgc cacggacgct tttgatatct ggggccaagg acaatggtc    420
accgtctctt caggcggagg aggctccggg ggaggaggtt ccggggggcgg gggttcccag   480
tctgtgctga ctcagccacc ctcggtgcca gtggccccag gcagacggc caagattatc    540
tgtgggggaa gtgacattgg aaataaaaat gtccactggt accagcagaa gccaggccag   600
gcccctgtcc tggtcgtcta tgatgactac gaccggccct cagggatccc tgagcgattc   660
tctggctcca actctgggga cgcggccacc ctgacgatca gcacggttga agtcggggat   720
gaggccgact atttctgtca ggtgtgggac ggtagtggtg atccttattg ggtgttcggc   780
ggagggaccc agctcaccgt cttaggtgcg ccgcaacta ccaccctgc ccctcggccg    840
ccgactccgg ccccaaccat cgcaagccaa cccctctcct gcgccccga gcttgccgc    900
ccggccgcgg gtggagccgt gcatacccgg gggctggact ttgcctgcga tatctacatt   960
tgggcccccgc tggccggcac ttgcggcgtg ctcctgctgt cgctggtcat caccctttac  1020
tgcaagaggg gccggaagaa gctgctttac atcttcaagc agccgttcat gcggcccgtg  1080
cagacgactc aggaagagga cggatgctcg tgcagattcc ctgaggagga gagggggga   1140
tgcgaactgc gcgtcaagtt ctcacggtcc gccgacgccc ccgcatatca acagggccag  1200
aatcagctct acaacgagct gaacctggga aggagagagg agtacgacgt gctggacaag  1260
cgacgcggac gcgaccccga gatggggggg aaaccacggc ggaaaaaccc tcaggaagga  1320
ctgtacaacg aactccagaa agacaagatg gcggaagcct actcagaaat cgggatgaag  1380
ggagagcgga ggaggggaaa gggtcacgac gggctgtacc agggactgag caccgccact  1440
aaggatacct acgatgcctt gcatatgcaa gcactcccac cccgg                  1485
```

<210> SEQ ID NO 24
<211> LENGTH: 495
<212> TYPE: PRT
<213> ORGANISM: Artificial Sequence
<220> FEATURE:
<223> OTHER INFORMATION: LTG2066 _(LP-M19217-2-CD8 TM-41BB-CD3 zeta)

<400> SEQUENCE: 24

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Phe Glu Trp Met Gly Leu Ile Asn Pro Ser Gly Ser Ser Thr
65                  70                  75                  80

Ser Tyr Ala Gln Lys Phe Gln Gly Arg Val Thr Met Thr Arg Asp Thr
                85                  90                  95
```

```
Ser Thr Ser Thr Val Tyr Met Glu Leu Ser Asn Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Pro Val Ala Pro Gly Gln Thr
                165                 170                 175

Ala Lys Ile Ile Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Val Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 25
<211> LENGTH: 1485
<212> TYPE: DNA
```

<213> ORGANISM: Artificial Sequence
<220> FEATURE:
<223> OTHER INFORMATION: LTG2067_(LP-M19217-7-CD8 TM-41BB-CD3 zeta)

<400> SEQUENCE: 25

```
atgctgctgc tggtgaccag cctgctgctg tgcgaactgc cgcatccggc gtttctgctg      60
attccggagg tccagctggt acagtctgga gctgaggtga acaagcctgg tgcctcagtg     120
aaggtctcct gcaaggcttc tggatacacc ttcaccagct actatatgca ctgggtgcga     180
caggcccctg gacaagggct tgagtggatg gaatgatca accctagtgg tggtagcaca     240
agctacgcac agaagttcca gggcagagtc accatgacca gggacacgtc cacgagcaca     300
gtctacatgg agctgagcag cctgagatct gaggacacgg ccgtgtatta ctgtgcgaga     360
tcggatcggg gaattacctc cacggacgct tttgatatct ggggccaagg gacaatggtc     420
accgtctctt caggcggagg aggctccggg ggaggaggtt ccggggggcgg gggttcccag     480
tctgtgctga ctcagccacc ctcggtgtca ttggccccag gcagacggc caagattacc     540
tgtgggggaa gtgacattgg aaataaaaat gtccactggt accagcagaa gccaggccag     600
gccctgtcc tagtcgtcta tgatgattac aaccggccct cagggatccc tgagcgattc     660
tctggctcca actctgggga ctcagccacc ctgacgatca gcgggtcga agtcggggat     720
gaggccgact atttctgtca ggtgtgggac ggtagtggtg atccttattg ggtgttcggc     780
ggagggaccc agctcaccgt tttaggtgcg gccgcaacta ccaccctgc ccctcggccg     840
ccgactccgg ccccaaccat cgcaagccaa cccctctcct tgcgccccga agcttgccgc     900
ccggccgcgg tggagccgt gcatacccgg ggctggact tgcctgcga tatctacatt     960
tgggccccgc tggccggcac ttgcggcgtg ctcctgctgt cgctggtcat caccctttac    1020
tgcaagaggg gccggaagaa gctgctttac atcttcaagc agccgttcat gcggcccgtg    1080
cagacgactc aggaagagga cggatgctcg tgcagattcc ctgaggagga agaggggga    1140
tgcgaactgc gcgtcaagtt ctcacggtcc gccgacgccc ccgcatatca acagggccag    1200
aatcagctct acaacgagct gaacctggga aggagagagg agtacgacgt gctggacaag    1260
cgacgcggac gcgaccccga gatggggggg aaaccacggc ggaaaaaccc tcaggaagga    1320
ctgtacaacg aactccagaa agacaagatg gcggaagcct actcagaaat cgggatgaag    1380
ggagagcgga ggagggggaaa gggtcacgac gggctgtacc agggactgag caccgccact    1440
aaggatacct acgatgcctt gcatatgcaa gcactcccac cccgg                    1485
```

<210> SEQ ID NO 26
<211> LENGTH: 495
<212> TYPE: PRT
<213> ORGANISM: Artificial Sequence
<220> FEATURE:
<223> OTHER INFORMATION: LTG2067 _(LP-M19217-7-CD8 TM-41BB-CD3 zeta)

<400> SEQUENCE: 26

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Asn Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Met Ile Asn Pro Ser Gly Gly Ser Thr
```

-continued

```
                65                  70                  75                  80
Ser Tyr Ala Gln Lys Phe Gln Gly Arg Val Thr Met Thr Arg Asp Thr
                    85                  90                  95

Ser Thr Ser Thr Val Tyr Met Glu Leu Ser Ser Leu Arg Ser Glu Asp
                    100                 105                 110

Thr Ala Val Tyr Tyr Cys Ala Arg Ser Asp Arg Gly Ile Thr Ser Thr
                    115                 120                 125

Asp Ala Phe Asp Ile Trp Gly Gln Gly Thr Met Val Thr Val Ser Ser
                    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Leu Ala Pro Gly Gln Thr
                    165                 170                 175

Ala Lys Ile Thr Cys Gly Gly Ser Asp Ile Gly Asn Lys Asn Val His
                    180                 185                 190

Trp Tyr Gln Gln Lys Pro Gly Gln Ala Pro Val Leu Val Val Tyr Asp
                    195                 200                 205

Asp Tyr Asn Arg Pro Ser Gly Ile Pro Glu Arg Phe Ser Gly Ser Asn
                    210                 215                 220

Ser Gly Asp Ser Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                    245                 250                 255

Trp Val Phe Gly Gly Gly Thr Gln Leu Thr Val Leu Gly Ala Ala Ala
                    260                 265                 270

Thr Thr Thr Pro Ala Pro Arg Pro Pro Thr Pro Ala Pro Thr Ile Ala
                    275                 280                 285

Ser Gln Pro Leu Ser Leu Arg Pro Glu Ala Cys Arg Pro Ala Ala Gly
                    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                    325                 330                 335

Ile Thr Leu Tyr Cys Lys Arg Gly Arg Lys Lys Leu Leu Tyr Ile Phe
                    340                 345                 350

Lys Gln Pro Phe Met Arg Pro Val Gln Thr Thr Gln Glu Glu Asp Gly
                    355                 360                 365

Cys Ser Cys Arg Phe Pro Glu Glu Glu Glu Gly Gly Cys Glu Leu Arg
                    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                    405                 410                 415

Val Leu Asp Lys Arg Arg Gly Arg Asp Pro Glu Met Gly Gly Lys Pro
                    420                 425                 430

Arg Arg Lys Asn Pro Gln Glu Gly Leu Tyr Asn Glu Leu Gln Lys Asp
                    435                 440                 445

Lys Met Ala Glu Ala Tyr Ser Glu Ile Gly Met Lys Gly Glu Arg Arg
                    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                    485                 490                 495
```

<210> SEQ ID NO 27
<211> LENGTH: 1485
<212> TYPE: DNA
<213> ORGANISM: Artificial Sequence
<220> FEATURE:
<223> OTHER INFORMATION: LTG2068_(LP-M19217-23-CD8 TM-41BB-CD3 zeta)

<400> SEQUENCE: 27

```
atgctgctgc tggtgaccag cctgctgctg tgcgaactgc cgcatccggc gtttctgctg      60
attccggagg tccagctggt acagtctgga gctgaggtga agaagcctgg ggcctcagtg     120
aaggtctcct gcaaggcatc tggatacacc ttcaccggct actatatgca ctgggtgcgg     180
caggcccctg gacaagggct tgagtggata ggattaatca accctagtgg tggtagcaca     240
agctacgaac agaagttcca gggcagagtc gccatgacca gggacacgtc aacgagcaca     300
gtctacatgg agctgagcag cctgagatct gaggacacgg ccgtgtatta ctgtgcgaga     360
tcggatcggg gaattaccgc cacggacgct tttgatatct ggggccaagg gacaatggtc     420
accgtctctt caggcggagg aggctccggg ggaggaggtt ccggggggcgg gggttcccag     480
tctgtgctga ctcagccacc ctcggtgtca gtggccccag gcagacggc caagattacc     540
tgtgggggaa gtgacattgg agataaaaat gtccactggt accagcagaa gccaggccag     600
gcccctgtcc tggtcgtcta tgatgattac accggccct cagggatccc tgagcgattc     660
tctggctcca actctgggga cgcggccacc ctgacgatca gcacggtcga agtcggggat     720
gaggccgact atttctgtca ggtgtgggac ggtattggtg atccctattg ggtgttcggc     780
ggagggaccc agctcaccgt tttaggtgcg ccgcaacta ccacccctgc ccctcggccg     840
ccgactccgg ccccaaccat cgcaagccaa cccctctcct gcgccccga gcttgccgc     900
ccggccgcgg gtggagccgt gcatacccgg gggctggact ttgcctgcga tatctacatt     960
tgggccccgc tggccggcac ttgcggcgtg ctcctgctgt cgctggtcat cacccttttac    1020
tgcaagaggg gccggaagaa gctgctttac atcttcaagc agccgttcat gcggcccgtg    1080
cagacgactc aggaagagga cggatgctcg tgcagattcc ctgaggagga gaggggggga    1140
tgcgaactgc gcgtcaagtt ctcacggtcc gccgacgccc ccgcatatca acagggccag    1200
aatcagctct acaacgagct gaacctggga aggagagagg agtacgacgt gctggacaag    1260
cgacgcggac gcgaccccga gatggggggg aaaccacggc ggaaaaaccc tcaggaagga    1320
ctgtacaacg aactccagaa agacaagatg gcggaagcct actcagaaat cgggatgaag    1380
ggagagcgga ggagggaaa gggtcacgac gggctgtacc agggactgag caccgccact    1440
aaggatacct acgatgcctt gcatatgcaa gcactcccac cccgg                      1485
```

<210> SEQ ID NO 28
<211> LENGTH: 495
<212> TYPE: PRT
<213> ORGANISM: Artificial Sequence
<220> FEATURE:
<223> OTHER INFORMATION: LTG2068 _(LP-M19217-23-CD8 TM-41BB-CD3 zeta)

<400> SEQUENCE: 28

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
                20                  25                  30

Val Lys Lys Pro Gly Ala Ser Val Lys Val Ser Cys Lys Ala Ser Gly
        35                  40                  45

```
Tyr Thr Phe Thr Gly Tyr Tyr Met His Trp Val Arg Gln Ala Pro Gly
         50                  55                  60

Gln Gly Leu Glu Trp Ile Gly Leu Ile Asn Pro Ser Gly Gly Ser Thr
 65              70                  75                  80

Ser Tyr Glu Gln Lys Phe Gln Gly Arg Val Ala Met Thr Arg Asp Thr
                 85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
            115                 120                 125

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Gly Ser Gln
145                 150                 155                 160

Ser Val Leu Thr Gln Pro Ser Val Ser Val Ala Pro Gly Gln Thr
                165                 170                 175

Ala Lys Ile Thr Cys Gly Gly Ser Asp Ile Gly Asp Lys Asn Val His
                180                 185                 190

Trp Tyr Gln Gln Lys Pro Gly Gln Ala Pro Val Leu Val Val Tyr Asp
                195                 200                 205

Asp Tyr Asp Arg Pro Ser Gly Ile Pro Glu Arg Phe Ser Gly Ser Asn
210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ile Gly Asp Pro Tyr
                245                 250                 255

Trp Val Phe Gly Gly Gly Thr Gln Leu Thr Val Leu Gly Ala Ala Ala
                260                 265                 270

Thr Thr Thr Pro Ala Pro Arg Pro Pro Thr Pro Ala Pro Thr Ile Ala
            275                 280                 285

Ser Gln Pro Leu Ser Leu Arg Pro Glu Ala Cys Arg Pro Ala Ala Gly
            290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
            370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460
```

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
            485                 490                 495

<210> SEQ ID NO 29
<211> LENGTH: 1485
<212> TYPE: DNA
<213> ORGANISM: Artificial Sequence
<220> FEATURE:
<223> OTHER INFORMATION: LTG2069_(LP-M19217-29-CD8 TM-41BB-CD3 zeta)

<400> SEQUENCE: 29

```
atgctgctgc tggtgaccag cctgctgctg tgcgaactgc cgcatccggc gtttctgctg      60
attccggagg tccagctagt acagtctgga gctgaggtga agaagcctgg ggcctcagtg     120
aaggtctcct gcaaggcttc tggatacacc ttcaccagct actatatgca ctgggtgcga     180
caggcccctg gacaagggct tgagtggatg ggaatgatca accctagtgg tggtagcaca     240
agctacgcac agaagttcca gggcagagtc accatgacca gggacacgtc cacgagcaca     300
gtctacatgg agctgagcag cctgagatct gaggacacgg ccgtgtatta ctgtgcgaga     360
tcggatcggg gaattaccgc cacggacgct tttgatatct ggggccaagg acaatggtc      420
accgtctctt caggcggagg aggctccggg ggaggaggtt ccggggcgg gggttcccag      480
tctgtgctga ctcagccacc ctcggtgtca gtggccccag gcagacggc caagattacc      540
tgtgggggaa gtgacattgg aaataaaaat gcccactggt accagcagaa gccaggccag     600
gcccctgtcc tggtcgtcta tgatgattac accggccct cagggatctc tgagcgattc      660
tctggctcca actctgggga cgcggccacc ctgacgatca gcacggtcga agtcggggat     720
gaggccgact atttctgtca ggtgtgggac ggtagtggtg atccttttg ggtgttcggc      780
ggagggaccc agctcaccgt tttaggtgcg gccgcaacta ccaccctgc ccctcggccg      840
ccgactccgg ccccaaccat cgcaagccaa cccctctcct gcgcccga agcttgccgc      900
ccggccgcgg gtggagccgt gcatacccgg ggctggact ttgcctgcga tatctacatt      960
tgggcccgc tggccggcac ttgcggcgtg ctcctgctgt cgctggtcat cacccttac     1020
tgcaagaggg gccggaagaa gctgctttac atcttcaagc agccgttcat gcggcccgtg    1080
cagacgactc aggaagagga cggatgctcg tgcagattcc ctgaggagga gaggggggga    1140
tgcgaactgc gcgtcaagtt ctcacggtcc gccgacgccc cgcatatca cagggccag     1200
aatcagctct acaacgagct gaacctggga aggagagagg agtacgacgt gctggacaag    1260
cgacgcggac gcgacccgga gatggggggg aaaccacggc ggaaaaaccc tcaggaagga    1320
ctgtacaacg aactccagaa agacaagatg gcggaagcct actcagaaat cgggatgaag    1380
ggagagcgga ggagggggaaa gggtcacgac gggctgtacc agggactgag caccgccact    1440
aaggatacct acgatgcctt gcatatgcaa gcactccac cccgg                     1485
```

<210> SEQ ID NO 30
<211> LENGTH: 495
<212> TYPE: PRT
<213> ORGANISM: Artificial Sequence
<220> FEATURE:
<223> OTHER INFORMATION: LTG2069 _(LP-M19217-29-CD8 TM-41BB-CD3 zeta)

<400> SEQUENCE: 30

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
50                  55                  60

Gln Gly Leu Glu Trp Met Gly Met Ile Asn Pro Ser Gly Gly Ser Thr
65              70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Gln Thr
            165                 170                 175

Ala Lys Ile Thr Cys Gly Gly Ser Asp Ile Gly Asn Lys Asn Ala His
        180                 185                 190

Trp Tyr Gln Gln Lys Pro Gly Gln Ala Pro Val Leu Val Val Tyr Asp
    195                 200                 205

Asp Tyr Asp Arg Pro Ser Gly Ile Ser Glu Arg Phe Ser Gly Ser Asn
210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Phe
                245                 250                 255

Trp Val Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp

```
                435                 440                 445
Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 31
<211> LENGTH: 1485
<212> TYPE: DNA
<213> ORGANISM: Artificial Sequence
<220> FEATURE:
<223> OTHER INFORMATION: LTG2070_(LP-M19217-38-CD8 TM-41BB-CD3 zeta)

<400> SEQUENCE: 31
atgctgctgc tggtgaccag cctgctgctg tgcgaactgc cgcatccggc gtttctgctg      60 attccgagg tccagctggt acagtctgga gctgaggtga agaggcctgg ggcctcagtg      120
aaggtctcct gcaaggcttc tggatacacc ttcaccagct actatatgca ctgggtgcga     180
caggcccctg gacagggct tgagtggatg ggattaatca accctagtgg tggtagcaca      240
agctacgcac aggagttcca gggcagagtc accatgacca gggacatgtc cacgagcaca     300
gtctacatgg agctgagcag cctgagatct gaggacacgg ccgtgtatta ctgtgcgaga     360
tcggatcggg gaattagcgc cacggacgct tttgatatct ggggccaagg gacaatggtc     420
accgtctctt caggcggagg aggctccggg ggaggaggtt ccggggggcgg gggttcccag     480 tctgtgctga ctcagccacc ctcggtgtca gtggccccag gcagatggc caagattacc     540 tgtggggaa gtgacattgg aaataaaaat gtccactggt accagcagaa gccaggccag     600
gcccctgtcc tggtcgtcta tgatgattac aaccggccct cagggatccc tgagcgattc     660
tctggctcca actctgggga cgcggccacc ctgacgatca gcacggtcga agtcggggat     720
gaggccgact atttctgtca ggtatgggac ggtagtggtg atccttattg ggtgttcggc     780
ggagggaccc agctcaccga tttaggtgcg gccgcaacta ccaccctctgc ccctcggccg     840 ccgactccgg ccccaaccat cgcaagccaa cccctctcct tgcgcccga agcttgccgc     900 ccggccgcgg gtggagccgt gcatacccgg gggctggact ttgcctgcga tatctacatt     960
tgggccccgc tggccggcac ttgcggcgtg ctcctgctgt cgctggtcat caccctttac    1020
tgcaagaggg gccggaagaa gctgctttac atcttcaagc agccgttcat gcggcccgtg    1080
cagacgactc aggaagagga cggatgctcg tgcagattcc ctgaggagga gagggggga    1140 tgcgaactgc gcgtcaagtt ctcacggtcc gccgacgccc ccgcatatca cagggccag     1200 aatcagctct acaacgagct gaacctggga aggagagagg agtacgacgt gctggacaag     1260
cgacgcggac gcgacccgga gatggggggg aaaccacggc ggaaaaaccc tcaggaagga    1320
ctgtacaacg aactccagaa agacaagatg gcggaagcct actcagaaat cgggatgaag    1380
ggagagcgga ggagggggaaa gggtcacgac gggctgtacc agggactgag caccgccact    1440
aaggatacct acgatgcctt gcatatgcaa gcactcccac cccgg                    1485

<210> SEQ ID NO 32
<211> LENGTH: 495
<212> TYPE: PRT
<213> ORGANISM: Artificial Sequence
<220> FEATURE:
<223> OTHER INFORMATION: LTG2070 _(LP-M19217-38-CD8 TM-41BB-CD3 zeta)
```

```
<400> SEQUENCE: 32

Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Arg Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Arg Gly Leu Glu Trp Met Gly Leu Ile Asn Pro Ser Gly Gly Ser Thr
65              70                  75                  80

Ser Tyr Ala Gln Glu Phe Gln Gly Arg Val Thr Met Thr Arg Asp Met
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Ser Ala Thr
        115                 120                 125

Asp Ala Phe Asp Ile Trp Gly Gln Gly Thr Met Val Thr Val Ser Ser
130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Gln Met
                165                 170                 175

Ala Lys Ile Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asn Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Phe Cys Gln Val Trp Asp Gly Ser Gly Asp Pro Tyr
                245                 250                 255

Trp Val Phe Gly Gly Gly Thr Gln Leu Thr Asp Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415
```

```
Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 33
<211> LENGTH: 1485
<212> TYPE: DNA
<213> ORGANISM: Artificial Sequence
<220> FEATURE:
<223> OTHER INFORMATION: LTG2071_(LP-M19217-40-CD8 TM-41BB-CD3 zeta)

<400> SEQUENCE: 33
atgctgctgc tggtgaccag cctgctgctg tgcgaactgc cgcatccggc gtttctgctg      60
attccggagg tccagctggt acagtctgga gctgaggtga agaggcctgg ggcctcagtg     120
aaggtctcct gcaaggcttc tggatacacc ttcaccagct actatatgca ctgggtgcga     180
caggcccctg gacaagggct tgtgtggatg ggattaatca accctagtgg tggcagcaca     240
agctacgcac agaagttcca gggcagagtc accatgacca gggacacgtc cacgagcaca     300
gtctacatgg agctgagcag cctgagatct gaggacacgg ccgtgtatta ctgtgcgaga     360
tcggatcggg gaattaccgc cacggacgct tttgatatct ggggccaagg gacaatggtc     420
accgtctctt caggcggagg aggctccggg ggaggaggtt ccgggggcgg gggttcccag     480
tctgtgctga ctcagccacc ctcggtctca gtggccccag gcagacggc caagactacc     540 tgtgggggaa gtgacattgg aaataaaaat gtccactggt accagcagaa gccaggccag     600
gcccctgtcc tggtcgtcta tgatgattac gaccggccct cagggatccc tgagcgattc     660
tctggctcca actctgggga cgcggccacc ctgacgatca gcacggtcga agtcggggat     720
gaggccgact atgtctgtca ggtgtgggac ggtagtggtg atccttattg ggtgttcggc     780
ggagggaccc agctcaccgt tttaggtgcg gccgcaacta ccaccctgc ccctcggccg     840 ccgactccgg ccccaaccat cgcaagccaa cccctctcct gcgccccga gcttgccgc     900 ccggccgcgg gtggagccgt gcatacccgg ggctggact tgcctgcga tatctacatt     960 tgggccccgc tggccggcac ttgcggcgtg ctcctgctgt cgctggtcat caccctttac    1020
tgcaagaggg gccggaagaa gctgctttac atcttcaagc agccgttcat gcggcccgtg    1080
cagacgactc aggaagagga cggatgctcg tgcagattcc ctgaggagga agagggggga    1140
tgcgaactgc gcgtcaagtt ctcacggtcc gccgacgccc ccgcatatca cagggccag    1200 aatcagctct acaacgagct gaacctggga aggagagagg agtacgacgt gctggacaag    1260
cgacgcggac gcgacccgga gatgggggg aaaccacggc ggaaaaaccc tcaggaagga    1320
ctgtacaacg aactccagaa agacaagatg gcggaagcct actcagaaat cgggatgaag    1380
ggagagcgga ggaggggaaa gggtcacgac gggctgtacc agggactgag caccgccact    1440
aaggatacct acgatgcctt gcatatgcaa gcactcccac cccgg                   1485

<210> SEQ ID NO 34
<211> LENGTH: 495
```

<212> TYPE: PRT
<213> ORGANISM: Artificial Sequence
<220> FEATURE:
<223> OTHER INFORMATION: LTG2071 _(LP-M19217-40-CD8 TM-41BB-CD3 zeta)

<400> SEQUENCE: 34

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Arg Pro Gly Ala Ser Val Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Val Trp Met Gly Leu Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Ser Asp Arg Gly Ile Thr Ala Thr
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Gly Ser Gln
145                 150                 155                 160

Ser Val Leu Thr Gln Pro Pro Ser Val Ser Val Ala Pro Gly Gln Thr
                165                 170                 175

Ala Lys Thr Thr Cys Gly Gly Ser Asp Ile Gly Asn Lys Asn Val His
            180                 185                 190

Trp Tyr Gln Gln Lys Pro Gly Gln Ala Pro Val Leu Val Val Tyr Asp
        195                 200                 205

Asp Tyr Asp Arg Pro Ser Gly Ile Pro Glu Arg Phe Ser Gly Ser Asn
    210                 215                 220

Ser Gly Asp Ala Ala Thr Leu Thr Ile Ser Thr Val Glu Val Gly Asp
225                 230                 235                 240

Glu Ala Asp Tyr Val Cys Gln Val Trp Asp Gly Ser Gly Asp Pro Tyr
                245                 250                 255

Trp Val Phe Gly Gly Gly Thr Gln Leu Thr Val Leu Gly Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380
```

```
Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 35
<211> LENGTH: 66
<212> TYPE: DNA
<213> ORGANISM: Artificial Sequence
<220> FEATURE:
<223> OTHER INFORMATION: DNA CD8 transmembrane domain

<400> SEQUENCE: 35
atttgggccc cgctggccgg cacttgcggc gtgctcctgc tgtcgctggt catcaccctt    60
tactgc                                                              66

<210> SEQ ID NO 36
<211> LENGTH: 22
<212> TYPE: PRT
<213> ORGANISM: Artificial Sequence
<220> FEATURE:
<223> OTHER INFORMATION: CD8 transmembrane domain

<400> SEQUENCE: 36

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 37
<211> LENGTH: 141
<212> TYPE: DNA
<213> ORGANISM: Artificial Sequence
<220> FEATURE:
<223> OTHER INFORMATION: DNA CD8 hinge domain

<400> SEQUENCE: 37
actaccaccc ctgccccctcg gccgccgact ccggccccaa ccatcgcaag ccaaccccctc    60 tccttgcgcc ccgaagcttg ccgcccggcc gcgggtggag ccgtgcatac ccgggggctg   120
gactttgcct gcgatatcta c                                             141

<210> SEQ ID NO 38
<211> LENGTH: 46
<212> TYPE: PRT
<213> ORGANISM: Artificial Sequence
<220> FEATURE:
<223> OTHER INFORMATION: CD8 hinge domain

<400> SEQUENCE: 38

Thr Thr Thr Pro Ala Pro Arg Pro Pro Thr Pro Ala Pro Thr Ile Ala
1               5                   10                  15
```

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 39
<211> LENGTH: 69
<212> TYPE: PRT
<213> ORGANISM: Artificial Sequence
<220> FEATURE:
<223> OTHER INFORMATION: hinge and  transmembrane region of CD8.alpha.
      (NCBI RefSeq: NP.sub.--001759.3)

<400> SEQUENCE: 39

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 40
<211> LENGTH: 126
<212> TYPE: DNA
<213> ORGANISM: Artificial Sequence
<220> FEATURE:
<223> OTHER INFORMATION: signaling domain of 4-1BB

<400> SEQUENCE: 40
aagaggggcc ggaagaagct gctttacatc ttcaagcagc cgttcatgcg gcccgtgcag     60
acgactcagg aagaggacgg atgctcgtgc agattccctg aggaggaaga gggggatgc    120 gaactg                                                              126

<210> SEQ ID NO 41
<211> LENGTH: 42
<212> TYPE: PRT
<213> ORGANISM: Artificial Sequence
<220> FEATURE:
<223> OTHER INFORMATION: signaling domain of 4-1BB

<400> SEQUENCE: 41

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 42
<211> LENGTH: 336
<212> TYPE: DNA
<213> ORGANISM: Artificial Sequence
<220> FEATURE:
<223> OTHER INFORMATION: intracellular signaling domain of CD3-zeta

<400> SEQUENCE: 42
cgcgtcaagt tctcacggtc cgccgacgcc cccgcatatc aacagggcca gaatcagctc     60

```
tacaacgagc tgaacctggg aaggagagag gagtacgacg tgctggacaa gcgacgcgga    120
cgcgacccgg agatggggggg gaaaccacgg cggaaaaacc ctcaggaagg actgtacaac   180
gaactccaga aagacaagat ggcggaagcc tactcagaaa tcgggatgaa gggagagcgg    240
aggaggggaa aggtcacga cgggctgtac cagggactga gcaccgccac taaggatacc     300
tacgatgcct tgcatatgca agcactccca ccccgg                              336
```

```
<210> SEQ ID NO 43
<211> LENGTH: 112
<212> TYPE: PRT
<213> ORGANISM: Artificial Sequence
<220> FEATURE:
<223> OTHER INFORMATION: CD3-zeta

<400> SEQUENCE: 43
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 44
<211> LENGTH: 336
<212> TYPE: DNA
<213> ORGANISM: Artificial Sequence
<220> FEATURE:
<223> OTHER INFORMATION: intracellular signaling domain of CD3-zeta,
      variant

<400> SEQUENCE: 44
cgcgtcaagt tctcacggtc cgccgacgcc cccgcatata acagggcca gaatcagctc    60 tacaacgagc tgaacctggg aaggagagag gagtacgacg tgctggacaa gcgacgcgga   120
cgcgacccgg agatggggggg gaaaccacgg cggaaaaacc ctcaggaagg actgtacaac  180
gaactccaga aagacaagat ggcggaagcc tactcagaaa tcgggatgaa gggagagcgg   240
aggaggggaa aggtcacga cgggctgtac cagggactga gcaccgccac taaggatacc    300
tacgatgcct tgcatatgca agcactccca ccccgg                             336
```

```
<210> SEQ ID NO 45
<211> LENGTH: 112
<212> TYPE: PRT
<213> ORGANISM: Artificial Sequence
<220> FEATURE:
<223> OTHER INFORMATION: CD3-zeta signaling domain, variant

<400> SEQUENCE: 45
```

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr

```
            20                  25                  30
Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 46
<211> LENGTH: 726
<212> TYPE: DNA
<213> ORGANISM: Artificial Sequence
<220> FEATURE:
<223> OTHER INFORMATION: ScFv CD19 (FMC63)

<400> SEQUENCE: 46
gacattcaga tgactcagac cacctcttcc ttgtccgcgt cactgggaga cagagtgacc        60
atctcgtgtc gcgcaagcca ggatatctcc aagtacctga actggtacca acagaagccc       120
gacgggactg tgaagctgct gatctaccac acctcacgcc tgcacagcgg agtgccaagc       180
agattctccg gctccggctc gggaaccgat tactcgctta ccattagcaa cctcgagcag       240
gaggacatcg ctacctactt ctgccagcaa ggaaatacco tgccctacac cttcggcgga       300
ggaaccaaat tggaaatcac cggcggagga ggctccgggg aggaggttc cggggcggg        360 ggttccgaag tgaagctcca ggagtccggc cccggcctgg tggcgccgtc gcaatcactc       420
tctgtgacct gtaccgtgtc gggagtgtcc ctgcctgatt acggcgtgag ctggattcgg       480
cagccgccgc ggaagggcct ggaatggctg gtgtgtcatct ggggatccga gactacctac       540
tacaactcgg ccctgaagtc ccgcctgact atcatcaaag acaactcgaa gtcccaggtc       600
tttctgaaga tgaactccct gcaaactgac gacaccgcca tctattactg tgctaagcac       660
tactactacg gtggaagcta tgctatggac tactgggggc aaggcacttc ggtgactgtg       720
tcaagc                                                                 726

<210> SEQ ID NO 47
<211> LENGTH: 242
<212> TYPE: PRT
<213> ORGANISM: Artificial Sequence
<220> FEATURE:
<223> OTHER INFORMATION: ScFv CD19 (FMC63)

<400> SEQUENCE: 47

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
```

```
                85                  90                  95
Thr Phe Gly Gly Gly Thr Lys Leu Glu Ile Thr Gly Gly Gly Ser
                100                 105                 110
Gly Gly Gly Gly Ser Gly Gly Gly Ser Glu Val Lys Leu Gln Glu
                115                 120                 125
Ser Gly Pro Gly Leu Val Ala Pro Ser Gln Ser Leu Ser Val Thr Cys
    130                 135                 140
Thr Val Ser Gly Val Ser Leu Pro Asp Tyr Gly Val Ser Trp Ile Arg
145                 150                 155                 160
Gln Pro Pro Arg Lys Gly Leu Glu Trp Leu Gly Val Ile Trp Gly Ser
                165                 170                 175
Glu Thr Thr Tyr Tyr Asn Ser Ala Leu Lys Ser Arg Leu Thr Ile Ile
                180                 185                 190
Lys Asp Asn Ser Lys Ser Gln Val Phe Leu Lys Met Asn Ser Leu Gln
                195                 200                 205
Thr Asp Asp Thr Ala Ile Tyr Tyr Cys Ala Lys His Tyr Tyr Gly
                210                 215                 220
Gly Ser Tyr Ala Met Asp Tyr Trp Gly Gln Gly Thr Ser Val Thr Val
225                 230                 235                 240
Ser Ser

<210> SEQ ID NO 48
<211> LENGTH: 747
<212> TYPE: DNA
<213> ORGANISM: Artificial Sequence
<220> FEATURE:
<223> OTHER INFORMATION: anti-CD33 ScFv (LTG1936)

<400> SEQUENCE: 48
caggtgcagc tggtgcaatc tgggcagag gtgaaaaagc cggggagtc tctgaggatc      60
tcctgtaagg gttctggatt cagttttccc acctactgga tcggctgggt gcgccagatg    120
cccgggaaag gcctggagtg gatggggatc atctatcctg gtgactctga taccagatac    180
agcccgtcct ccaaggcca ggtcaccatc tcagccgaca gtccatcag caccgcctac      240
ctgcagtgga gcagcctgaa ggcctcggac accgccatgt attactgtgc gagactagtt    300
ggagatggct acaatacggg ggcttttgat atctggggcc aagggacaat ggtcaccgtc    360
tcttcaggag gtggcgggtc tggtggtggc ggtagcggtg gtggcggatc cgatattgtg    420
atgacccaca ctccactctc tctgtccgtc acccctggac agccggcctc catctcctgc    480
aagtctagtc agagcctcct gcatagtaat ggaaagacct atttgtattg gtacctgcag    540
aagccaggcc agcctccaca gctcctgatc tatggagctt ccaaccggtt ctctggagtg    600
ccagacaggt tcagtggcag cgggtcaggg acagatttca cactgaaaat cagccgggtg    660
gaggctgagg atgttggggt ttattactgc atgcaaagta cagcttcc tatcaccttc      720
ggccaaggga cacgactgga gattaaa                                        747

<210> SEQ ID NO 49
<211> LENGTH: 249
<212> TYPE: PRT
<213> ORGANISM: Artificial Sequence
<220> FEATURE:
<223> OTHER INFORMATION: anti-CD33 ScFv (LTG1936)

<400> SEQUENCE: 49

Gln Val Gln Leu Val Gln Ser Gly Ala Glu Val Lys Lys Pro Gly Glu
1               5                   10                  15
```

```
Ser Leu Arg Ile Ser Cys Lys Gly Ser Gly Phe Ser Phe Pro Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Gly Asp Gly Tyr Asn Thr Gly Ala Phe Asp Ile Trp
            100                 105                 110

Gly Gln Gly Thr Met Val Thr Val Ser Ser Gly Gly Gly Gly Ser Gly
            115                 120                 125

Gly Gly Gly Ser Gly Gly Gly Gly Ser Asp Ile Val Met Thr His Thr
        130                 135                 140

Pro Leu Ser Leu Ser Val Thr Pro Gly Gln Pro Ala Ser Ile Ser Cys
145                 150                 155                 160

Lys Ser Ser Gln Ser Leu Leu His Ser Asn Gly Lys Thr Tyr Leu Tyr
                165                 170                 175

Trp Tyr Leu Gln Lys Pro Gly Gln Pro Pro Gln Leu Leu Ile Tyr Gly
            180                 185                 190

Ala Ser Asn Arg Phe Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
        210                 215                 220

Val Gly Val Tyr Tyr Cys Met Gln Ser Ile Gln Leu Pro Ile Thr Phe
225                 230                 235                 240

Gly Gln Gly Thr Arg Leu Glu Ile Lys
                245

<210> SEQ ID NO 50
<211> LENGTH: 732
<212> TYPE: DNA
<213> ORGANISM: Artificial Sequence
<220> FEATURE:
<223> OTHER INFORMATION: anti-mesothelin ScFv (LTG1904)

<400> SEQUENCE: 50
gaggtccagc tggtacagtc tgggggaggc ttggtacagc ctgggggtc cctgagactc       60 tcctgtgcag cctctggatt cacctttgat gattatgcca tgcactgggt ccggcaagct     120
ccagggaagg gcctggagtg gtctcaggt attagttgga atagtggtag cataggctat     180
gcggactctg tgaagggccg attcaccatc tccagagaca acgccaagaa ctccctgtat    240
ctgcaaatga acagtctgag agctgaggac acggccttgt attactgtgc aaaagattta    300
tcgtcagtgg ctggacccct taactactgg ggccagggca ccctggtcac cgtctcctca    360
```

```
ggaggtggcg ggtctggtgg aggcggtagc ggcggtggcg atcctcttc  tgagctgact      420 caggaccctg ctgtgtctgt ggccttggga cagacagtca ggatcacatg ccaaggagac      480
agcctcagaa gctattatgc aagctggtac cagcagaagc caggacaggc ccctgtactt      540
gtcatctatg gtaaaaacaa ccggccctca gggatcccag accgattctc tggctccagc      600
tcaggaaaca cagcttcctt gaccatcact ggggctcagg cggaggatga ggctgactat      660
tactgtaact cccgggacag cagtggtaac catctggtat tcggcggagg cacccagctg      720
accgtcctcg gt                                                          732
```

```
<210> SEQ ID NO 51
<211> LENGTH: 244
<212> TYPE: PRT
<213> ORGANISM: Artificial Sequence
<220> FEATURE:
<223> OTHER INFORMATION: anti-mesothelin ScFv (LTG1904)

<400> SEQUENCE: 51
```

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Ser Ser Val Ala Gly Pro Phe Asn Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Leu Val Phe Gly Gly Gly Thr Gln Leu
225                 230                 235                 240

Thr Val Leu Gly